US011185539B2

(12) United States Patent
Thum et al.

(10) Patent No.: US 11,185,539 B2
(45) Date of Patent: Nov. 30, 2021

(54) NATURAL COMPOUNDS AND FIBROSIS

(71) Applicant: MEDIZINISCHE HOCHSCHULE HANNOVER (MHH), Hannover (DE)

(72) Inventors: Thomas Thum, Hannover (DE); Katharina Schimmel, Hannover (DE); Quoc-Tuan Do, Orleans (FR); Philippe Bernard, La Ferte Saint-Aubin (FR)

(73) Assignee: MEDIZINISCHE HOCHSCHULE HANNOVER (MHH), Hannover (DE)

( * ) Notice: Subject to any disclaimer, the term of this patent is extended or adjusted under 35 U.S.C. 154(b) by 0 days.

(21) Appl. No.: 16/481,569

(22) PCT Filed: Jan. 29, 2018

(86) PCT No.: PCT/EP2018/052096
§ 371 (c)(1),
(2) Date: Jul. 29, 2019

(87) PCT Pub. No.: WO2018/141678
PCT Pub. Date: Aug. 9, 2018

(65) Prior Publication Data
US 2019/0350923 A1 Nov. 21, 2019

(30) Foreign Application Priority Data
Jan. 31, 2017 (LU) .................................. LU100037

(51) Int. Cl.
| | | |
|---|---|---|
| *A61K 31/4741* | (2006.01) | |
| *A61P 9/00* | (2006.01) | |
| *A61K 31/401* | (2006.01) | |
| *A61K 31/585* | (2006.01) | |
| *A61K 9/00* | (2006.01) | |
| *G01N 33/50* | (2006.01) | |

(52) U.S. Cl.
CPC ........ *A61K 31/4741* (2013.01); *A61K 9/0019* (2013.01); *A61K 31/401* (2013.01); *A61K 31/585* (2013.01); *A61P 9/00* (2018.01); *G01N 33/5023* (2013.01); *G01N 33/5061* (2013.01)

(58) Field of Classification Search
None
See application file for complete search history.

(56) References Cited

U.S. PATENT DOCUMENTS 7,081,345 B1 * 7/2006 Roecklin .................. A61P 29/00
435/7.1

FOREIGN PATENT DOCUMENTS

| CN | 100368022 | 2/2008 |
|---|---|---|
| JP | 2005527611 | 9/2005 |
| WO | 2002002123 | 1/2002 |
| WO | 2003099011 | 12/2003 |
| WO | 2009105234 | 8/2009 |
| WO | 2013000286 | 1/2013 |
| WO | 2016028753 | 2/2016 |
| WO | 2017136515 | 8/2017 |

OTHER PUBLICATIONS

Wang et al, ChemMedChem, vol. 9, pp. 1522-1533, (Year: Feb. 26, 2014).*
Nanthakumar et al, Nature Reviews, Drug Discovery, vol. 14, pp. 693-720, (Year: Oct. 2015).*
Birbrair et al., "Type-1 pericytes accumulate after tissue injury and produce collagen in an organ-dependent manner", Stem Cell Research & Therapy, 2014, 5: 122. 18 pages.
Grollmann "Inhibitors of protein biosynthesis",The Journal of Biological Chemistry, 1967, 242:3226-3233.
Guo et al., "A conserved inhibitory mechanism of a Lycorine derivative against enterovirus and hepatitis C virus", Antimicrobial Agents and Chemotherapy, 2016, 60:913-924.
Murakami et al., "Comprehensive miRNA expression analysis in peripheral blood can diagnose liver disease", 2012, PLoS ONE 7(10):e48366. 15 pages.
Nathan et al., "Assessment of Myocardial Fibrosis with Cardiac Magnetic Resonance", Journal of the American College of Cardiology, 2011, 57:891-903.
Neary et al., "Epigenetics and the overhealing wound: the role of DNA methylation in fibrosis", Fibrogenesis & Tissue Repair, 2015, 8:18. 13 pages.
O'Reilly "MicroRNAs in fibrosis: opportunities and challenges ", Arthritis Research & Therapy, 2016, 18:11. 10 pages.
Prassas et al., "Novel therapeutic applications of cardiac glycosides", Nature Review, 2008, 7:926-935.
Rajasekaran et al., "MicroRNAs as potential targets for progressive pulmonary fibrosis", Frontiers in Pharmacology, 2015, 6:254. 15 pages.
Schulte et al., "Antibiotic radicicol binds to the N-terminal domain of Hsp90 and shares important biologic activities with geldanamycin", Cell Stress & Chaperones, 1998, 3:100-108.
Schulte et al., "Diagnostic and prognostic value of circulating microRNAs in heart failure with preserved and reduced ejection fraction", World J. Cardiol., 2015, 7:843-860.
Schulte et al., "MicroRNAs in cardiovascular disease—clinical application", Clin. Chem. Lab. Med., 2016, 55:687-704.
Thum "Noncoding RNAs and myocardial fibrosis", Nature Reviews Cardiology, 2014, 11:655-663.
Vegter et al., "MicroRNAs in heart failure: from biomarker to target for therapy", European Journal of Heart Failure, 2016, 18:457-468.
Wang et al., "MicroRNA-24 regulates cardiac fibrosis after myocardial infarction", J. Cell. Mol. Med., 2012, 16:2150-2160.
Wang et al., "Novel Lycorine derivatives as anticancer agents: Synthesis and in vitro biological evaluation", Molecules, 2014, 19:2469-2480.
Wilson et al., "Pulmonary fibrosis: pathogenesis, etiology and regulation", Mucosal Immunology, 2009, 2:103-121.

(Continued)

*Primary Examiner* — Zinna Northington Davis
(74) *Attorney, Agent, or Firm* — Riverside Law LLP

(57) ABSTRACT

The present invention relates to an inhibitor of miR-671-5p for use in a method of preventing or treating fibrosis. Further, the present invention encompasses a kit comprising said inhibitor of miR-671-5p. The present invention also relates to an in vitro method for identifying a compound for preventing or treating fibrosis.

6 Claims, 94 Drawing Sheets

Specification includes a Sequence Listing.

(56) References Cited

OTHER PUBLICATIONS

Wong et al., "Circulating microRNAs in heart failure with reduced and preserved left ventricular ejection fraction", European J. of Heart Failure, 2015, 17:393-404.
Gordon et al., "A Cell-Based Screening Assay to Identify Pharmaceutical Compounds That Enhance the Regenerative Quality of Corneal Repair", 2016, Wound Rep. Reg., 24:89-99.
Hu et al., "Lycorine is a Novel Inhibitor of the Growth and Metastasis of Hormone-Refractory Prostate Cancer", 2015, Oncotarget, 6:15348-15361.
Miguel Lopez-Novoa et al., "Inflammation and EMT: an al Hance towards organ fibrosis and cancer progression", 2009, EMBO Mol Med, 1:303- 314.
Zhao et al., "Bufalin Inhibits TGF-b-lnduced Epithelial-to-Mesenchymal Transition and Migration in Human Lung Cancer A549 Cells by Downregulating TGF-b Receptors", 2015, International Journal of Molecular Medicine, 36:645-652.

\* cited by examiner

Figure 2
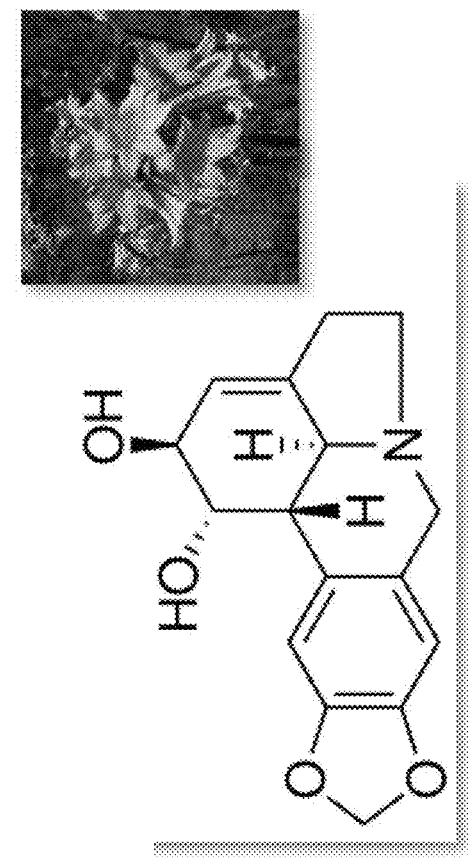
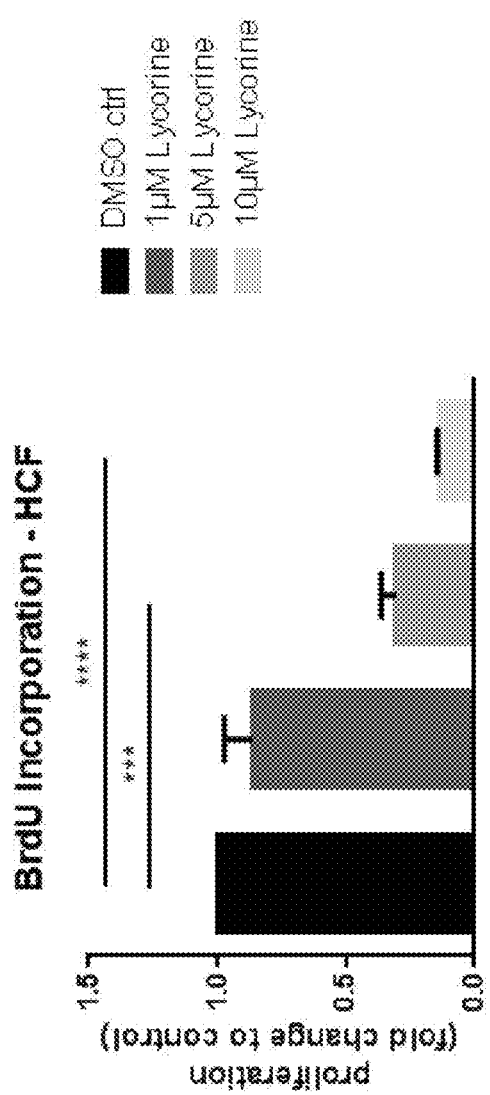

Figure 7
Bufalin and Lycorine ameliorate cardiac function
A
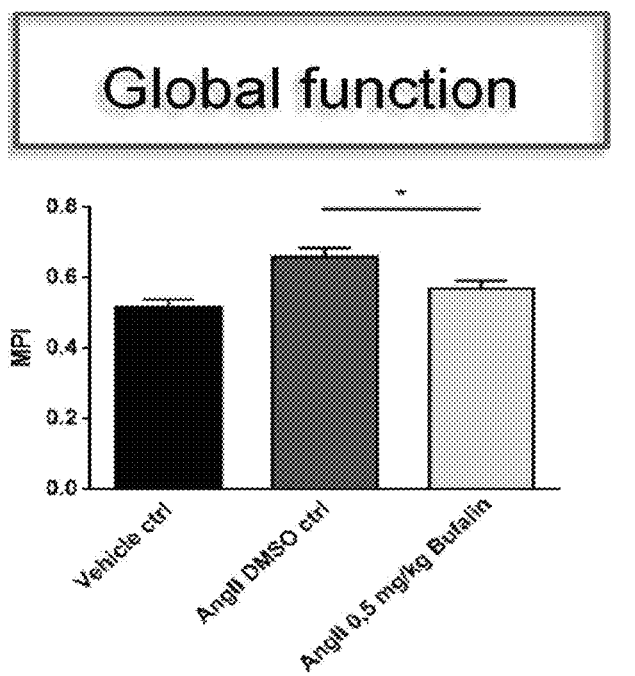
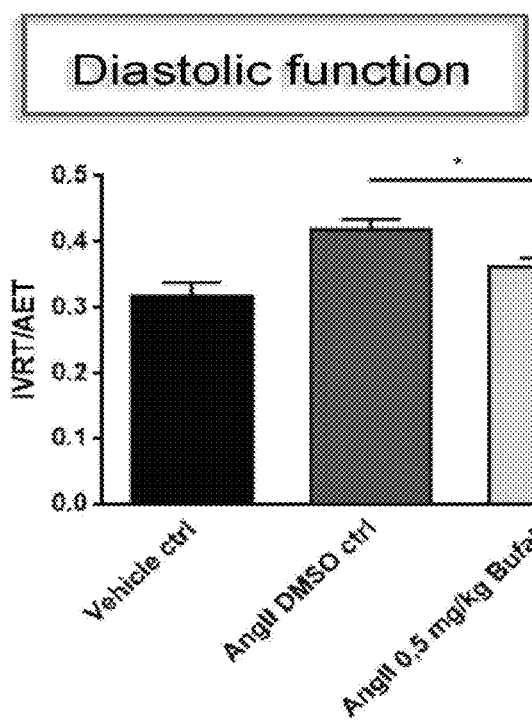

Figure 7 (cont.)
Bufalin and Lycorine ameliorate cardiac function
B
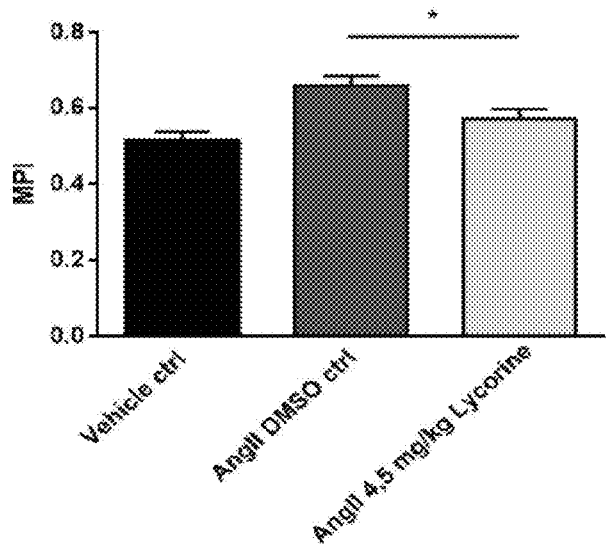
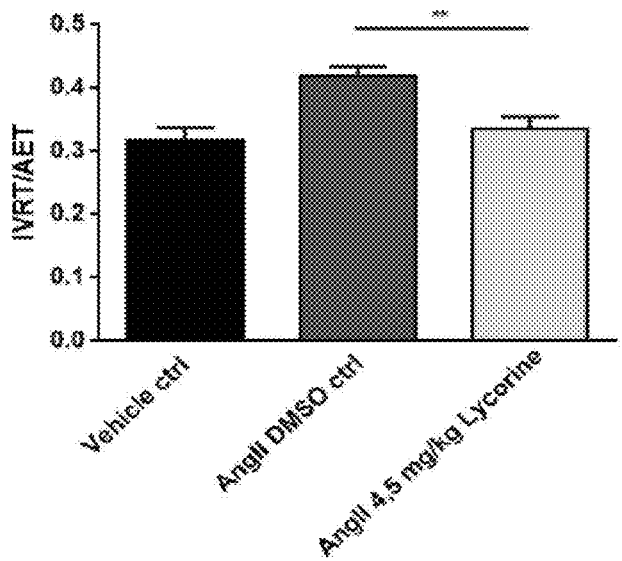

Figure 9
Anisomycin and Gitoxigenin ameliorate cardiac function
A
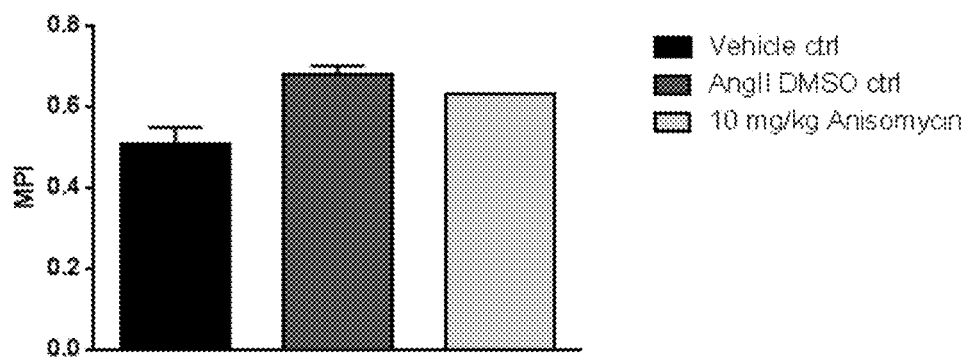
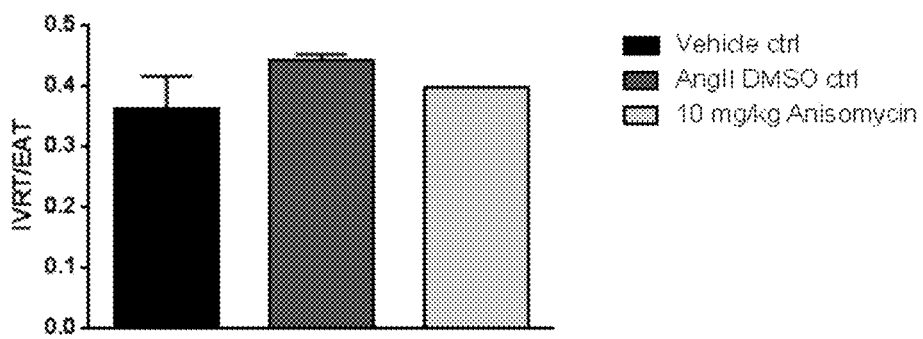

Figure 16

| top50 | | | | | | | | |
|---|---|---|---|---|---|---|---|---|
| mature | structure | Sample1_1uM_Bufalin | Sample2_1uM_Bufalin | Sample3_1uM_Bufalin | Sample1_DMSO | Sample2_DMSO | Sample3_DMSO |
| hsa-miR-7974 | mirna | 13.00 | 10.88 | 7.04 | 138.24 | 126.35 | 139.00 |
| hsa-miR-103a-3p | mirna | 9.45 | 13.60 | 5.87 | 82.94 | 96.62 | 99.79 |
| hsa-miR-4521 | mirna | 16.54 | 13.60 | 28.18 | 114.54 | 80.69 | 87.32 |
| hsa-miR-23b-5p | mirna | 3.54 | 8.16 | 4.70 | 21.07 | 23.36 | 17.82 |
| hsa-miR-100-3p | mirna | 628.62 | 717.82 | 706.73 | 2284.90 | 2475.94 | 2612.44 |
| hsa-miR-3648 | mirna | 9.45 | 4.08 | 2.35 | 14.48 | 13.80 | 19.60 |
| hsa-miR-128-1-5p | mirna | 13.00 | 14.95 | 27.00 | 43.45 | 54.15 | 63.26 |
| hsa-miR-29b-1-5p | mirna | 43.72 | 32.63 | 21.13 | 92.82 | 69.01 | 88.21 |
| hsa-miR-605-3p | mirna | 13.00 | 20.39 | 12.91 | 40.81 | 36.10 | 33.86 |
| hsa-miR-370-5p | mirna | 14.18 | 12.24 | 8.22 | 24.36 | 24.42 | 32.08 |
| hsa-miR-152-5p | mirna | 139.43 | 141.39 | 151.44 | 315.32 | 316.39 | 371.55 |
| hsa-miR-25-5p | mirna | 38.99 | 54.38 | 23.48 | 96.11 | 91.31 | 78.41 |
| hsa-miR-671-3p | mirna | 345.03 | 369.79 | 321.67 | 724.11 | 781.43 | 829.53 |
| hsa-miR-1226-3p | mirna | 21.27 | 35.35 | 25.83 | 54.64 | 61.58 | 64.15 |
| hsa-miR-296-3p | mirna | 24.81 | 36.71 | 37.57 | 67.14 | 79.63 | 69.50 |
| hsa-miR-409-5p | mirna | 1525.47 | 1858.45 | 2012.20 | 3702.18 | 3585.44 | 4014.88 |
| hsa-miR-221-5p | mirna | 4386.16 | 3882.77 | 4423.55 | 9814.98 | 7045.60 | 8454.77 |
| hsa-miR-502-3p | mirna | 53.17 | 73.41 | 63.39 | 115.20 | 135.90 | 113.16 |
| hsa-miR-1301-3p | mirna | 137.07 | 172.66 | 162.01 | 286.35 | 278.17 | 307.40 |
| hsa-miR-125b-5p | mirna | 1175.71 | 1129.75 | 1319.55 | 2404.05 | 2024.71 | 2227.52 |
| hsa-miR-671-5p | mirna | 99.26 | 125.08 | 129.14 | 232.37 | 199.60 | 205.82 |
| hsa-miR-1271-5p | mirna | 1023.28 | 1132.47 | 1373.55 | 2115.72 | 1910.04 | 2341.57 |
| novelmirna | novelmirna | 1023.28 | 1132.47 | 1373.55 | 2115.72 | 1910.04 | 2341.57 |
| hsa-miR-100-5p | mirna | 597213.66 | 592439.92 | 629025.12 | 1160922.69 | 1034182.38 | 1076345.59 |
| hsa-miR-181b-5p | mirna | 59.08 | 59.82 | 30.52 | 79.65 | 83.88 | 103.36 |
| hsa-miR-27b-5p | mirna | 626.26 | 591.39 | 531.81 | 1086.82 | 1024.56 | 996.15 |
| hsa-miR-330-3p | mirna | 50.81 | 55.74 | 50.48 | 82.29 | 96.62 | 95.34 |
| hsa-miR-92a-1-5p | mirna | 7.09 | 9.52 | 9.39 | 13.17 | 13.80 | 16.93 |
| hsa-miR-543 | mirna | 197.33 | 222.96 | 173.75 | 346.26 | 362.05 | 287.80 |
| hsa-miR-188-5p | mirna | 116.98 | 144.11 | 138.53 | 201.43 | 253.75 | 206.71 |
| hsa-miR-128-3p | mirna | 371.03 | 414.65 | 437.89 | 644.46 | 690.12 | 689.64 |
| hsa-miR-1185-1-3p | mirna | 139.43 | 152.27 | 138.53 | 227.77 | 242.07 | 237.01 |
| hsa-miR-1343-3p | mirna | 30.72 | 28.55 | 36.39 | 54.64 | 52.02 | 49.90 |
| hsa-miR-26b-3p | mirna | 57.90 | 78.85 | 82.18 | 113.88 | 117.85 | 125.63 |

| top50 | | | | | | | |
|---|---|---|---|---|---|---|---|
| mature | structure | Sample1_1uM_Bufalin | Sample2_1uM_Bufalin | Sample3_1uM_Bufalin | Sample1_DMSO | Sample2_DMSO | Sample3_DMSO |
| hsa-miR-4443 | mirna | 18,91 | 17,67 | 14,09 | 2,63 | 5,31 | 4,46 |
| hsa-miR-7977 | mirna | 24,81 | 36,71 | 27,00 | 5,27 | 7,43 | 16,04 |
| hsa-miR-192-5p | mirna | 3822,53 | 3817,51 | 3901,13 | 1540,38 | 1480,04 | 1585,10 |
| hsa-miR-33b-5p | mirna | 47,26 | 44,86 | 39,92 | 22,38 | 27,60 | 18,71 |
| hsa-miR-132-3p | mirna | 1419,12 | 1748,33 | 1611,87 | 902,50 | 835,58 | 819,73 |
| novelmirna | novelmirna | 80,35 | 82,93 | 68,09 | 53,98 | 38,22 | 46,33 |
| hsa-miR-27a-5p | mirna | 402,93 | 439,12 | 378,02 | 228,42 | 185,80 | 251,26 |
| hsa-miR-215-5p | mirna | 48,45 | 57,10 | 51,65 | 26,99 | 33,98 | 25,84 |
| hsa-miR-218-1-3p | mirna | 135,89 | 133,23 | 132,66 | 75,70 | 70,07 | 78,41 |
| novelmirna | novelmirna | 1687,35 | 2251,35 | 2667,28 | 812,98 | 1034,12 | 1284,83 |
| hsa-miR-132-5p | mirna | 187,88 | 240,63 | 243,01 | 141,53 | 141,21 | 101,57 |
| hsa-miR-675-5p | mirna | 42,54 | 53,02 | 48,13 | 19,75 | 27,60 | 35,64 |
| hsa-miR-451a | mirna | 31,90 | 40,79 | 34,05 | 22,38 | 25,48 | 14,26 |
| hsa-miR-770-5p | mirna | 44,90 | 44,86 | 54,00 | 23,04 | 27,60 | 35,64 |
| hsa-miR-142-5p | mirna | 27,18 | 35,35 | 37,57 | 23,70 | 23,36 | 13,37 |
| hsa-miR-668-3p | mirna | 81,53 | 78,85 | 96,27 | 51,35 | 56,27 | 49,01 |

High-throughput miRNA sequencing in human cardiac fibroblasts treated with anti-fibrotic compounds
miR-671-5p as a general target Figure 18
miR-671-5p regulates fibrosis and inflammation
A
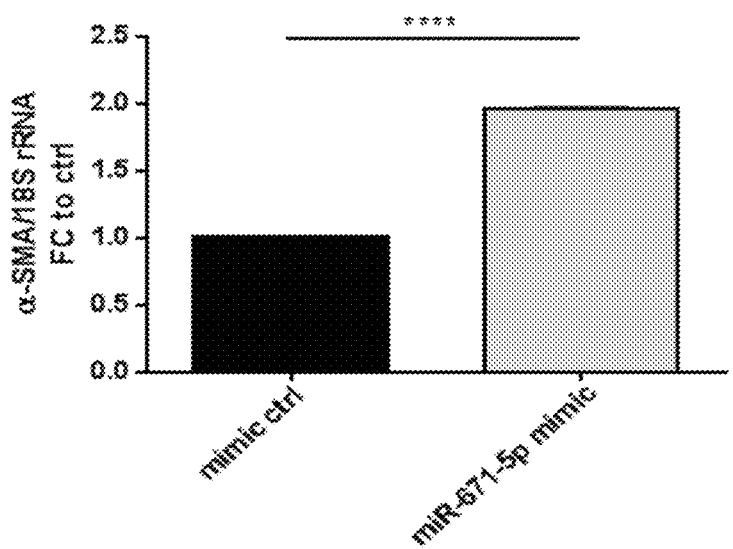
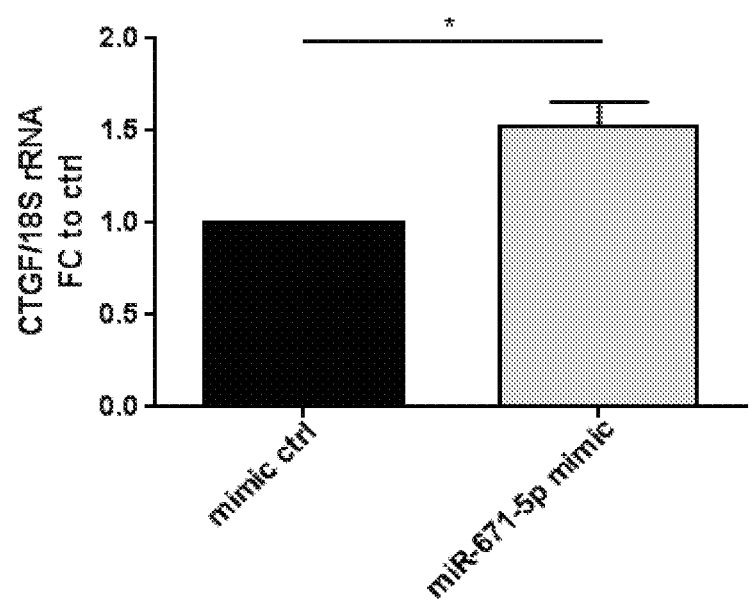

Figure 18 (cont.)
B
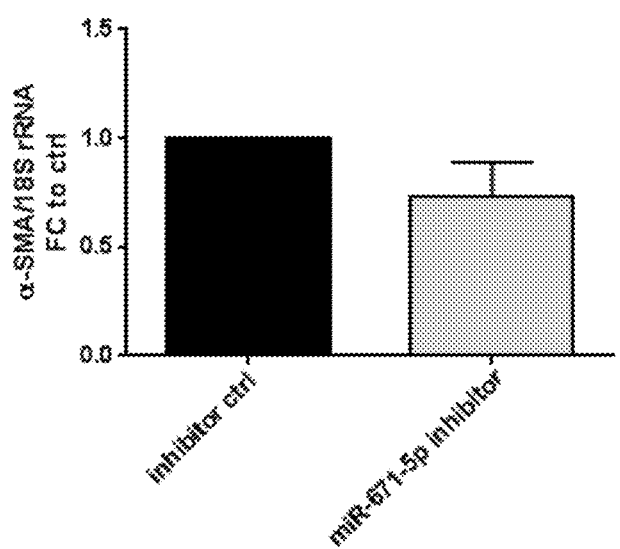
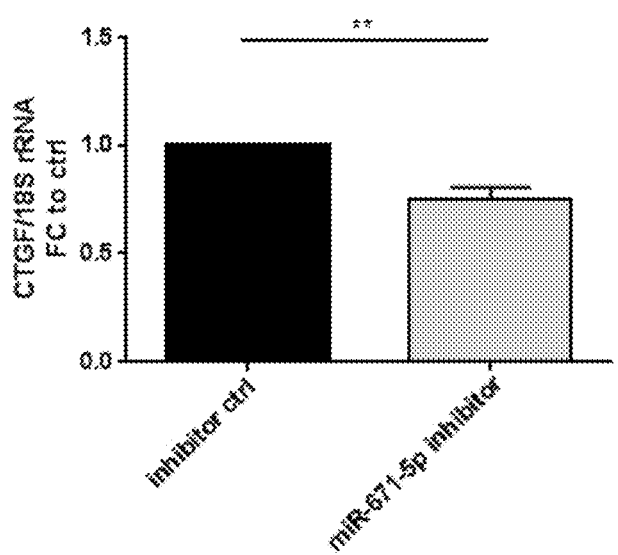

Figure 18 (cont.)
B
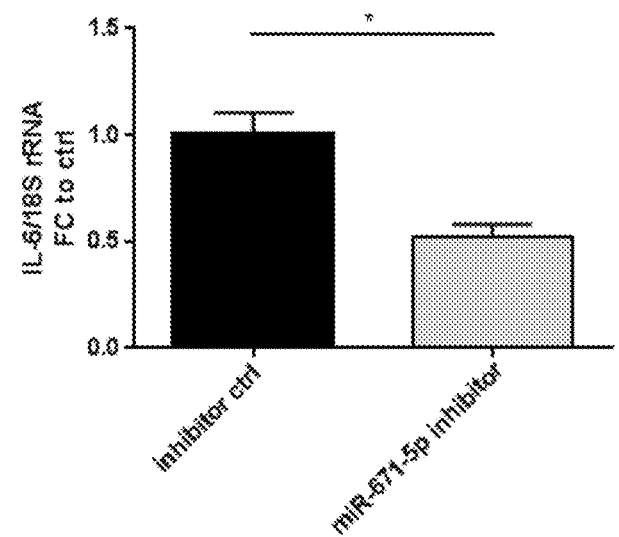
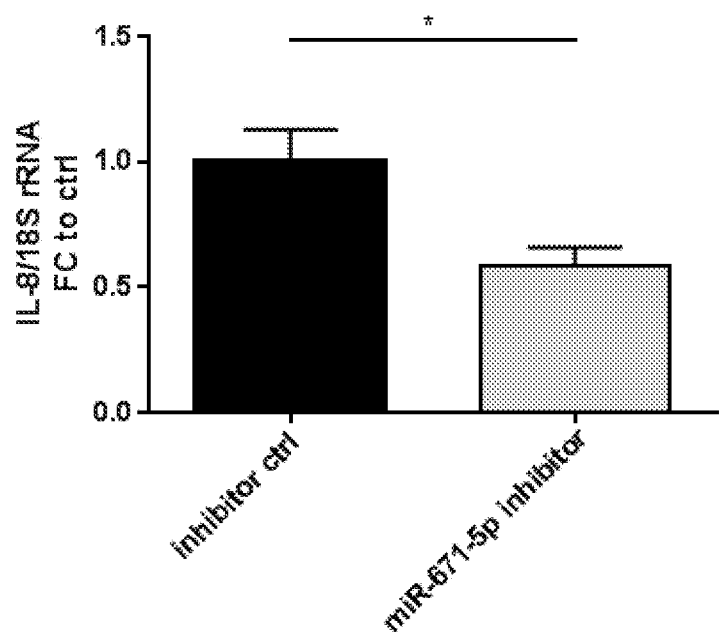

Figure 20
miR-671-5p levels change in cardiac fibrotic diseases
A
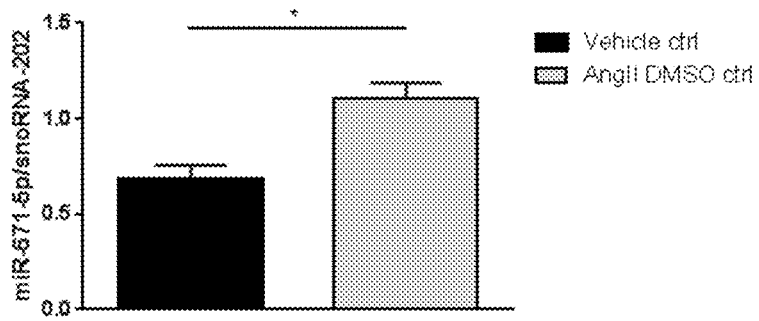
B
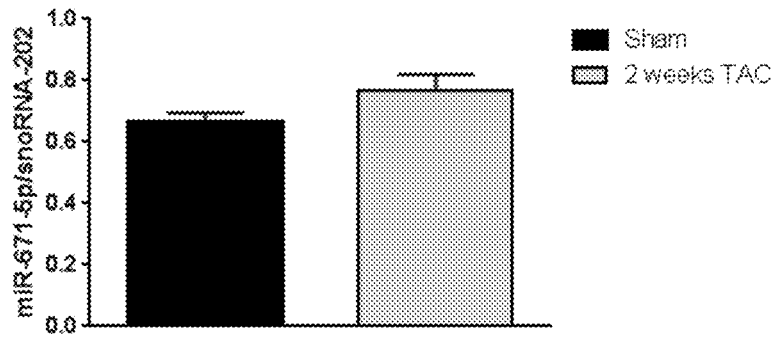
C
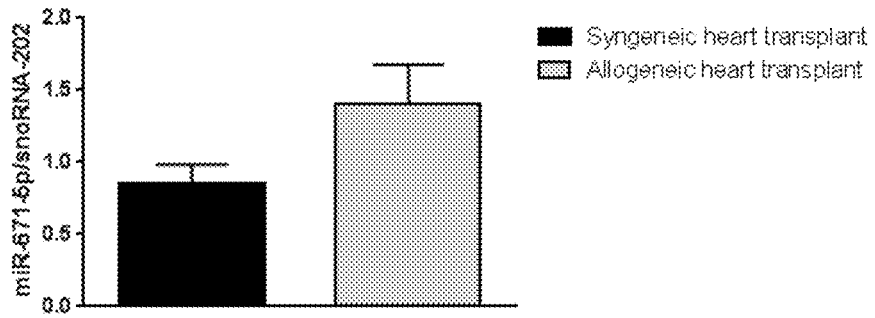
D
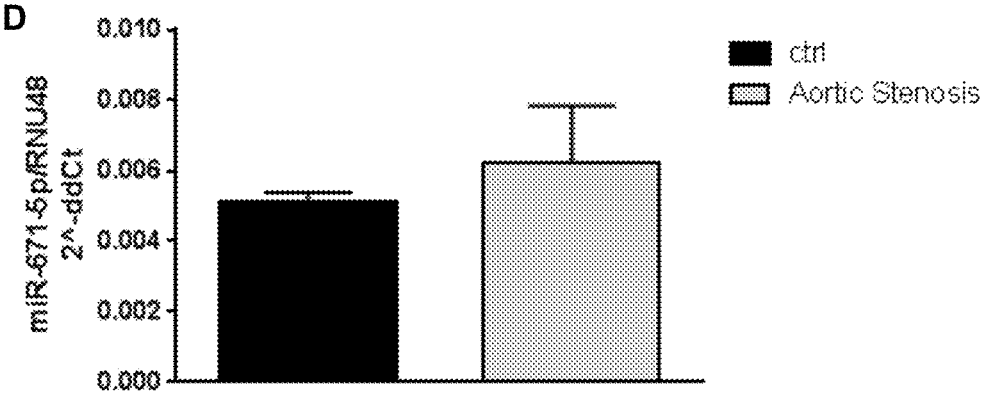

Figure 21 miR-671-5p targets the circular RNA *CDR1as*

A

| | Predicted consequential pairing of target region (top) and miRNA (bottom) |
|---|---|
| Position 99-105 of CDR1as 3' UTR | 5'  ...UCCAGAUAAUCCUGAGCUUCCAG... |
| hsa-miR-671-5p | 3'       GAGGUCGGGGAGGUCCCGAAGGA |
| Position 851-857 of CDR1as 3' UTR | 5'  ...UCCCUUAAAUCUAUAGCUUCCAA... |
| hsa-miR-671-5p | 3'       GAGGUCGGGGAGGUCCCGAAGGA |
| Position 1300-1307 of CDR1as 3' UTR | 5'  ...UUCCAGCAUCUCCAGGGCUUCCA... |
| hsa-miR-671-5p | 3'       GAGGUCGGGGAGGUCCCGAAGGA |

*TargetScanHuman v.7.0*

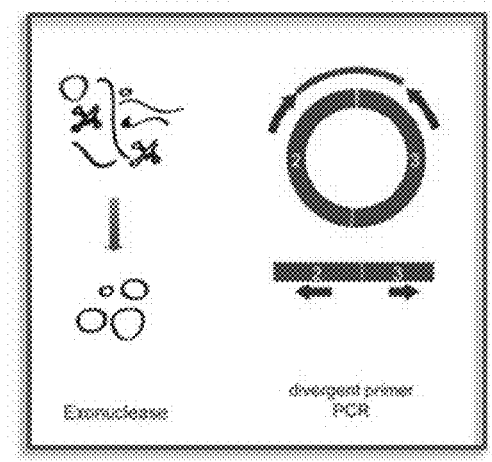

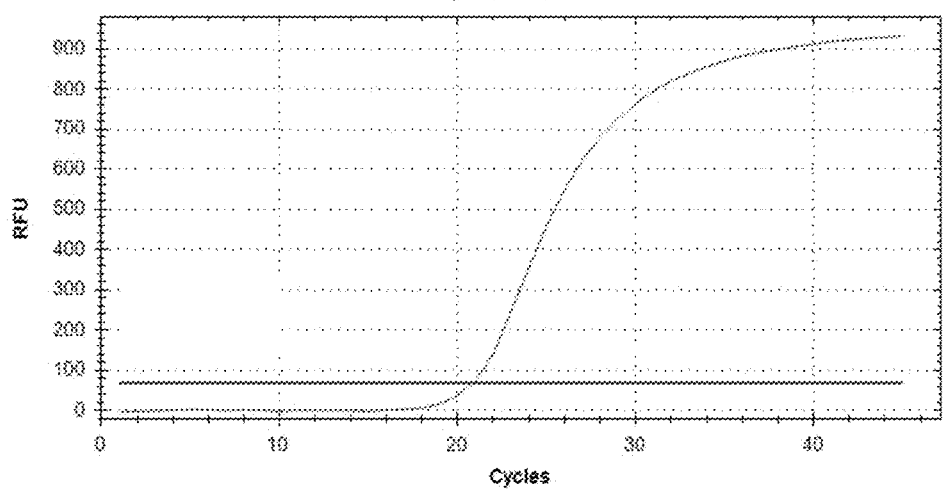

Figure 21 (cont.)
B
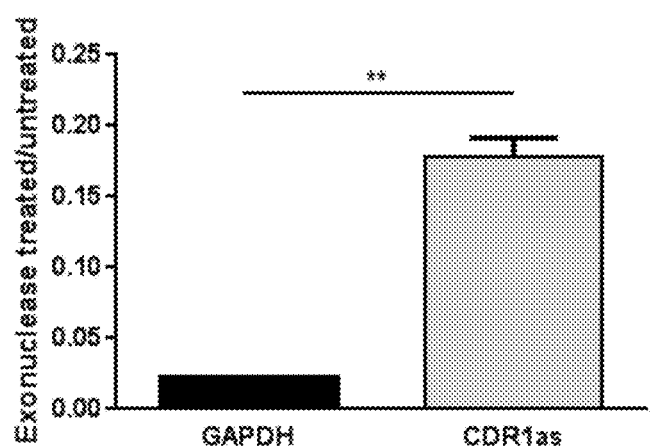
C
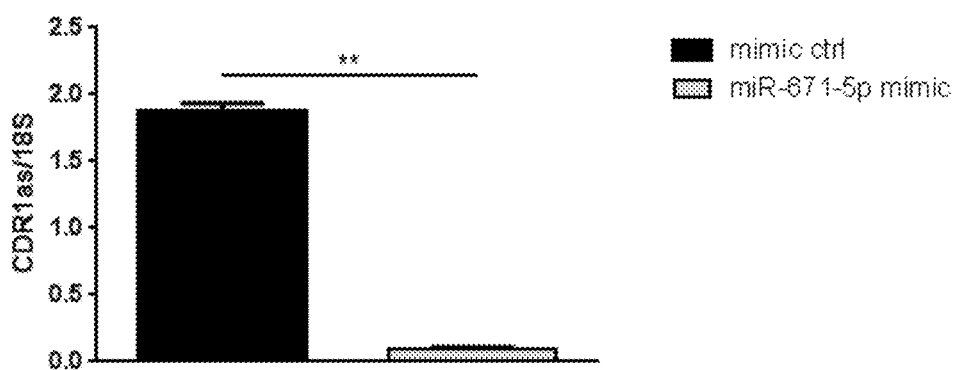

Figure 22
_CDR1as_ levels increase in human cardiac fibroblasts after treatment with anti-fibrotic natural compounds
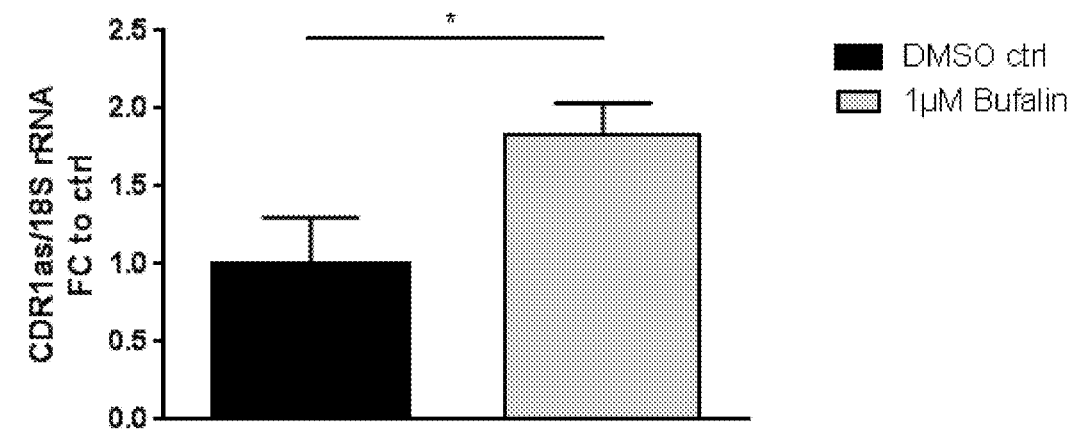
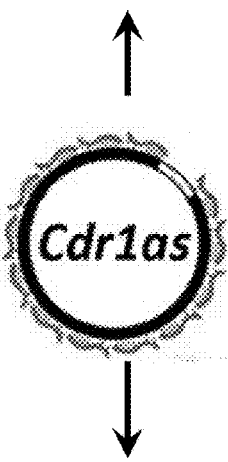
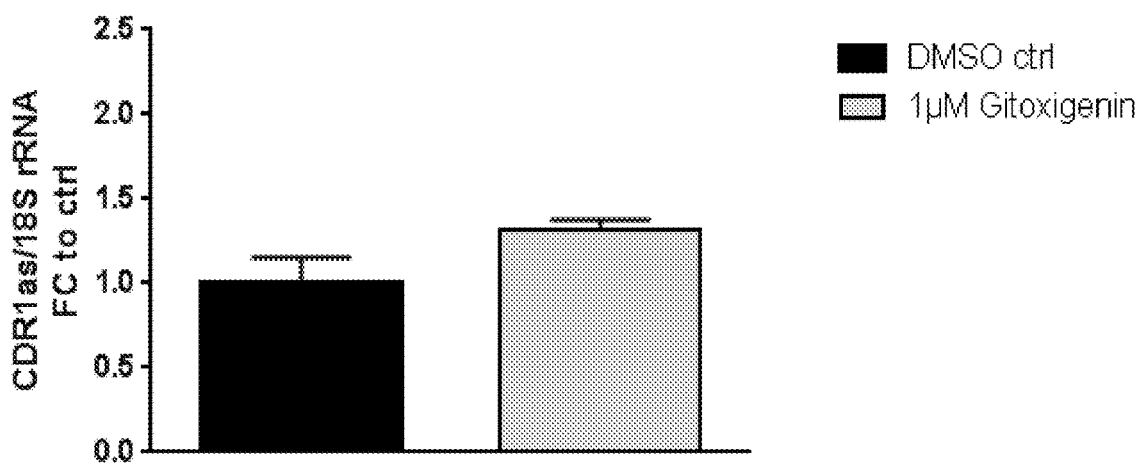

CDR1 mRNA levels decrease in human cardiac fibroblasts after treatment with anti-fibrotic natural compounds

Figure 25
miR-671-5p targets Selenoprotein P
A
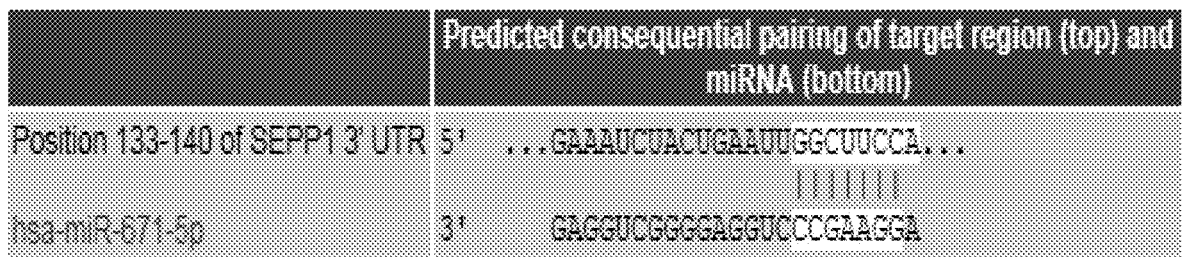
*TargetScanHuman v.7.0*
B
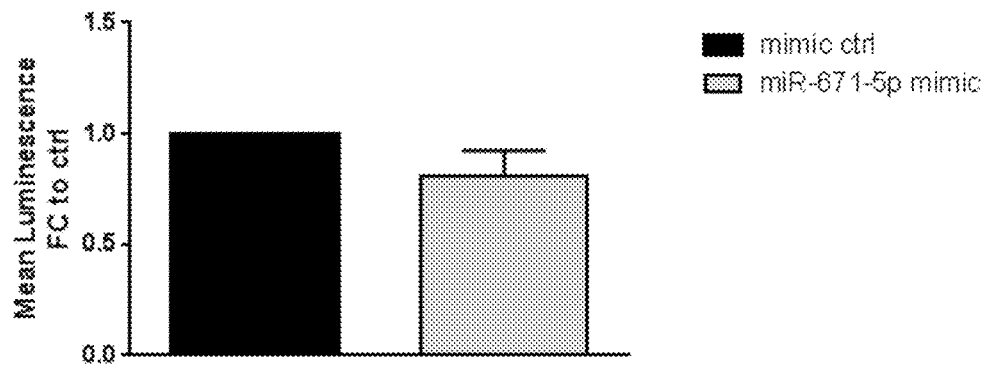
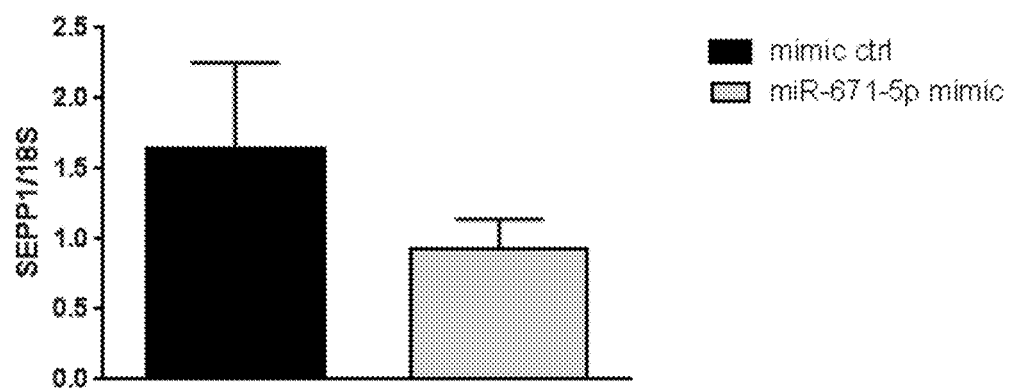

Figure 26
Probing the effect of Lycorine and Bufalin on liver and kidney injury
A
Liver injury
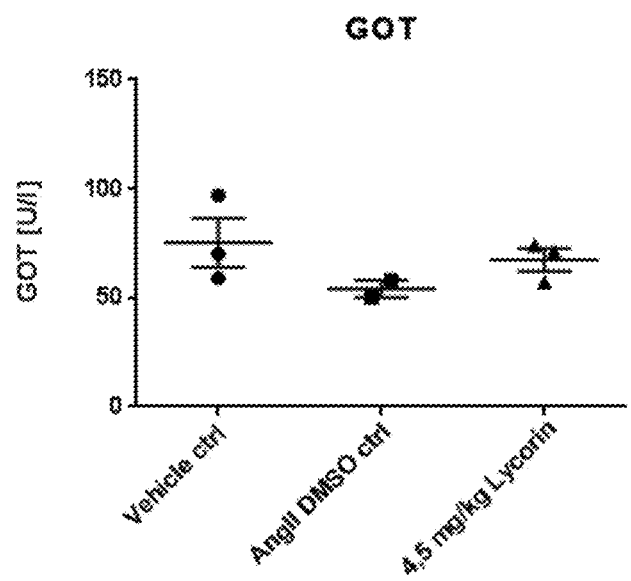
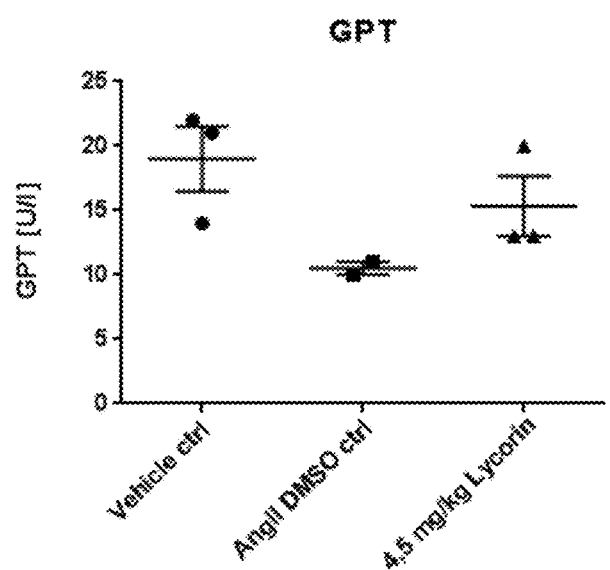

Figure 26 (cont.)
Probing the effect of Lycorine and Bufalin on liver and kidney injury
B
Liver injury
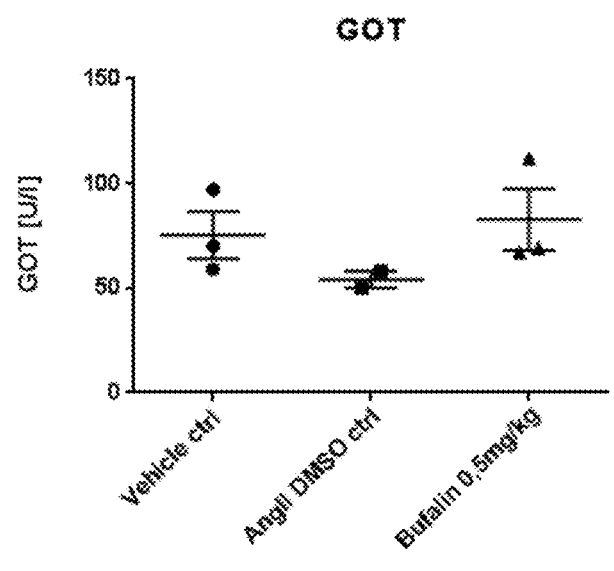
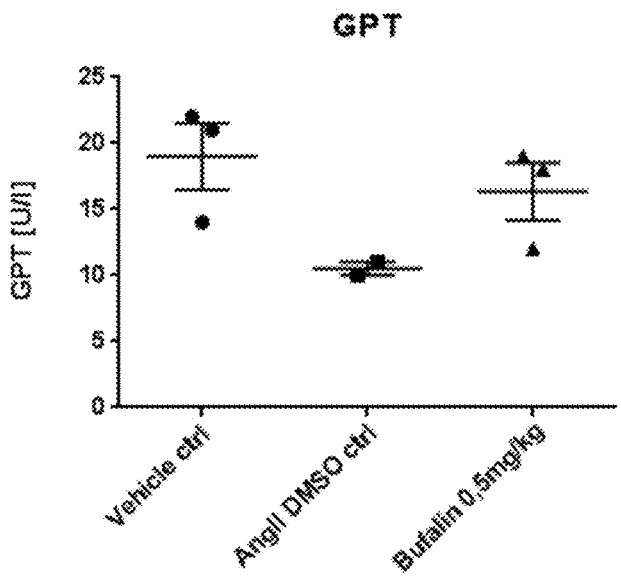

Figure 27
Probing the effect of Anisomycin and Gitoxigenin on liver and kidney injury
A
Liver injury
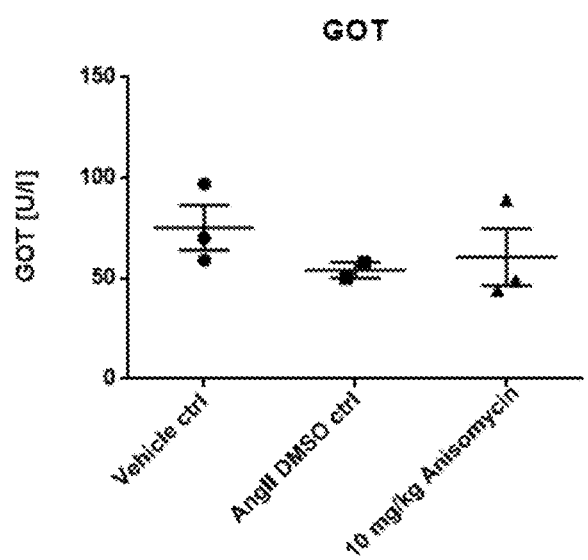
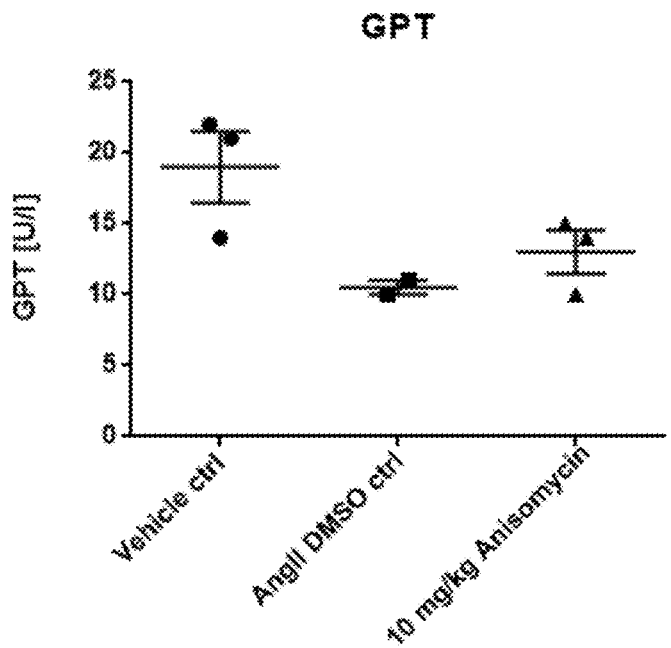

Figure 27 (cont.)
A Kidney injury
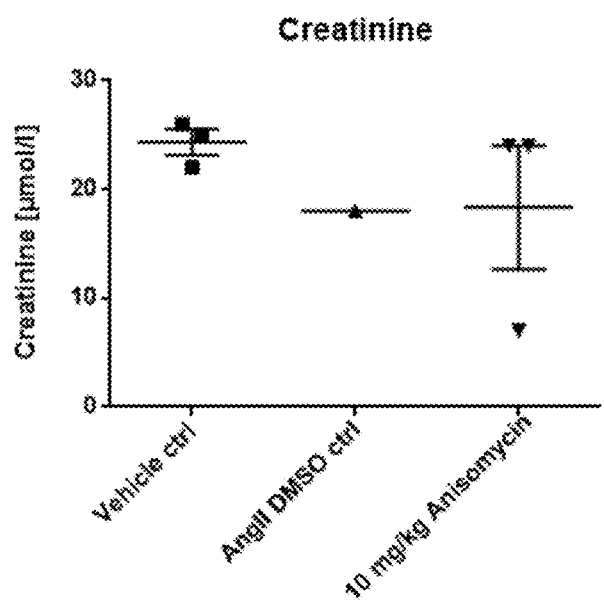
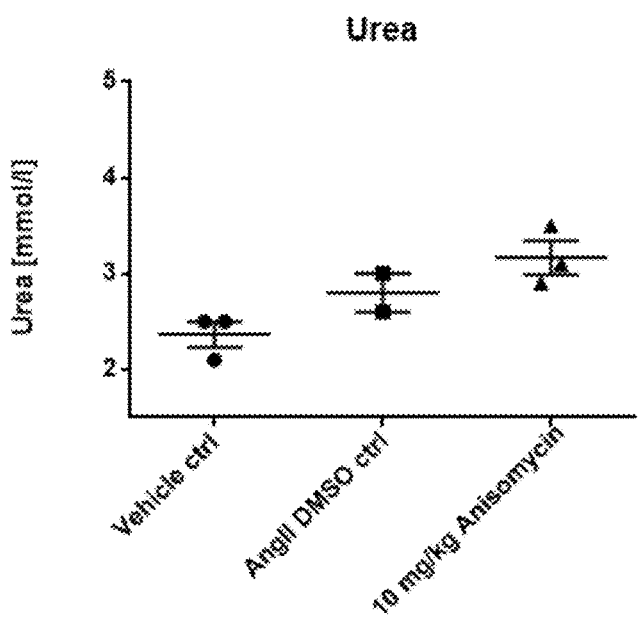

Figure 27 (cont.)
Probing the effect of Anisomycin and Gitoxigenin on liver and kidney injury
B
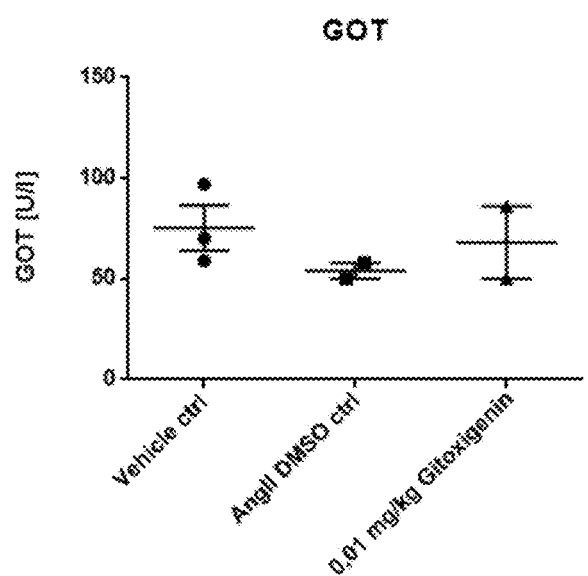
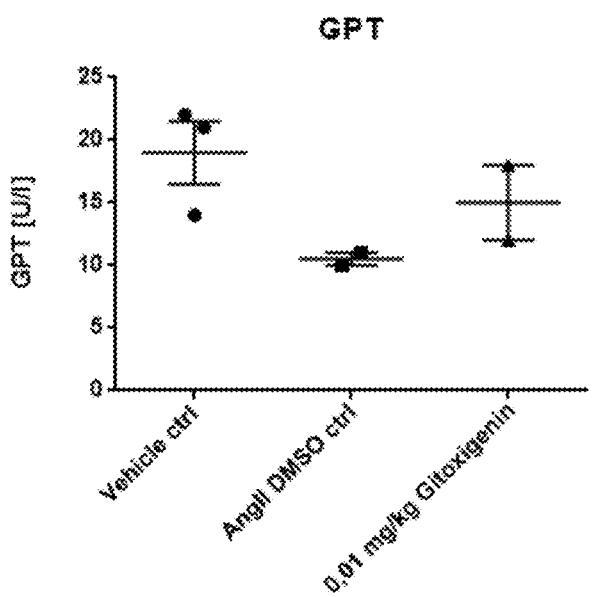

Figure 32
A
Bufalin structure:
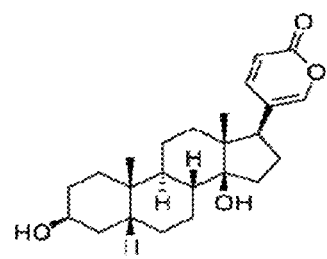
B
Bufalin analogs (BA):
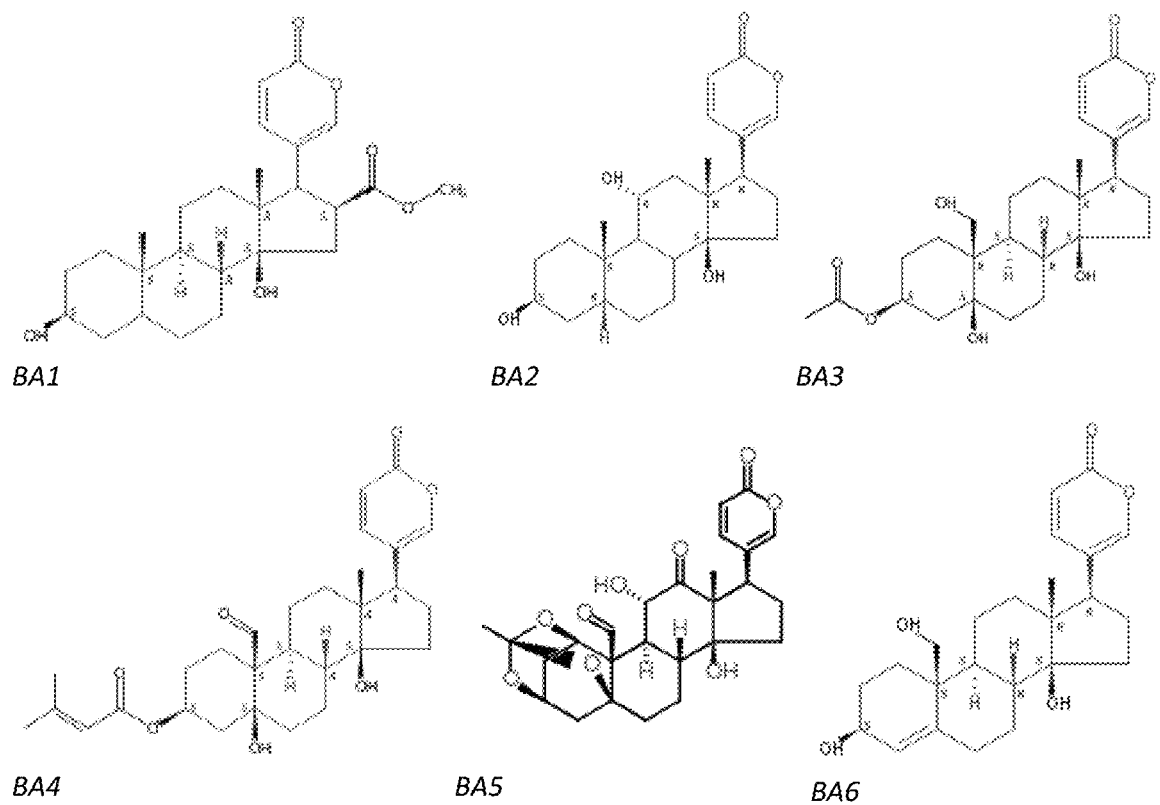
BA1  BA2  BA3
BA4  BA5  BA6

A Figure 33
Gitoxigenin structure:
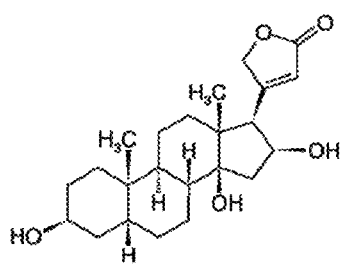
B
Gitoxigenin and Digitoxigenin analogs (GDA):
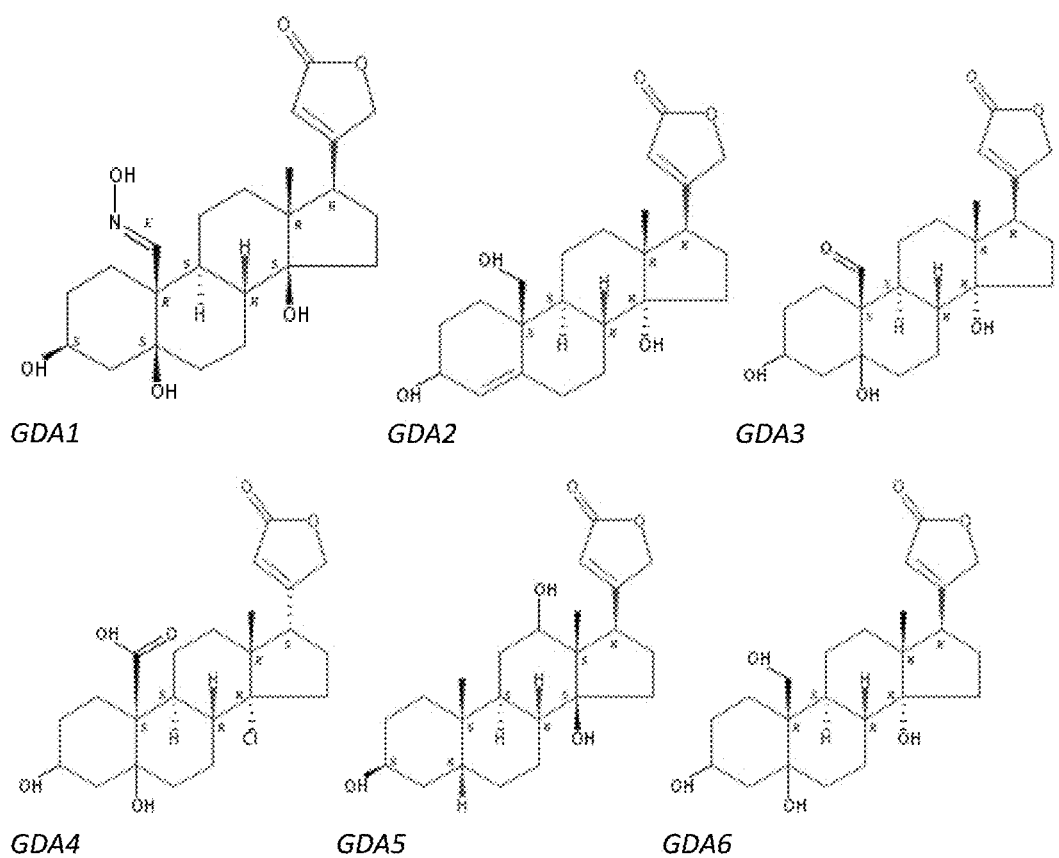

Figure 34
A
Lycorine structure:
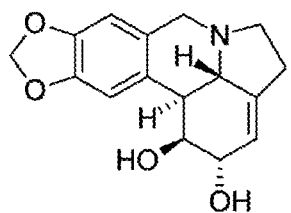
B
Lycorine analogs (LA):
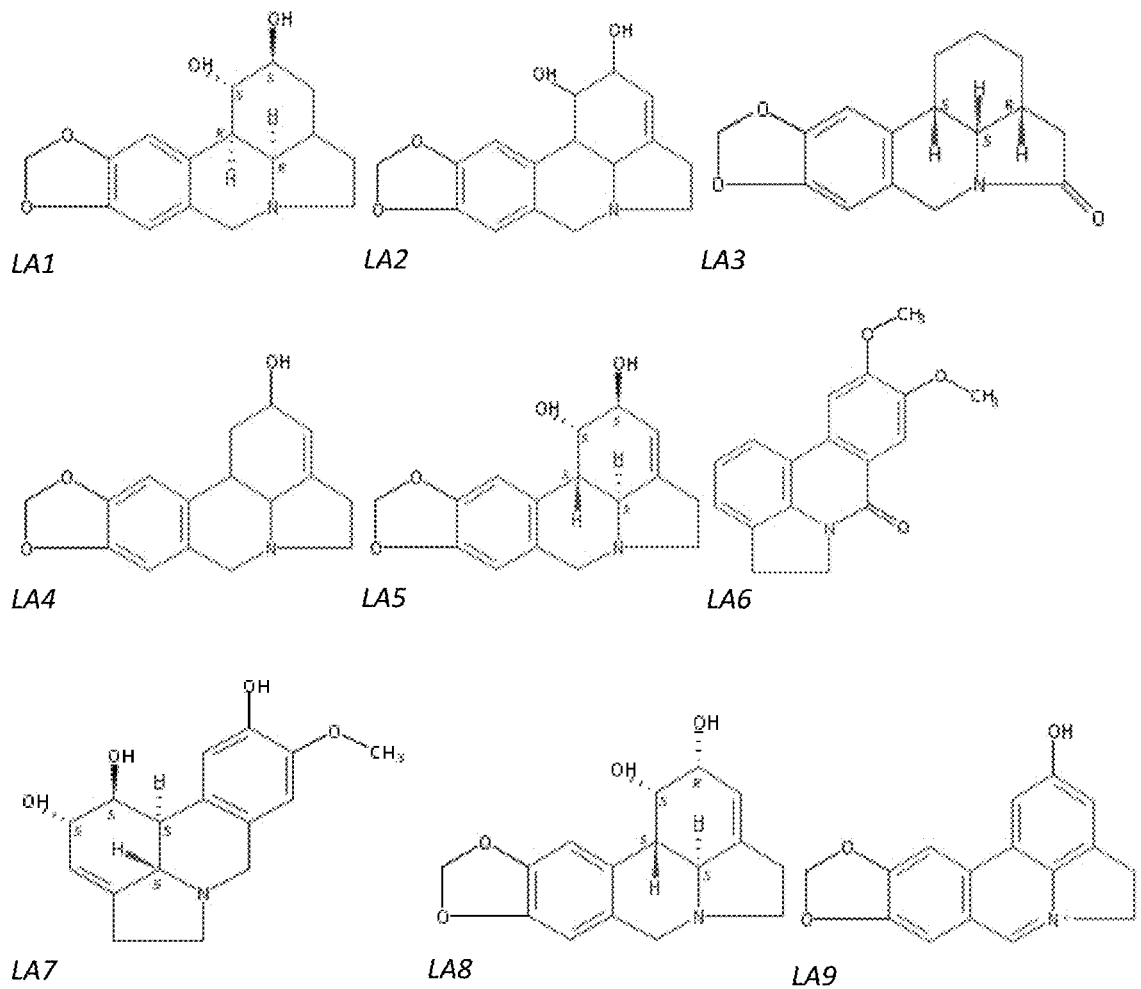
LA1　　　　LA2　　　　LA3
LA4　　　　LA5　　　　LA6
LA7　　　　LA8　　　　LA9

LA10  LA11  LA12

LA13  LA14

A    Figure 35
Anisomycin structure:
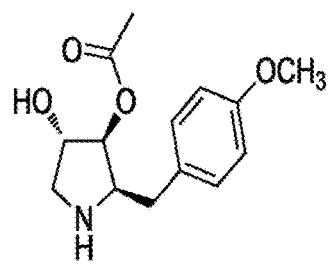
B
Anisomycin analogs (AA1):
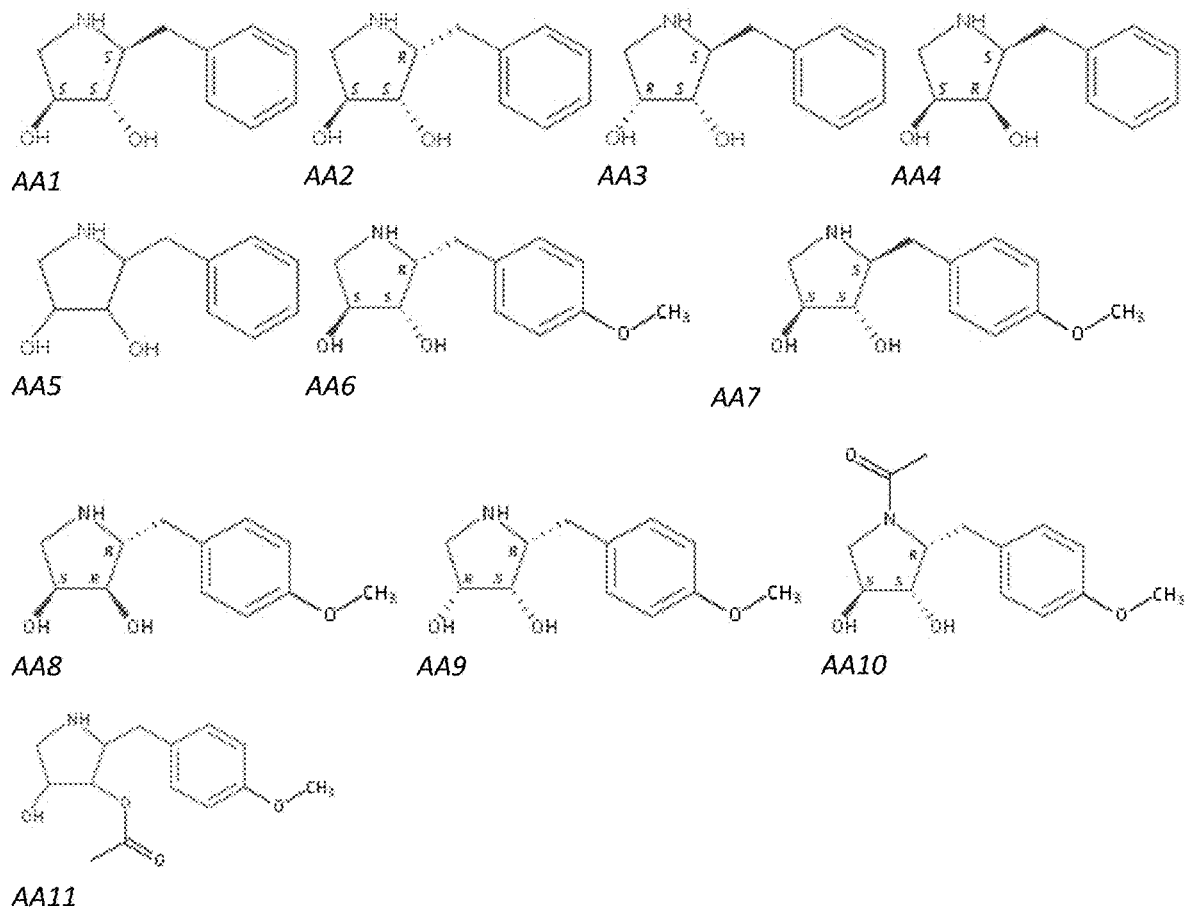

AA12

AA13

AA14

AA15

AA16

A            Figure 36
Geldanamycin structure:
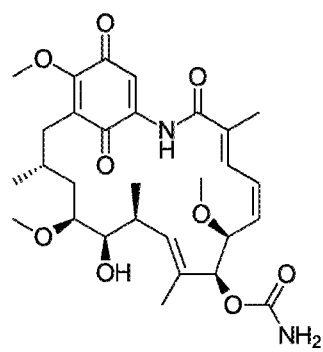
B
Geldanamycin analogs (GA):
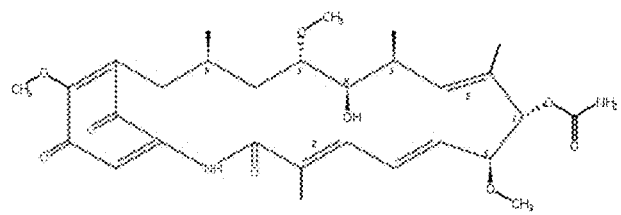
*GA1*
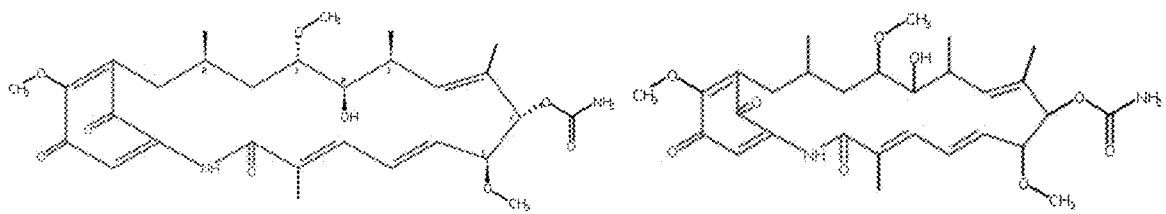
*GA2*                                        *GA3*
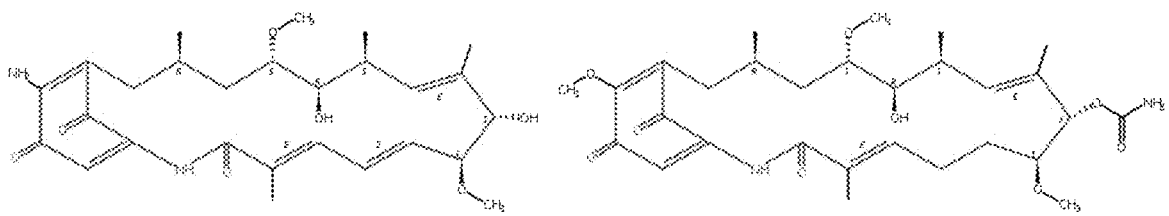
*GA4*              *GA5*

Figure 37
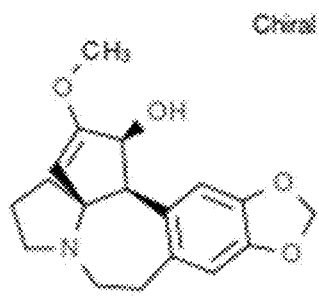
Cephalotaxine
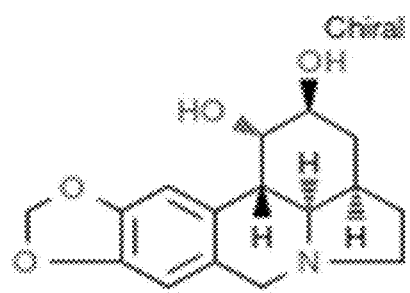
Dihydrolycorine
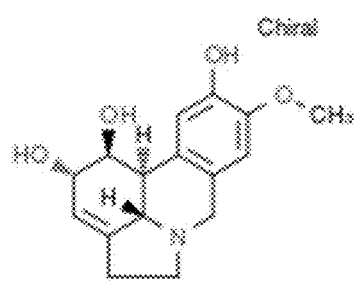
Pseudolycorine
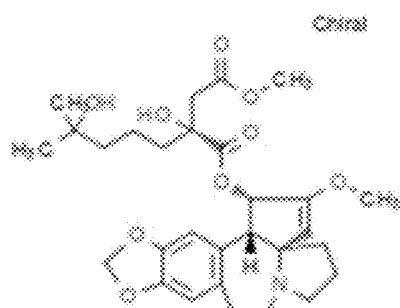
Homoharringtonine
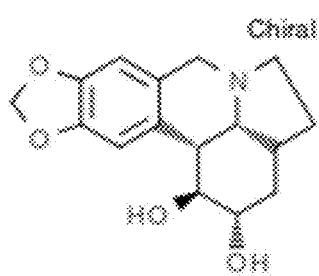
Lycobetaine
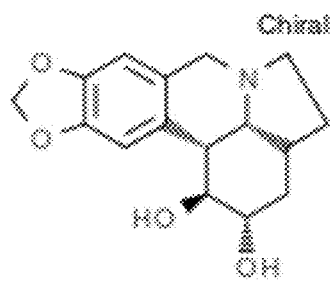
Amb24179473

Figure 37 (cont.)
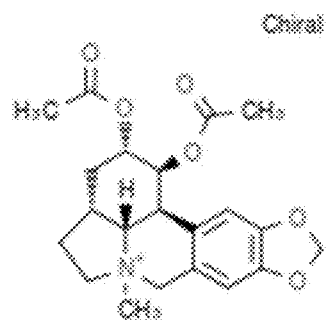
N-methyl-Nartazine
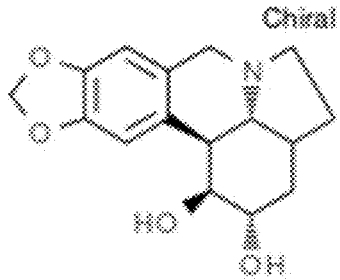
alpha-Dihydrolycorine
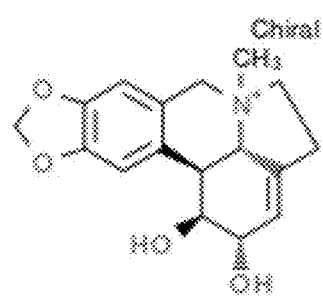
N-methyl-lycorine
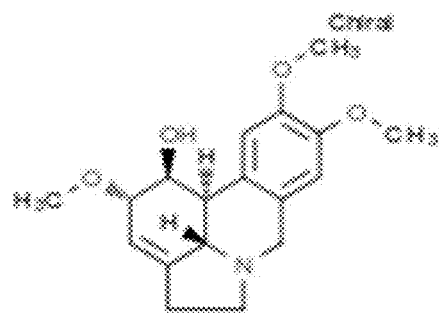
Galanthine
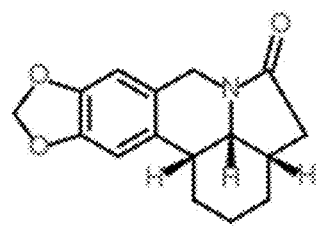
Amb24051775

Figure 38 (cont.)
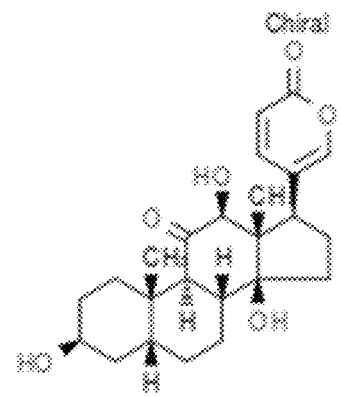
Bufarenogenin
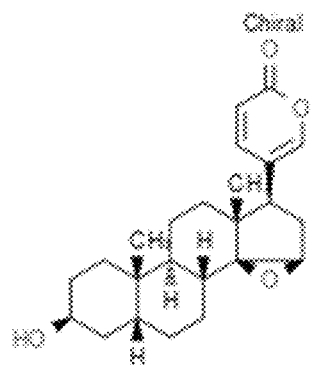
Bufogenin
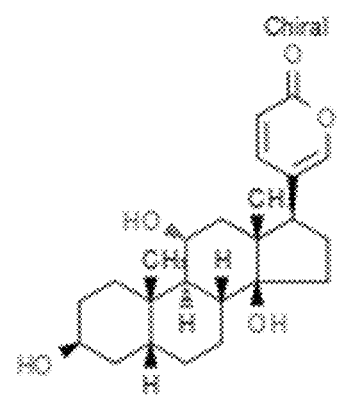
Gamabufotalin
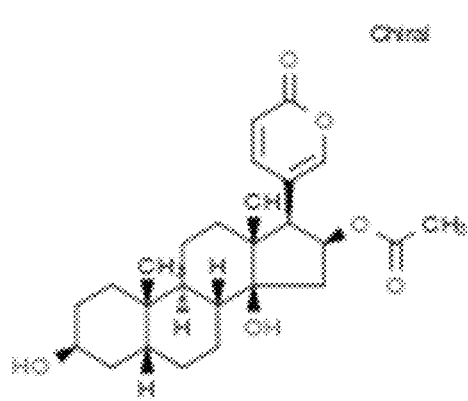
Bufotalin
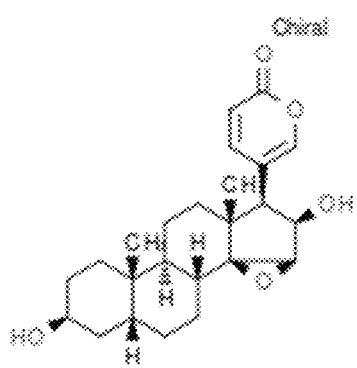
Deacetylcinobufagin

NATURAL COMPOUNDS AND FIBROSIS

CROSS-REFERENCE TO RELATED APPLICATIONS

This application is the U.S. national phase application filed under 35 U.S.C. § 371 claiming benefit to International Application No. PCT/EP2018/052096, filed on Jan. 29, 2018, which claims the benefit of priority of Luxembourg Patent Application No. LU100037, filed on Jan. 31, 2017. The entire contents of all of the above applications are hereby incorporated by reference.

FIELD OF THE INVENTION

The present invention relates to a compound for use in a method for preventing or treating fibrosis as well as a kit comprising the compound. The present invention also relates to an in vitro method for identifying a compound for preventing or treating fibrosis.

BACKGROUND

Fibrosis is the formation of excess fibrous connective tissue in an organ or tissue in a reparative or reactive process (Birbrair et al. 2014), which can destroy the architecture and function of the underlying organ or tissue. During fibrosis, a pathological accumulation of extracellular matrix (ECM) proteins occurs resulting in scarring and thickening of the affected tissue (Neary et al. 2015). Fibrosis can occur in many tissues within the body and is divided into organ-specific fibrosis, such as cardiac fibrosis, lung fibrosis or kidney fibrosis, and systemic fibrosis.

Basically, fibrosis can be considered an exaggerated wound healing response which interferes with normal organ function (Neary et al. 2015).

A normal wound-healing involves the three distinct phases of injury, inflammation and repair: During the first phase many agents, including environmental particles, allergens, infectious agents, chemotherapy and radiation are responsible for a disruption of epithelial and endothelial cells resulting in an anti-fibrinolytic cascade. Next, the phase of inflammation is initiated by circulating inflammatory cells and fibrocytes, which are recruited to the site of injury through chemokine gradients, supplying fibroblast-activating cytokines and growth factors. Neovascularization provides access to damaged areas and a steady stream of inflammatory, anti-inflammatory and phagocytic cells. The last phase of repair includes the fibroblasts contracting and decreasing the size of the wound. In the last phase, inflammatory cells undergo apoptosis, terminating collagen deposition and are cleared by phagocytic cells. Epithelial and endothelial cells are replaced and tissue architecture is restored.

For successful wound healing as described above, a regulated response is maintained through negative feedback loops and a balance of regenerative processes. Normal healing can be converted into a fibrotic cascade due to imbalances in the healing process, such as an excessive inflammation and the production of inflammatory and fibroblast-activating cytokines. The recruitment of fibroblasts and increased frequency of α-SMA+ cells at the site of injury can result in too much collagen deposition, which in turn leads to fibrosis. There is thus a need in the art to slow down the progression of fibrosis (Wilson and Wynn 2009).

As mentioned above, one example of fibrosis is cardiac fibrosis (CF) which is involved in heart failure (HF), which in turn is among the leading causes of death in the industrialized countries. Cardiac fibrosis is characterized by an increase in proliferation rates of resident cardiac fibroblasts in the cardiac muscle, excessive matrix deposition, including collagen deposition, or both. Normally, fibroblasts secrete collagen, but if this process is over-activated it may cause abnormal thickening and loss of flexibility of the cardiac muscle. This leads to a destruction of physiological tissue architecture and progressive organ dysfunction, ultimately resulting in heart failure (Thum 2014). As CF correlates with a higher long-term mortality and persists in patients even when medicated following the official guidelines for HF treatment, it is indispensable to apply a treatment focusing on anti-fibrotic therapeutic strategies in addition to treating or preventing heart failure.

One of the most common histological features of the heart failure is myocardial fibrosis, a specific fibrosis with various pathophysiological mechanisms. Myocardial fibrosis is a complex process that involves each cellular component of the myocardial tissue. The fibrillar collagen network is in intimate contact with all the different cell-types of the myocardium and plays a critical role in the maintenance of ventricular shape, size and function. Myocardial fibroblasts increase the production of collagen and other extracellular matrix components resulting in ventricular systolic function, abnormal cardiac remodeling and increased ventricular stiffness Thus, myocardial fibrosis is defined by a significant increase in the collagen volume fraction (CVF) of myocardial tissue (Nathan et al. 2011).

Fibrosis in general can be considered an important cause of morbidity and mortality worldwide and there are currently no acceptable treatments for this particular disease (O'Reilly 2016). MicroRNAs (short: miRNAs) may be associated with various types of fibrosis and may be useful as disease-specific biomarkers. In addition, miRNAs are known as powerful regulators of posttranscriptional gene expression which play an important role in pathophysiological processes. MiRNAs have been studied since they were discovered more than two decades ago. MiRNAs are small, non-coding RNAs that mediate mRNA cleavage, translational repression or mRNA destabilization by partial complementary binding to the 3' untranslated region in target transcription. Further, miRNAs are small single strand RNAs highly conserved during the evolution and their length is generally around 22-25 nucleotides (O'Reilly 2016). Compared to small interfering RNA (siRNA), miRNA mediate their effects preferably through imperfect base pairing with sequences in the 3' untranslated region (UTR) of the targeted mRNA. This particular region in the miRNA which is important for repression of the target mRNA is called "seed region". Due to the imperfect binding of miRNAs to their target, one miRNA can regulate many genes. Specifically, miRNAs are transcribed by RNA polymerase II as part of capped and polyadenylated primary transcripts (pri-miRNAs) that can be either protein-coding or non-coding. Further, the primary transcript is cleaved by the Drosha ribonuclease III enzyme to produce an approximately 70-nt stem-loop precursor miRNA (pre-miRNA), which is further cleaved by the cytoplasmic Dicer ribonuclease to generate the mature miRNA and antisense miRNA star (miRNA*) products. The mature miRNA is incorporated into a RNA-induced silencing complex (RISC), which recognizes target mRNAs through imperfect base pairing with the miRNA and most commonly results in translational inhibition or destabilization of the target mRNA. Thus, targeting a specific miRNA can result in normalizing a wide range of deregulated genes, e.g. involved in cardiac fibrosis.

In particular, miRNAs are quantitatively modified in particular diseases entities such as cardiovascular disease, especially in the field of heart failure (Schulte et al. 2015) or have been implicated in the progression of liver fibrosis (Murakami et al. 2012). Further, miRNAs have emerged as a major area of biomedical research as markers for pulmonary fibrosis (Rajasekaran et al. 2015). Additionally, studies have shown that certain specific miRNAs are differentially expressed in cardiac fibrosis (Wang et al. 2012). However, despite the known differential expression of miRNAs in the literature, no specific compounds for inhibition of miRNAs are known.

Since therapeutic treatments for fibrosis are currently not known (O'Reilly 2016), it is of extreme importance to develop new pharmaceutical compounds for fibrosis, in particular cardiac fibrosis.

SUMMARY OF THE INVENTION

The object of the present invention is to provide a compound for use in a method of preventing or treating fibrosis.

Specifically, it was found that specific miRNAs are upregulated in fibrosis. One of these miRNAs is miR-671-5p. The inhibition of miR-671-5p is a promising starting point for the treatment of fibrosis, in particular cardiac fibrosis.

The present invention thus encompasses an inhibitor of miR-671-5p for use in a method of preventing or treating fibrosis.

The inhibitor can be selected from the group consisting of Lycorine, Bufalin, Gitoxigenin, Anisomycin and Geldanamycin, as well as salts, analogs and derivatives thereof.

The present invention further provides said inhibitor for use in the treatment or prevention of fibrosis, wherein fibrosis can be selected from cardiac fibrosis, lung fibrosis, liver fibrosis, kidney fibrosis, gastrointestinal fibrosis, skeletal muscle fibrosis, systemic sclerosis, multifocal fibrosclerosis, sclerodermatous graft-versus-host disease (GVHD) in bone marrow transplantation recipients, nephrogenic systemic fibrosis or dermal fibrosis. In a preferred embodiment, the fibrosis is cardiac fibrosis, lung fibrosis or kidney fibrosis.

The invention also encompasses said inhibitor for use in a method of preventing or treating fibrosis, wherein said use comprises administering the inhibitor every other day for a time period of two weeks, three weeks, four weeks, five weeks or longer, preferably for two consecutive weeks.

In addition, the present invention provides for the administration of the inhibitor by injections or by infusions.

The administration of the inhibitor can be performed intraperitoneally, intravenously, subcutaneously, intramuscularly or orally.

Also described is a kit comprising said inhibitor of miR-671-5p.

The present invention further provides an in vitro method for identifying a compound for preventing or treating fibrosis comprising: a) measuring the amount of miR-671-5p in cells undergoing fibrosis; b) contacting the cells undergoing fibrosis with a test compound; and c) comparing the amount of miR-671-5p in said fibrotic cells after step b) with the amount of miR-671-5p measured in step a); and d) wherein a decrease in miR-671-5p levels indicates that the test compound is a compound for preventing or treating fibrosis.

The present invention contemplates said in vitro method, wherein the amount of the test compound per administration is at least 0.5 µM, 1 µM, 2 µM, 3 µM, 4 µM, 5 µM, 6 µM, 7 µM, 8 µM, 9 µM, or at least 10 µM.

The invention also provides said in vitro method, wherein the compound is a natural compound, a synthetic compound or a hemisynthetic compound.

The invention further contemplates said in vitro method, wherein the test compound is selected from the group consisting of Lycorine, Bufalin, Gitoxigenin, Anisomycin and Geldanamycin, as well as salts, analogs and derivatives thereof.

Additionally, said in vitro method is provided, wherein fibrosis can be selected from cardiac fibrosis, lung fibrosis, liver fibrosis, kidney fibrosis, gastrointestinal fibrosis, skeletal muscle fibrosis, systemic sclerosis, multifocal fibrosclerosis, sclerodermatous graft-versus-host disease (GVHD) in bone marrow transplantation recipients, nephrogenic systemic fibrosis or dermal fibrosis.

The present invention encompasses said in vitro method, wherein the cells undergoing fibrosis are cardiac cells, lung cells, liver cells, kidney cells, intestinal cells, skeletal muscle cells or dermal cells. In a preferred embodiment, the cells undergoing fibrosis are human cardiac fibroblasts (HCFs), pulmonary fibroblasts or renal fibroblasts.

Functional screen of 480 nature-derived substances in vitro in primary human cardiac fibroblasts (HCFs) uncovers compounds inhibiting proliferation of HCFs. Dose-dependent inhibitory effects of Bufalin, Gitoxigenin, Lycorine, Anisomycin and Geldanamycin on proliferation of primary HCFs. This is described in Example 1.

Figure 2:
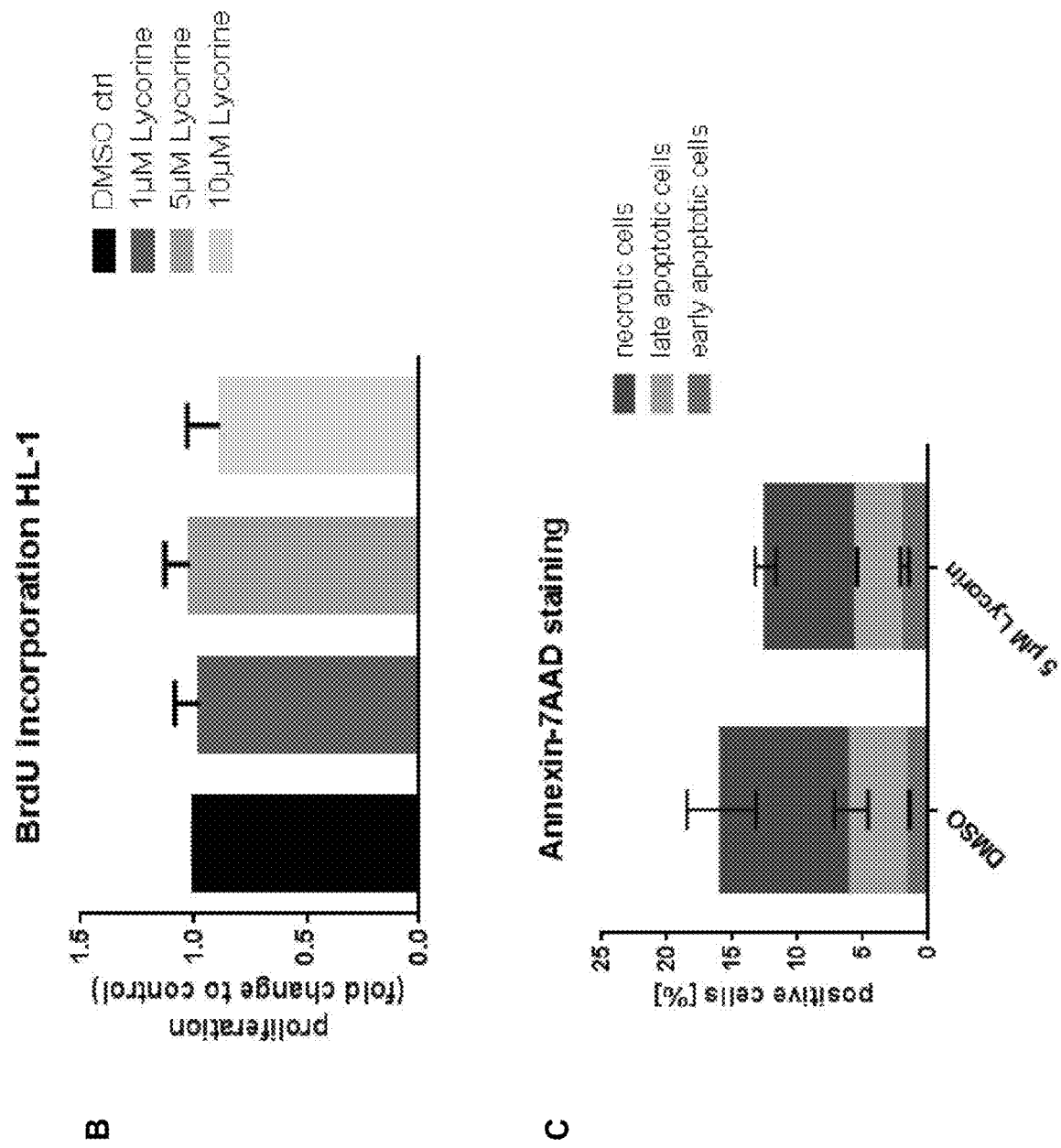
Figure 2:
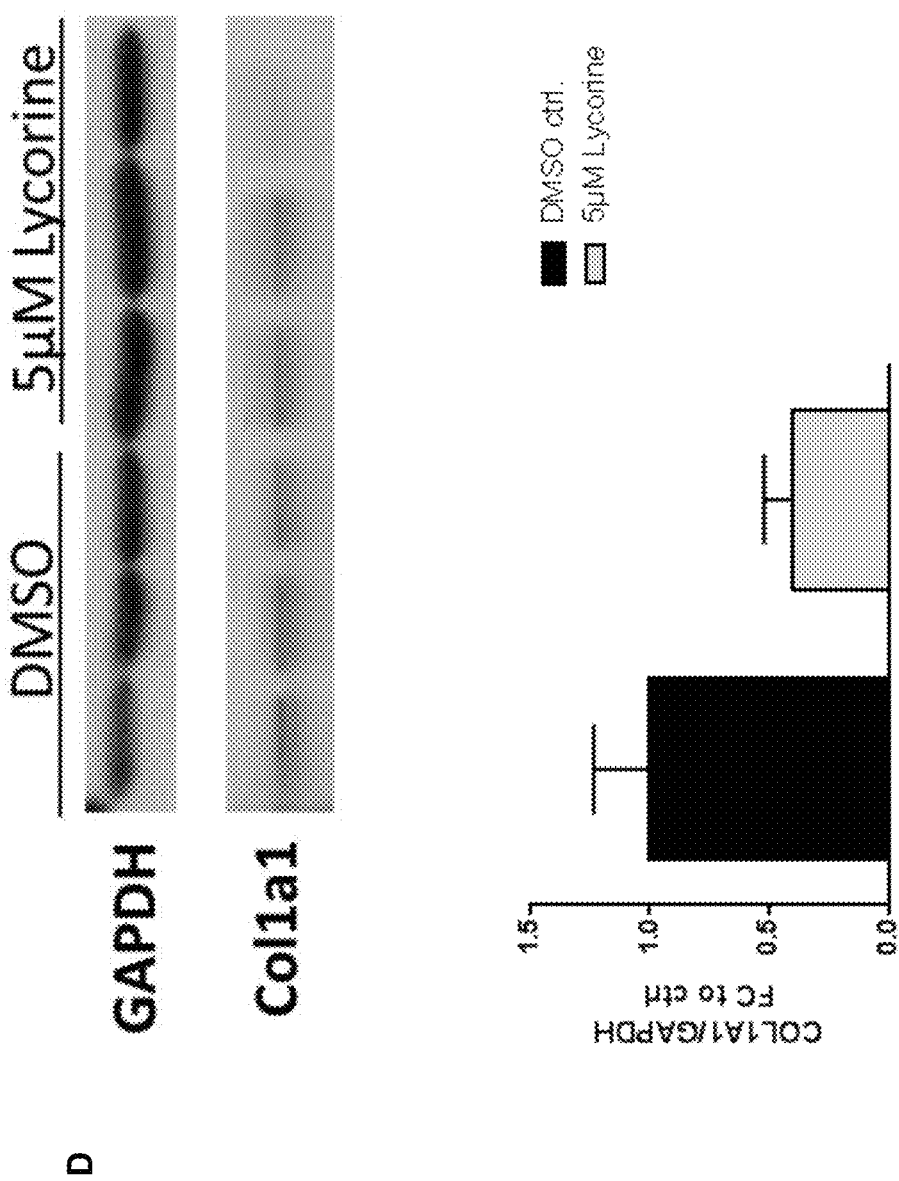

FIG. 2: In vitro testing of Lycorine.

Anti-fibrotic Lycorine potently and specifically acts on HCFs in vitro: A) Schematic view of the chemical structure of the alkaloid Lycorine and picture of a member of the amaryllis species producing Lycorine. B) Dose-dependent (1 µM, 5 µM and 10 µM) inhibitory effects of Lycorine on proliferation of primary HCFs are fibroblast-specific as evidenced by no impact of the same concentrations of Lycorine on proliferation of the cardiomyocyte cell line HL-1 measured via BrdU-ELISA, DMSO refers as control. C) Lycorine does not induce cell death in primary HCFs after Annexin-7AAD-staining. D) Lycorine decreases expression levels of the extracellular matrix component Collagen1a1 in primary HCFs as shown in a representative Western Blot (normalized to GAPDH), DMSO refers as control. Data are depicted as the average of 3 independent measurements performed in triplicates and represented as mean±SEM. *$P<0.05$; $P<0.01$; *$P<0.001$; ****$P<0.0001$. This is described in Example 2.

Figure 3:
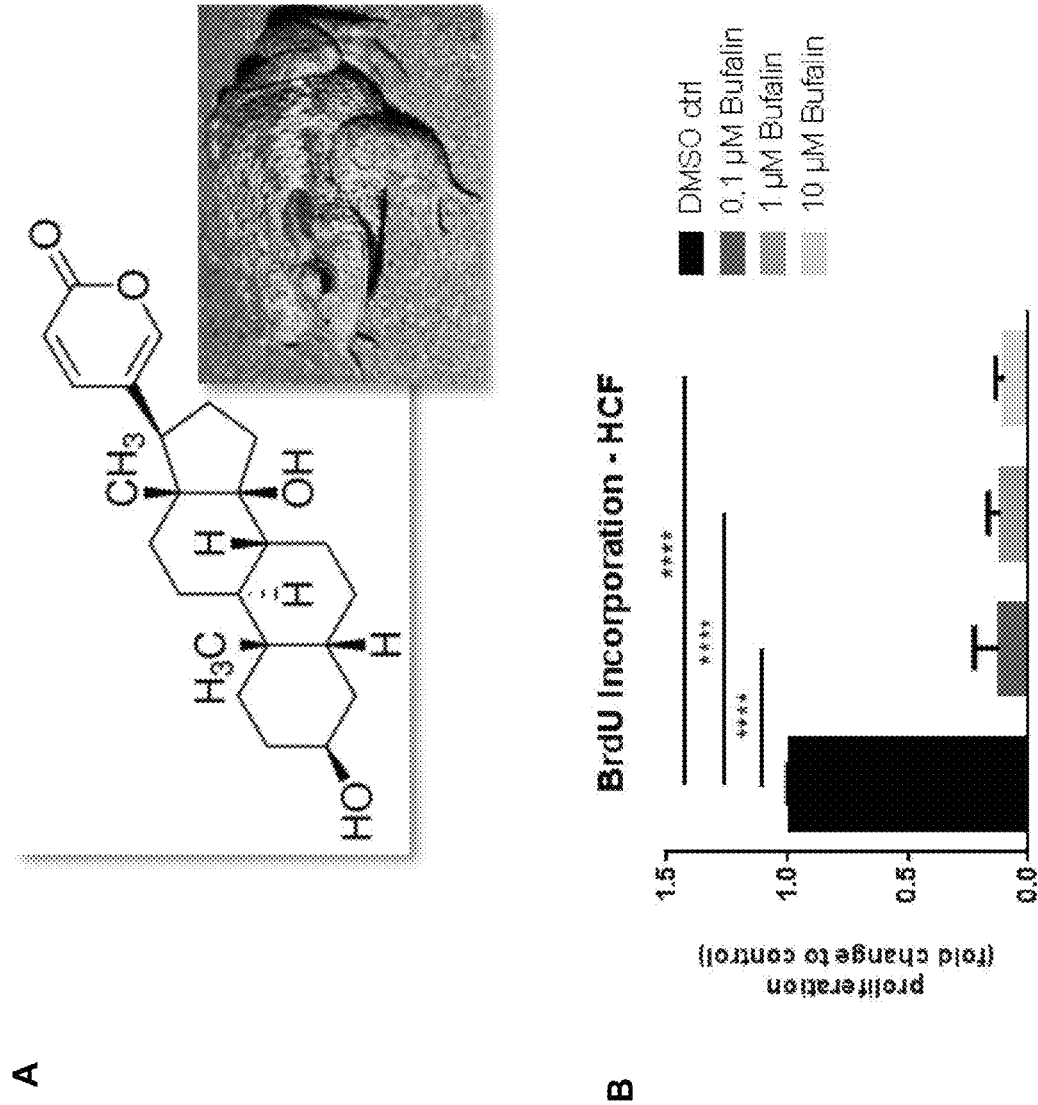
Figure 3:
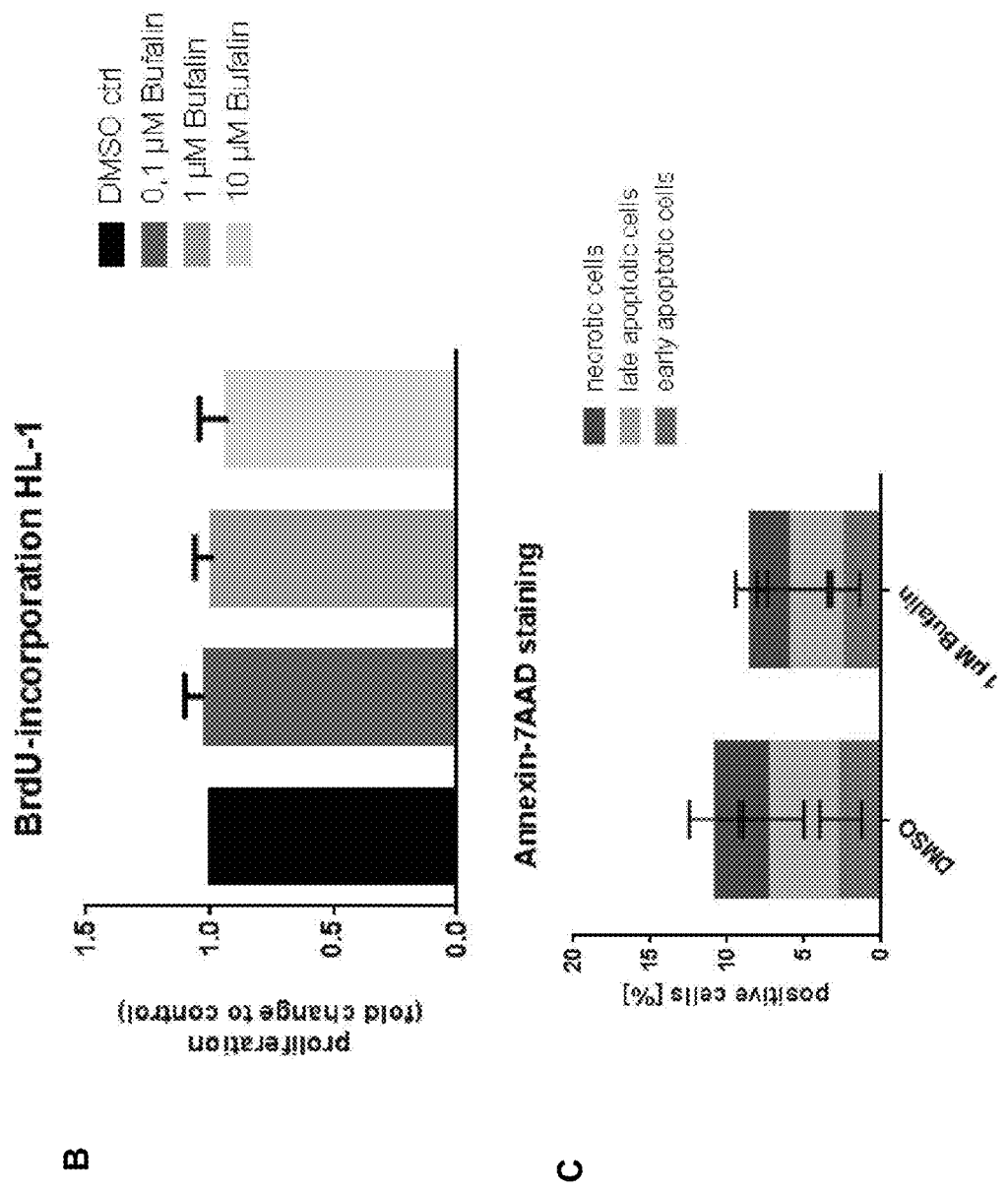
Figure 3:
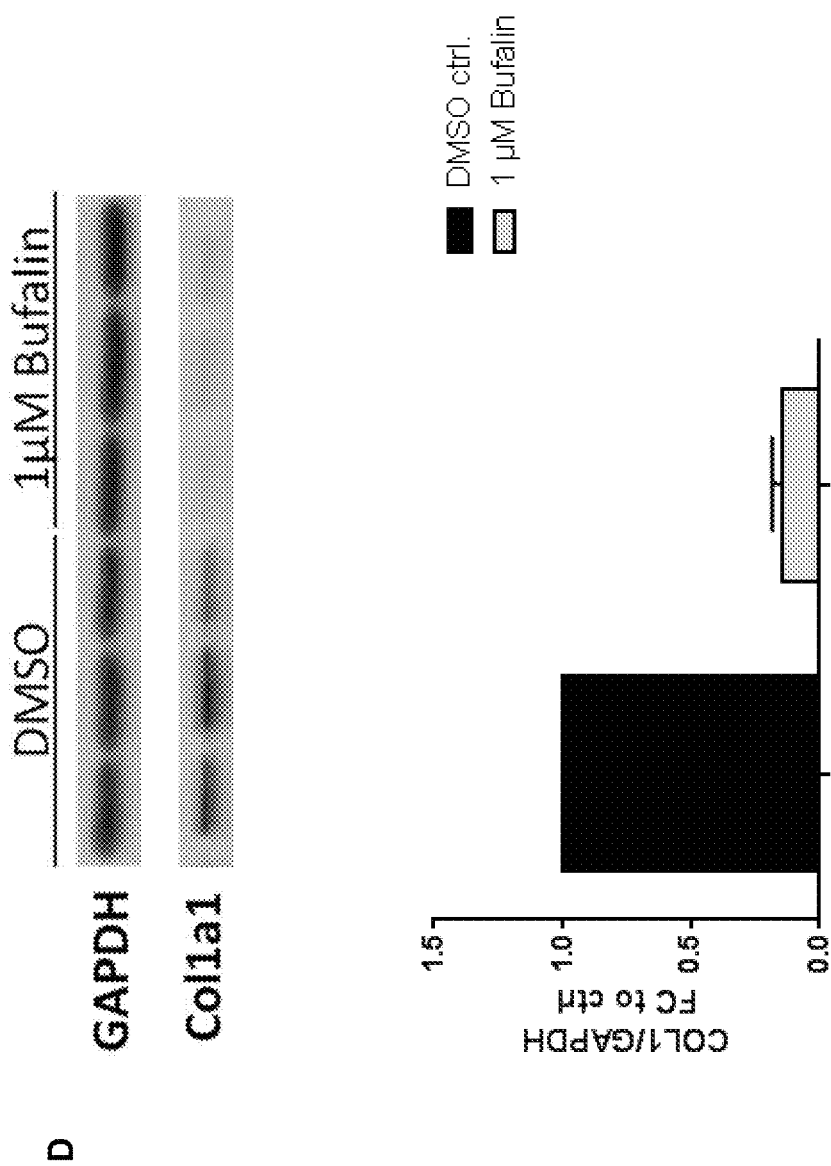

FIG. 3: In vitro testing of Bufalin.

Anti-fibrotic Bufalin potently and specifically acts on HCFs in vitro: A) Schematic view of the chemical structure of the cardiac glycoside Bufalin and picture of a toad producing Bufalin. B) Dose-dependent (0.1 µM, 1 µM and 10 µM) inhibitory effects of Bufalin on proliferation of primary HCFs are fibroblast-specific as evidenced by no impact of the same concentrations of Bufalin on proliferation of the cardiomyocyte cell line HL-1 measured via BrdU-ELISA, DMSO refers as control. C) Bufalin does not induce cell death in primary HCFs after Annexin-7AAD-staining. D) Bufalin decreases expression levels of the extracellular matrix component Collagen1a1 in primary HCFs as shown in a representative Western Blot (normalized to GAPDH), DMSO refers as control. Data are depicted as the average of 3 independent measurements performed in triplicates and represented as mean±SEM. *P<0.05; P<0.01; *P<0.001; ****P<0.0001. This is described in Example 2.

Figure 4:
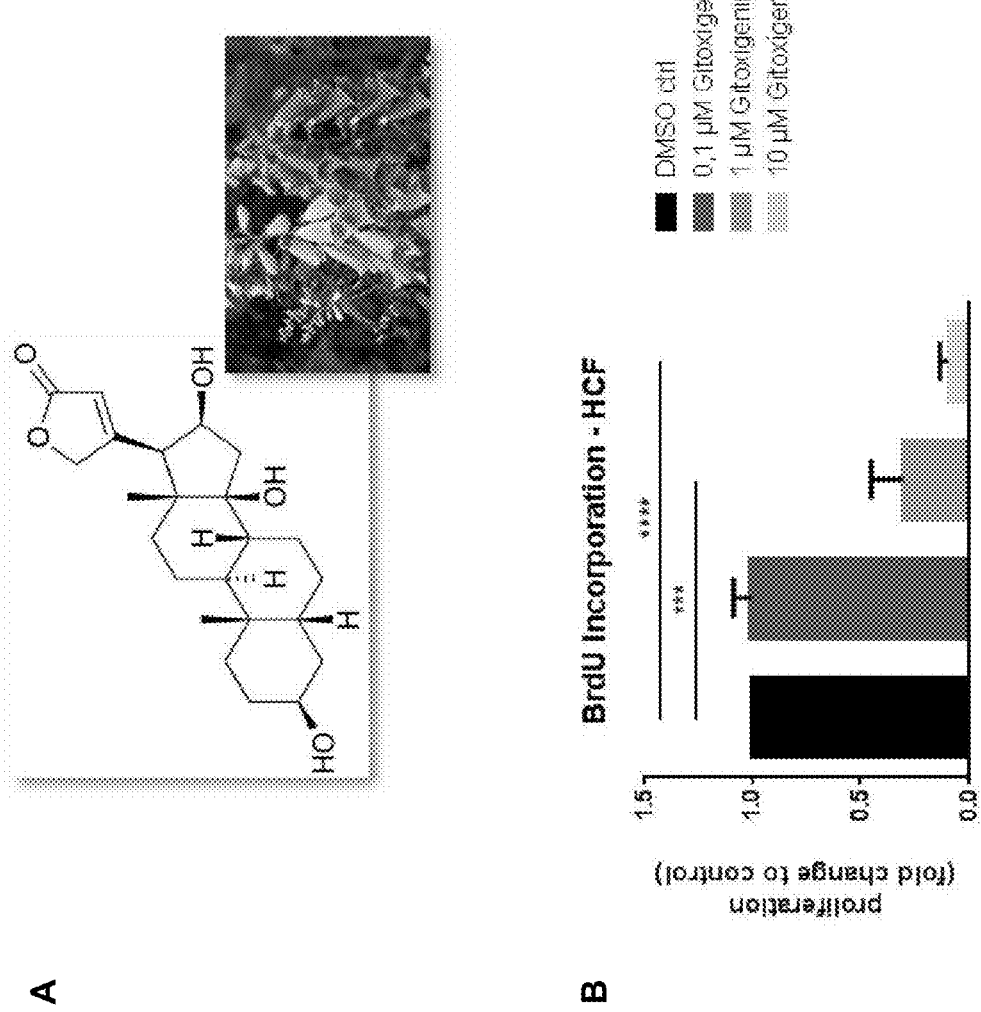
Figure 4:
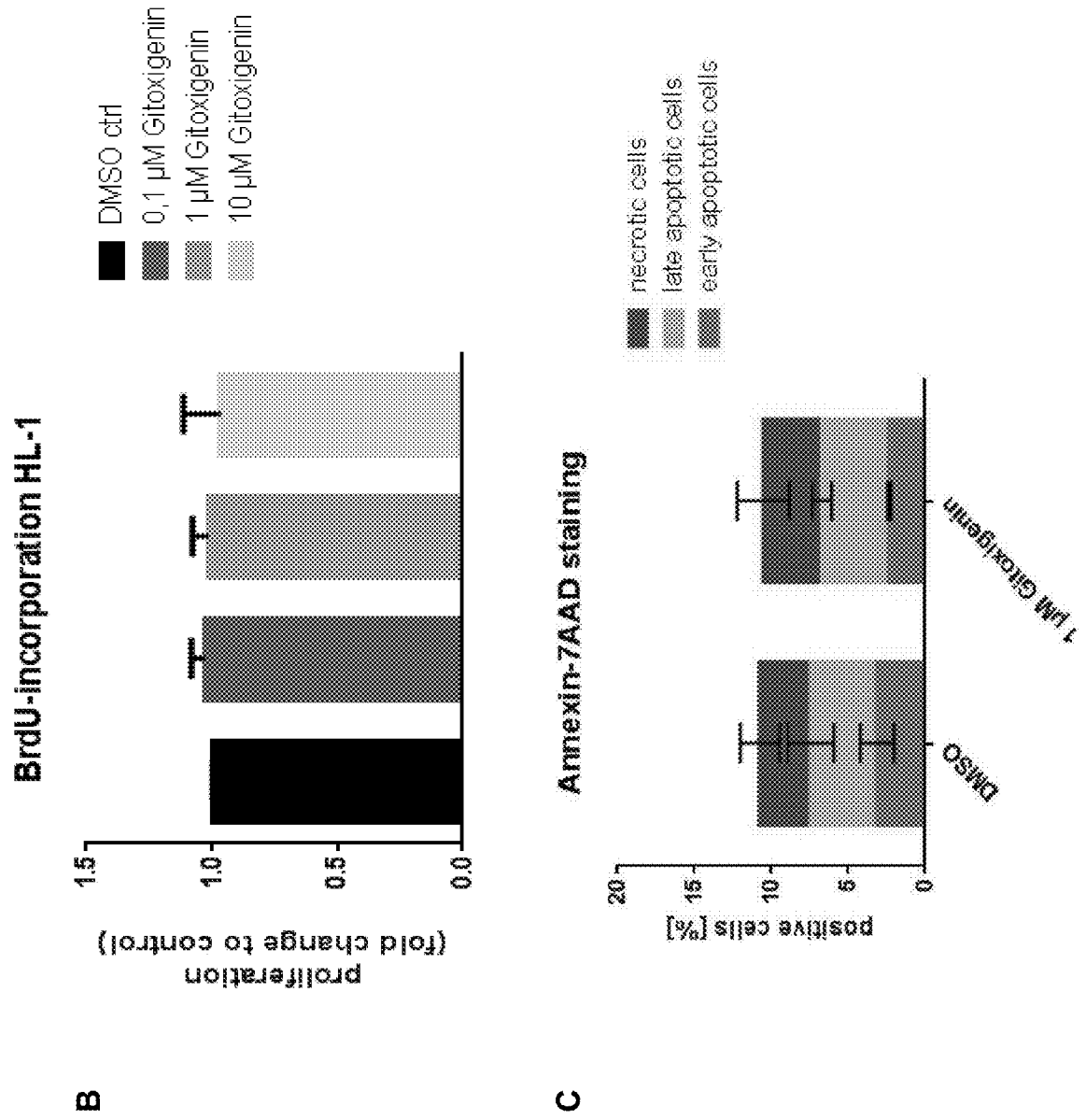
Figure 4:
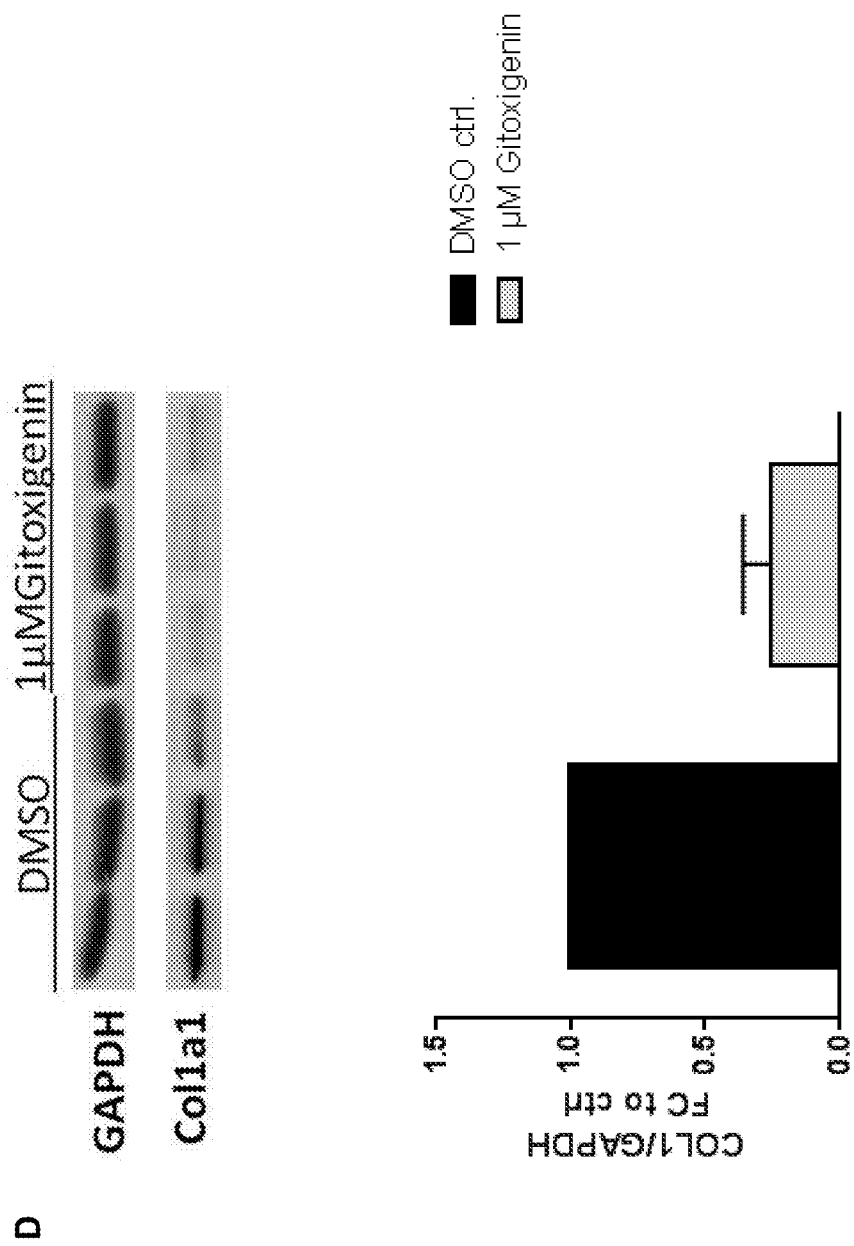

FIG. 4: In vitro testing of Gitoxigenin.

Anti-fibrotic Gitoxigenin potently and specifically acts on HCFs in vitro: A) Schematic view of the chemical structure of the cardiac glycoside Gitoxigenin and picture of a *digitalis* producing Gitoxigenin. B) Dose-dependent (0.1 µM, 1 µM and 10 µM) inhibitory effects of *digitalis* producing Gitoxigenin on proliferation of primary HCFs are fibroblast-specific as evidenced by no impact of the same concentrations of Gitoxigenin on proliferation of the cardiomyocyte cell line HL-1 measured via BrdU-ELISA, DMSO refers as control. C) Gitoxigenin does not induce cell death in primary HCFs after Annexin-7AAD-staining. D) Gitoxigenin decreases expression levels of the extracellular matrix component Collagen1a1 in primary HCFs as shown in a representative Western Blot (normalized to GAPDH), DMSO refers as control. Data are depicted as the average of 3 independent measurements performed in triplicates and represented as mean±SEM. *P<0.05; P<0.01; *P<0.001; ****P<0.0001. This is described in Example 2.

Figure 5:
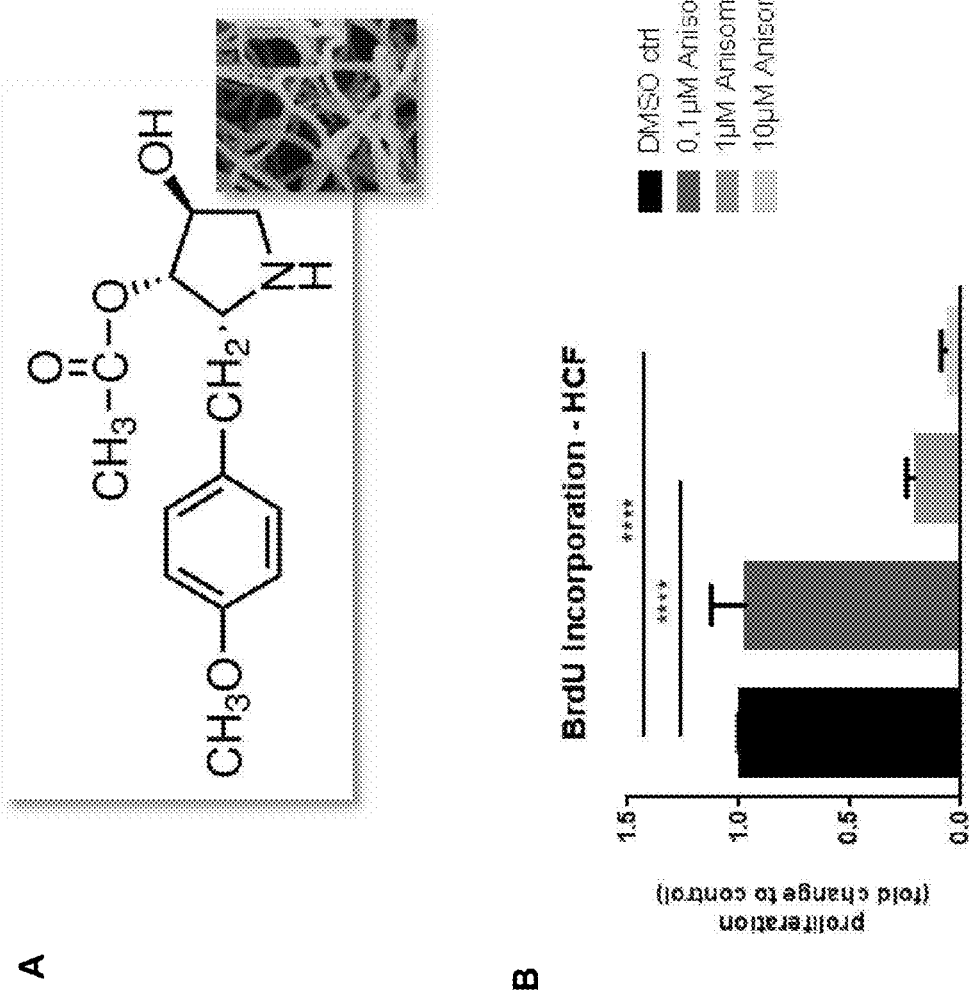
Figure 5:
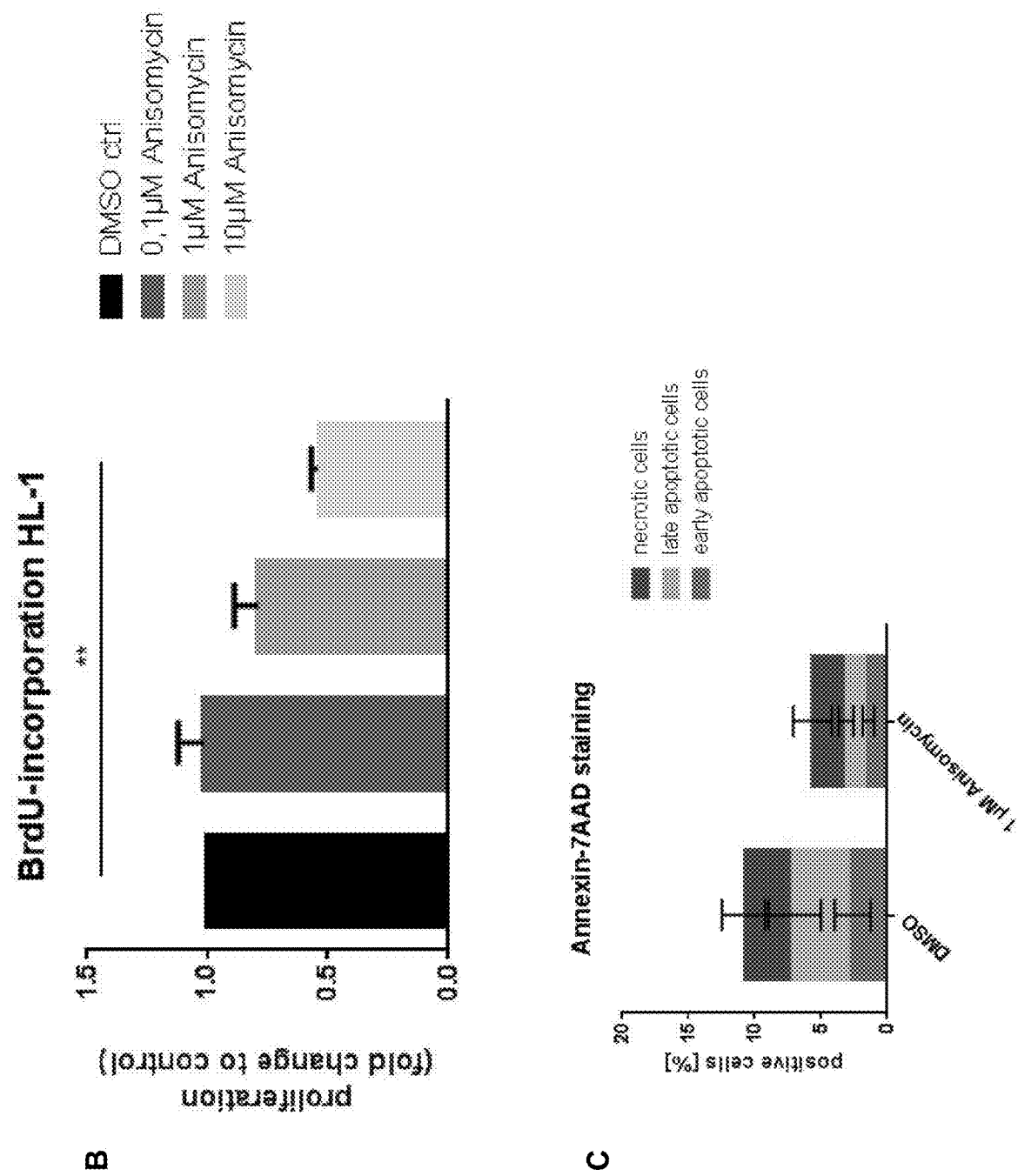
Figure 5:
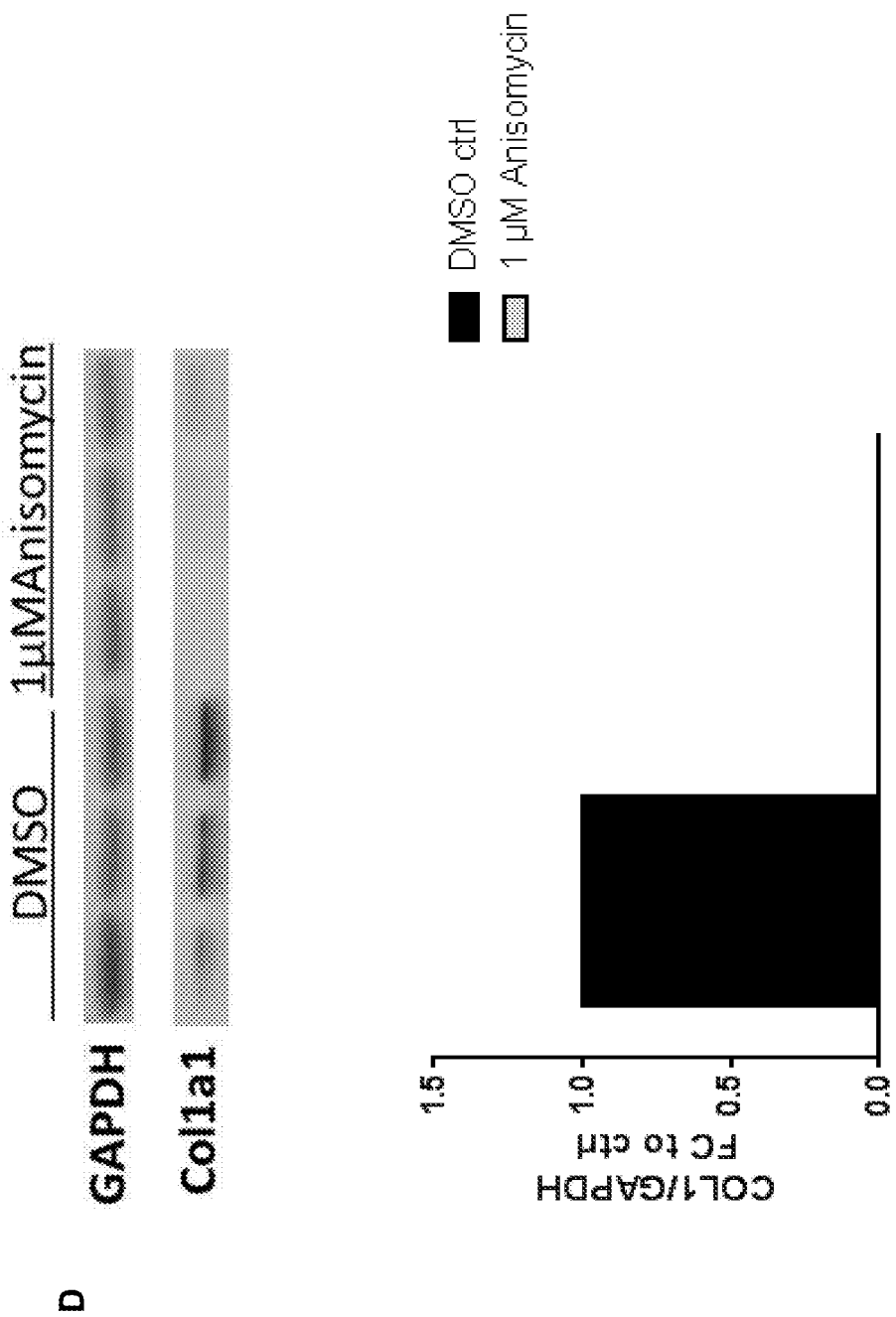

FIG. 5: In vitro testing of Anisomycin.

Anti-fibrotic Anisomycin potently and specifically acts on HCFs in vitro: A) Schematic view of the chemical structure of the cardiac glycoside Anisomycin and picture of *Streptomyces griseolus* producing Anisomycin. B) Dose-dependent (0.1 µM, 1 µM and 10 µM) inhibitory effects of *digitalis* producing Anisomycin on proliferation of primary HCFs are fibroblast-specific as evidenced by no impact of the same concentrations of Anisomycin on proliferation of the cardiomyocyte cell line HL-1 measured via BrdU-ELISA, DMSO refers as control. C) Anisomycin does not induce cell death in primary HCFs after Annexin-7AAD-staining. D) Anisomycin decreases expression levels of the extracellular matrix component Collagen1a1 in primary HCFs as shown in a representative Western Blot (normalized to GAPDH), DMSO refers as control. Data are depicted as the average of 3 independent measurements performed in triplicates and represented as mean±SEM. *P<0.05; P<0.01; *P<0.001; ****P<0.0001. This is described in Example 2.

Figure 6:
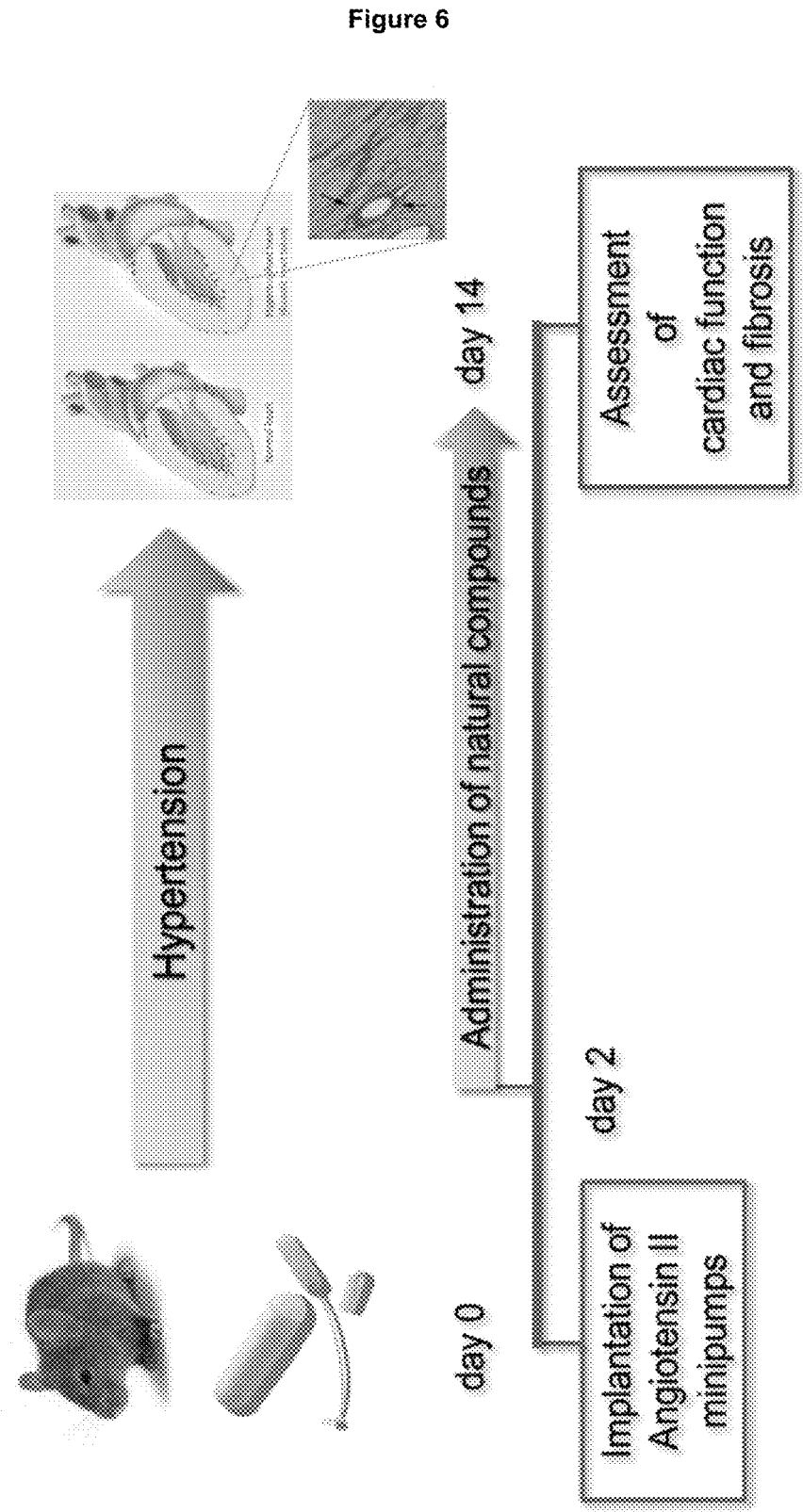

FIG. 6: Murine model of Angiotensin II-induced cardiac fibrotic disease.

Schematic overview of the in vivo verification of the anti-fibrotic potential of Lycorine, Bufalin, Gitoxigenin and Anisomycin. This is described in Example 3.

Figure 7:
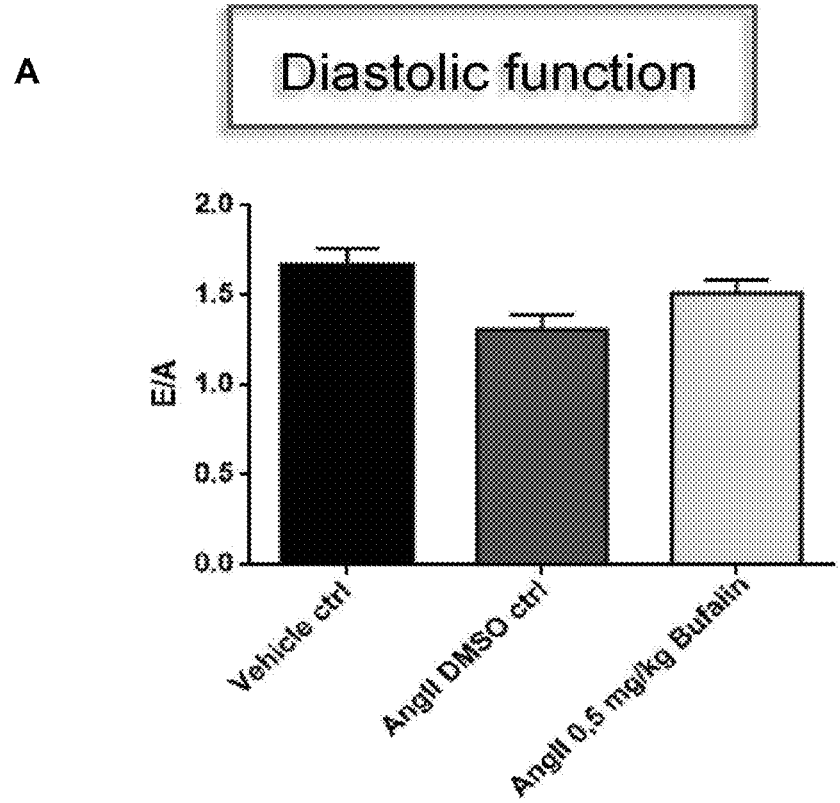
Figure 7:
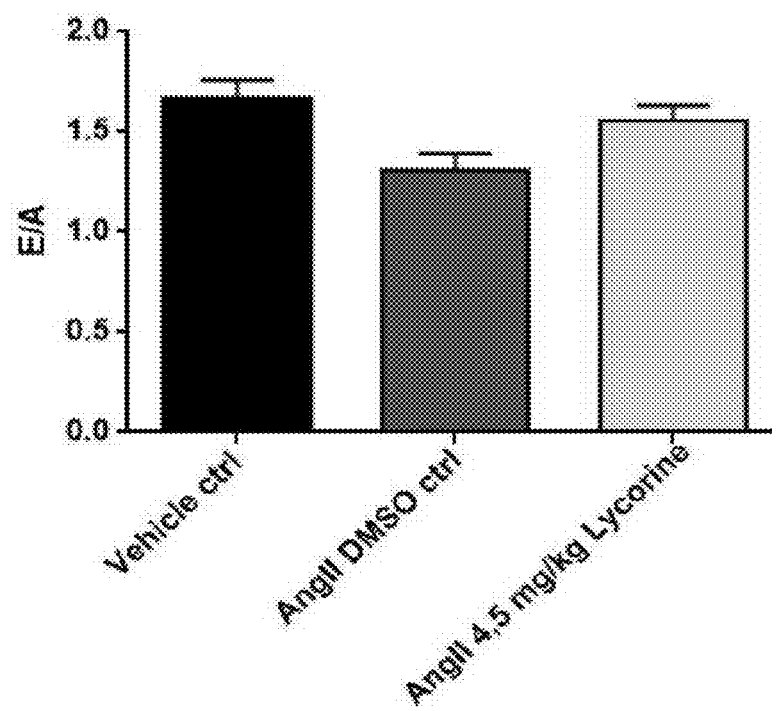

FIG. 7: Bufalin and Lycorine testing on cardiac function.

Bufalin and Lycorine significantly ameliorate cardiac function in a murine model of angiotensin II-induced cardiac fibrotic disease: Bufalin (A) and Lycorine (B) significantly improve both global and diastolic function of the heart as evidenced by a decrease of the Myocardial Performance Index (MPI) as well as a reduction of the isovolumetric relaxation time (IVRT) and an increase in E to A peak ratio (E/A), respectively. DMSO refers as control. Data are represented as mean±SEM. *P<0.05; P<0.01; *P<0.001; ****P<0.0001. This is described in Example 4.

Figure 8:
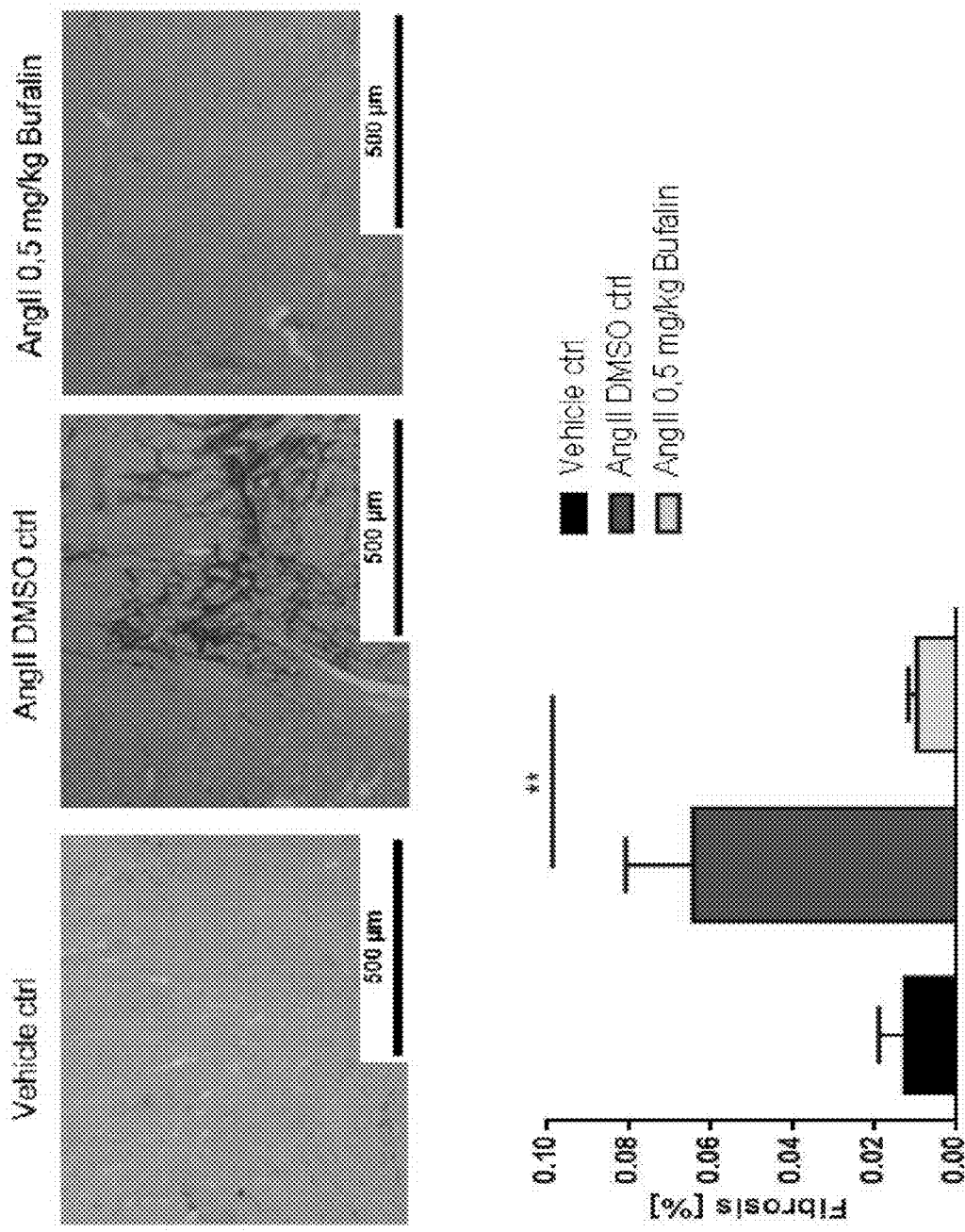
Figure 8:
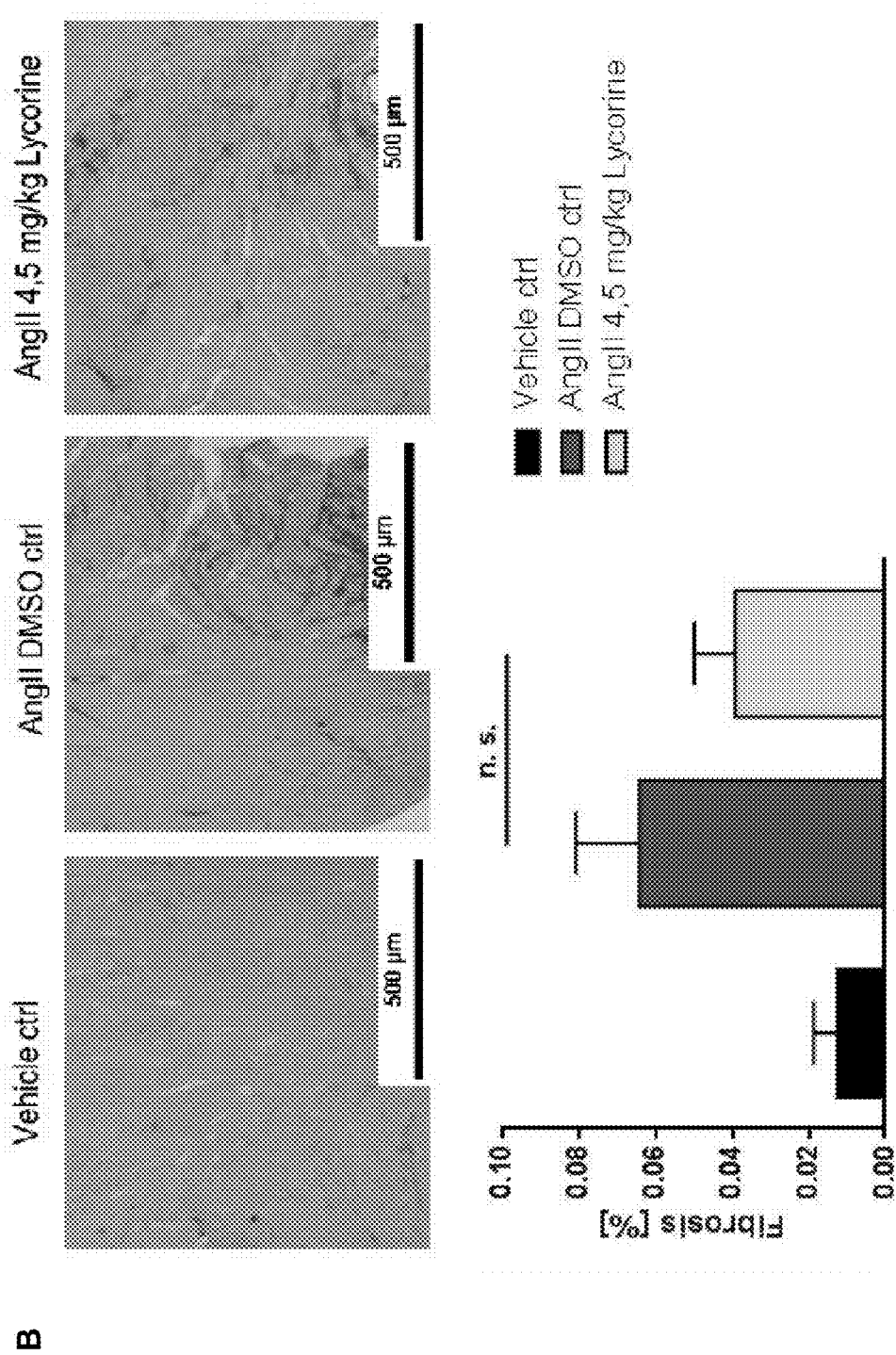

FIG. 8: Bufalin and Lycorine testing on cardiac fibrosis.

Bufalin and Lycorine ameliorate cardiac fibrosis in a murine model of angiotensin II-induced cardiac fibrotic disease: Bufalin (A) and Lycorine (B) prevent fibrosis-development as shown by a prominent reduction of collagen deposition in representative images of histological sections of the hearts as well as the quantification of picrosirius-stained areas. DMSO refers as control. Data are represented as mean±SEM. *P<0.05; P<0.01; *P<0.001; ****P<0.0001. This is described in Example 4.

Figure 9:
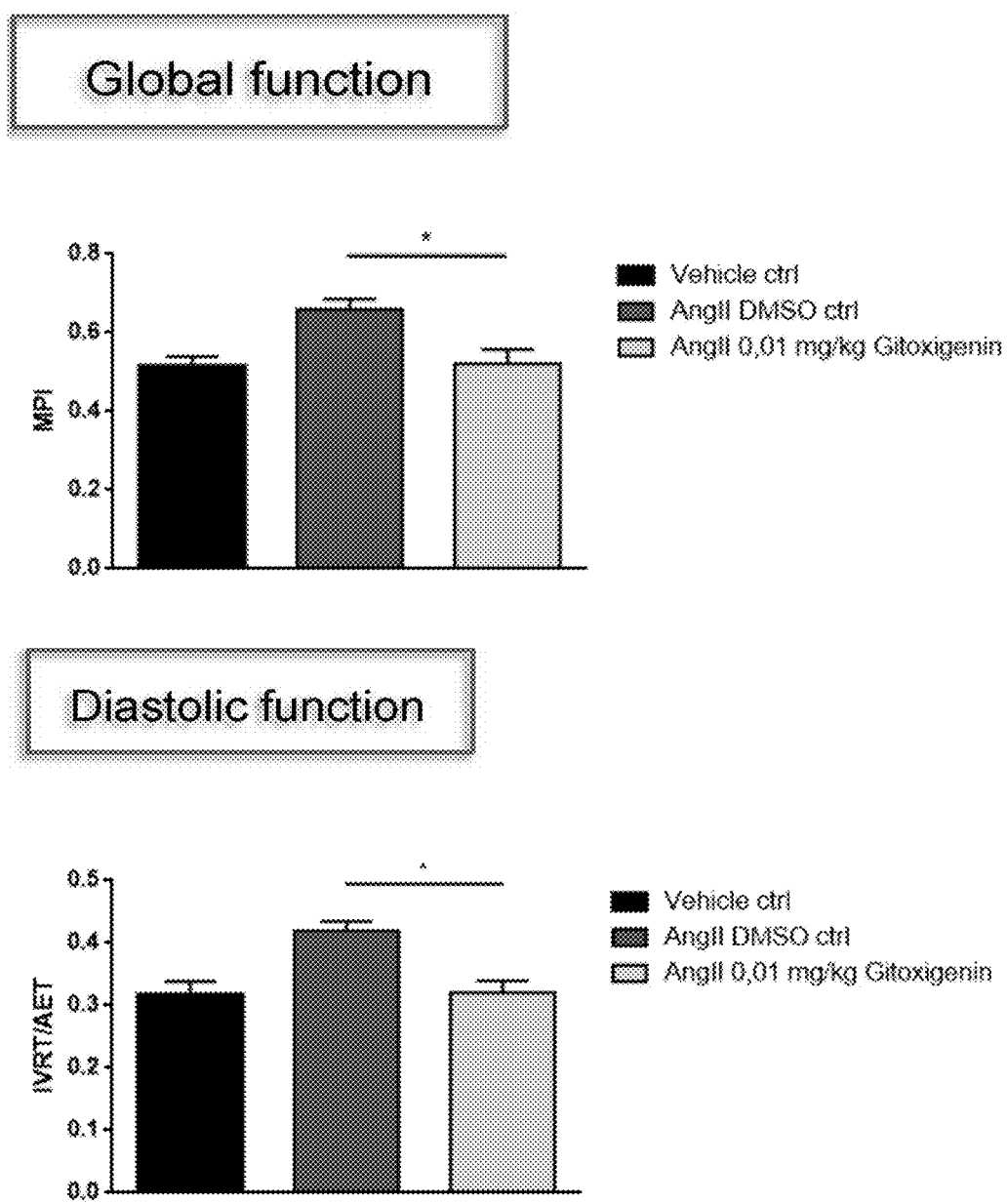

FIG. 9: Anisomycin and Gitoxigenin testing on cardiac function.

Anisomycin and Gitoxigenin significantly ameliorate cardiac function in a murine model of angiotensin II-induced cardiac fibrotic disease: Anisomycin (A) and Gitoxigenin (B) significantly improve both global and diastolic function of the heart as evidenced by a decrease of the Myocardial Performance Index (MPI) as well as a reduction of the isovolumetric relaxation time (IVRT) and an increase in E to A peak ratio (E/A), respectively. DMSO refers as control. Data are represented as mean±SEM. *P<0.05; P<0.01; *P<0.001; ****P<0.0001. This is described in Example 4.

Figure 10:
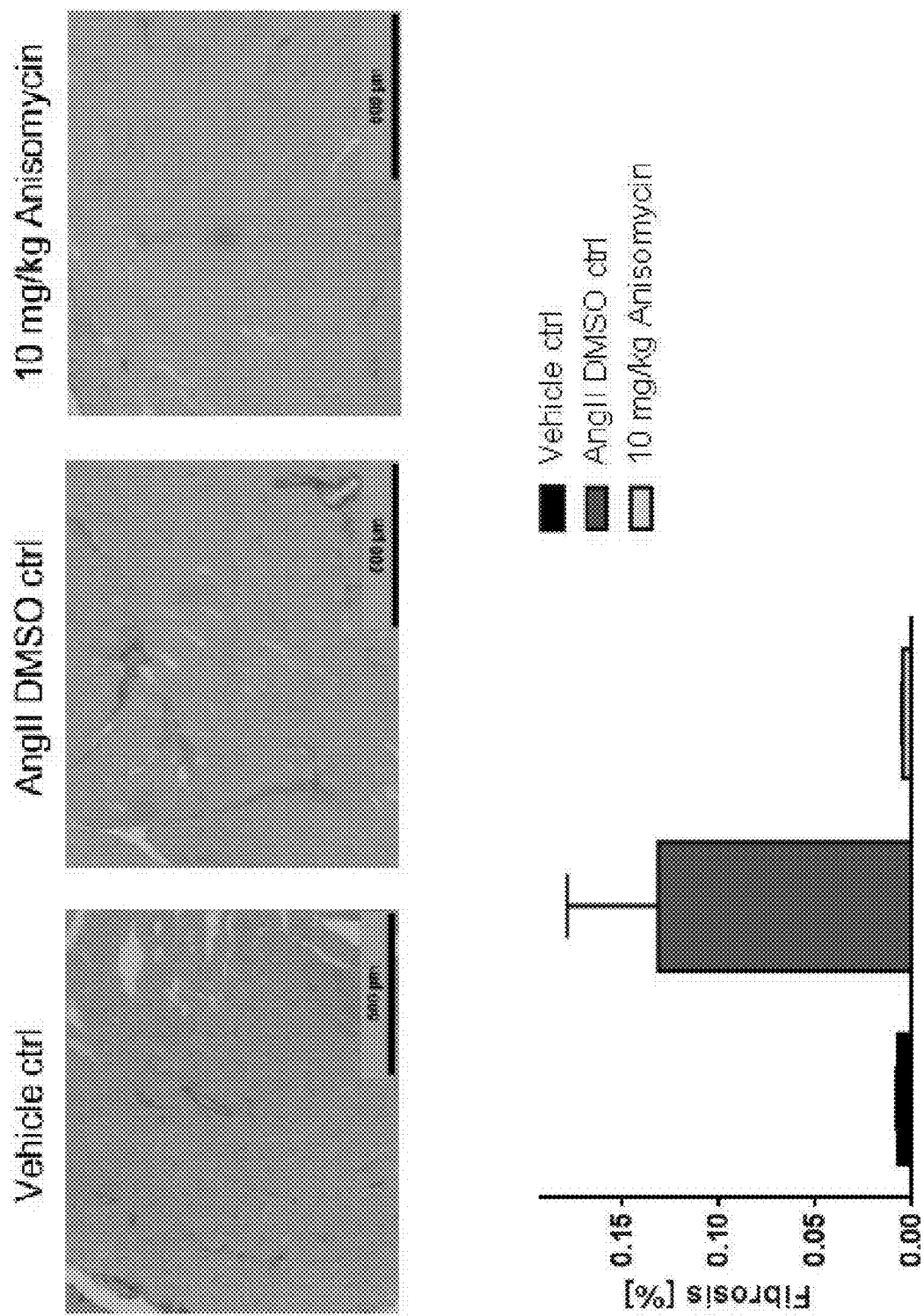
Figure 10:
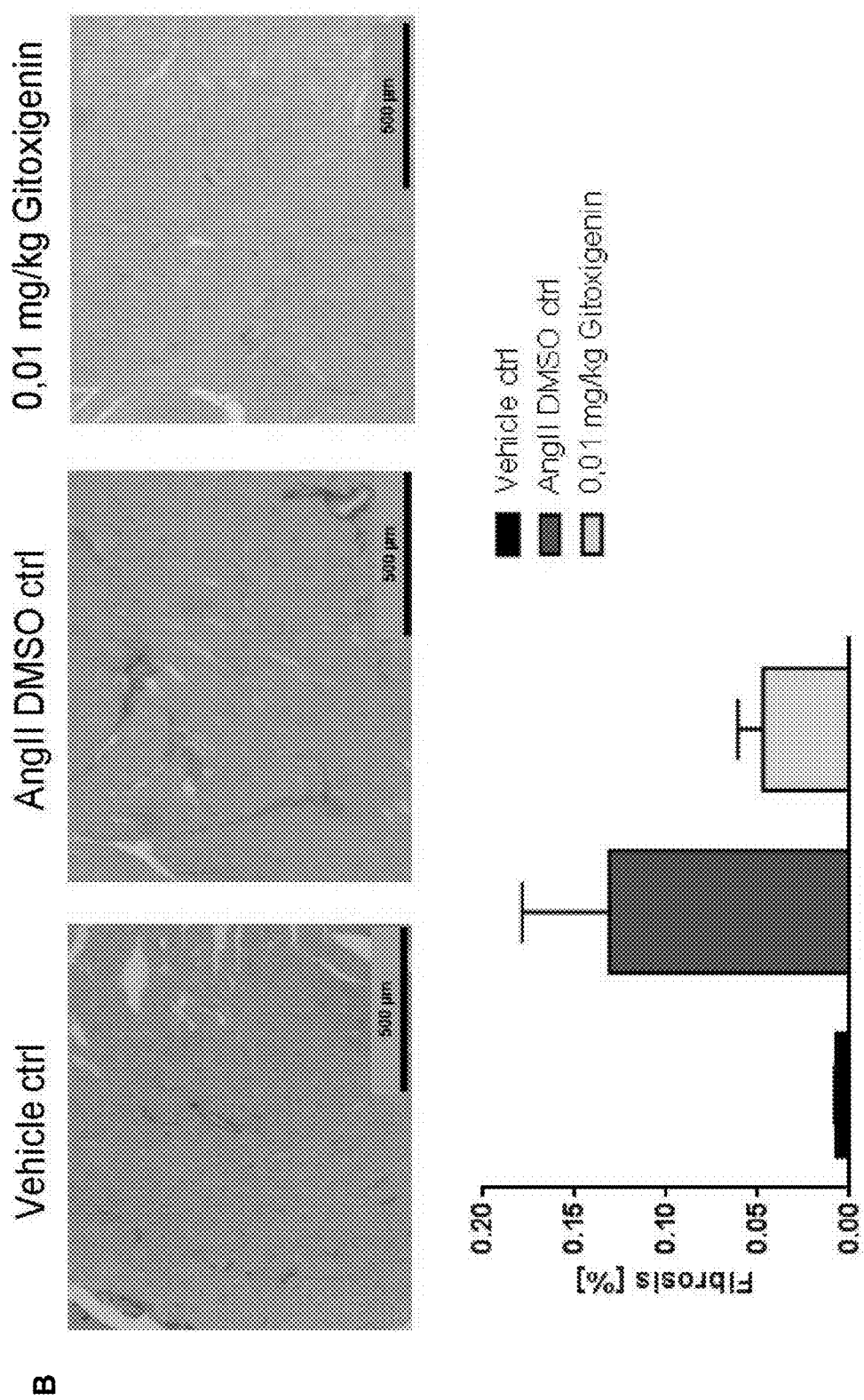

FIG. 10: Anisomycin and Gitoxigenin testing on cardiac fibrosis.

Anisomycin and Gitoxigenin ameliorate cardiac fibrosis in a murine model of angiotensin II-induced cardiac fibrotic disease: Anisomycin (A) and Gitoxigenin (B) prevent fibrosis-development as shown by a prominent reduction of collagen deposition in representative images of histological sections of the hearts as well as the quantification of picrosirius-stained areas. DMSO refers as control. Data are represented as mean±SEM. *P<0.05; P<0.01; *P<0.001; ****P<0.0001. This is described in Example 4.

Figure 11:
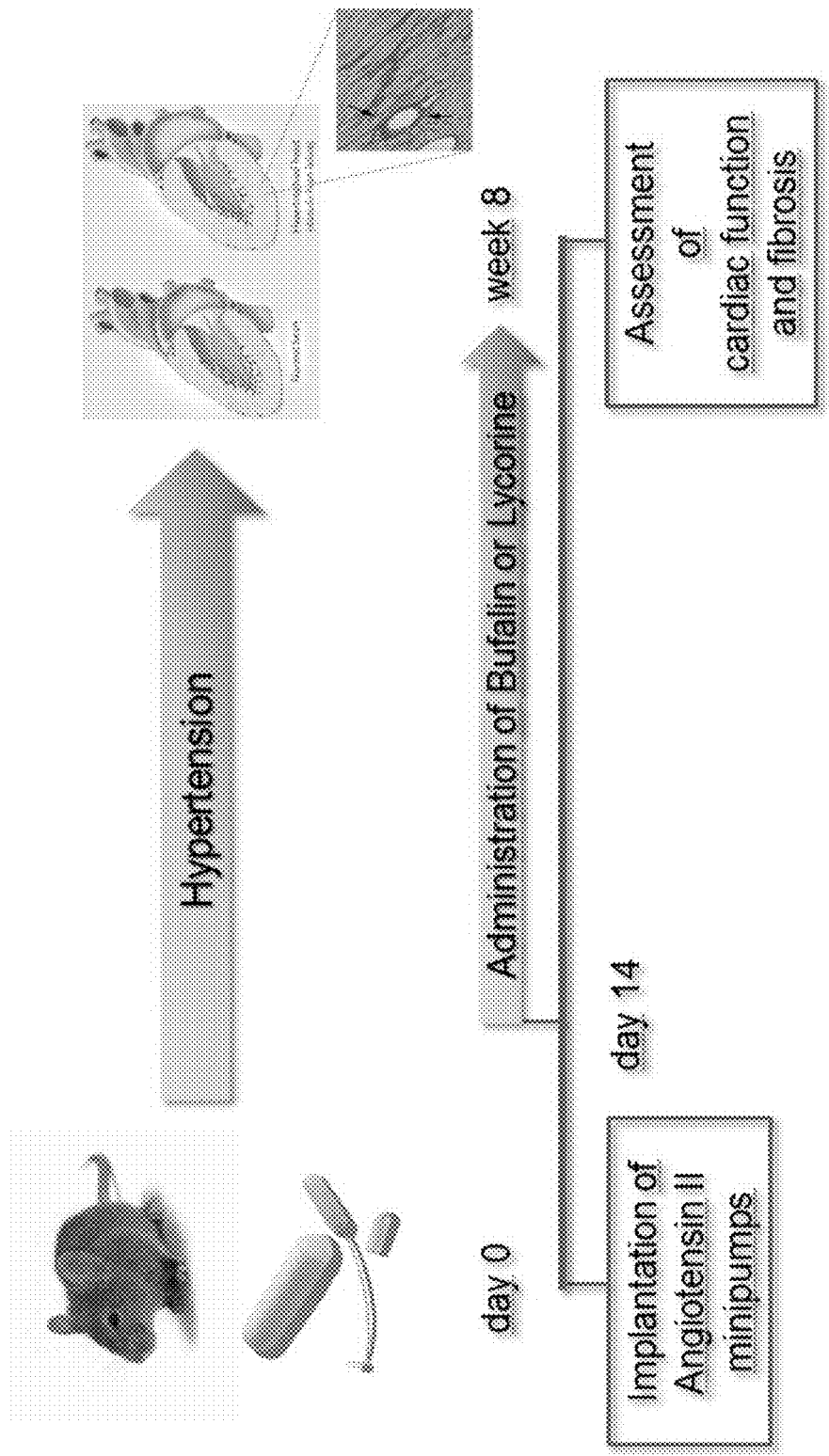

FIG. 11: Therapeutic murine model of hypertension-induced diastolic dysfunction.

Schematic overview of the therapeutic in vivo study of Lycorine and Bufalin. This is described in Example 5.

Figure 12:
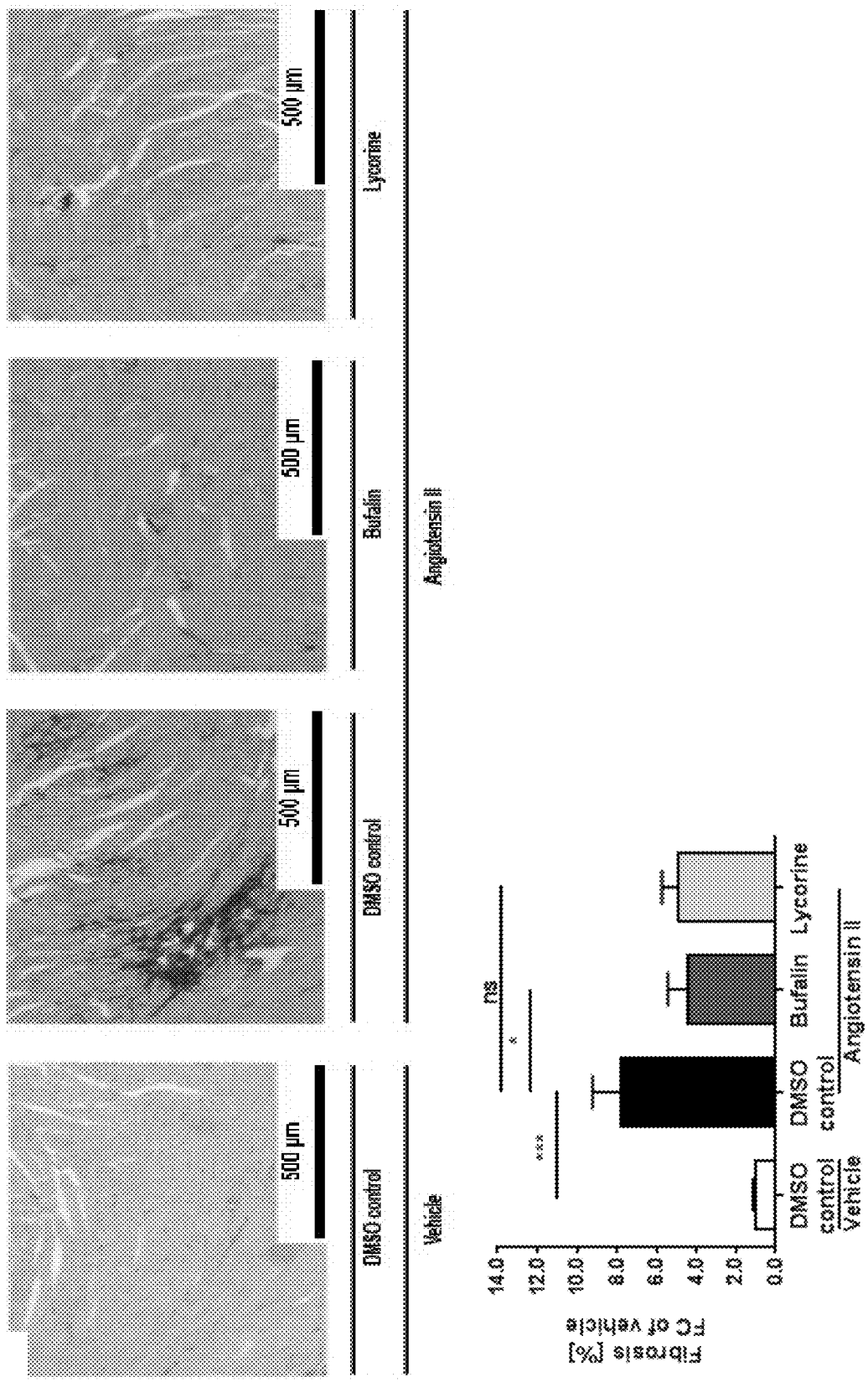
Figure 12:
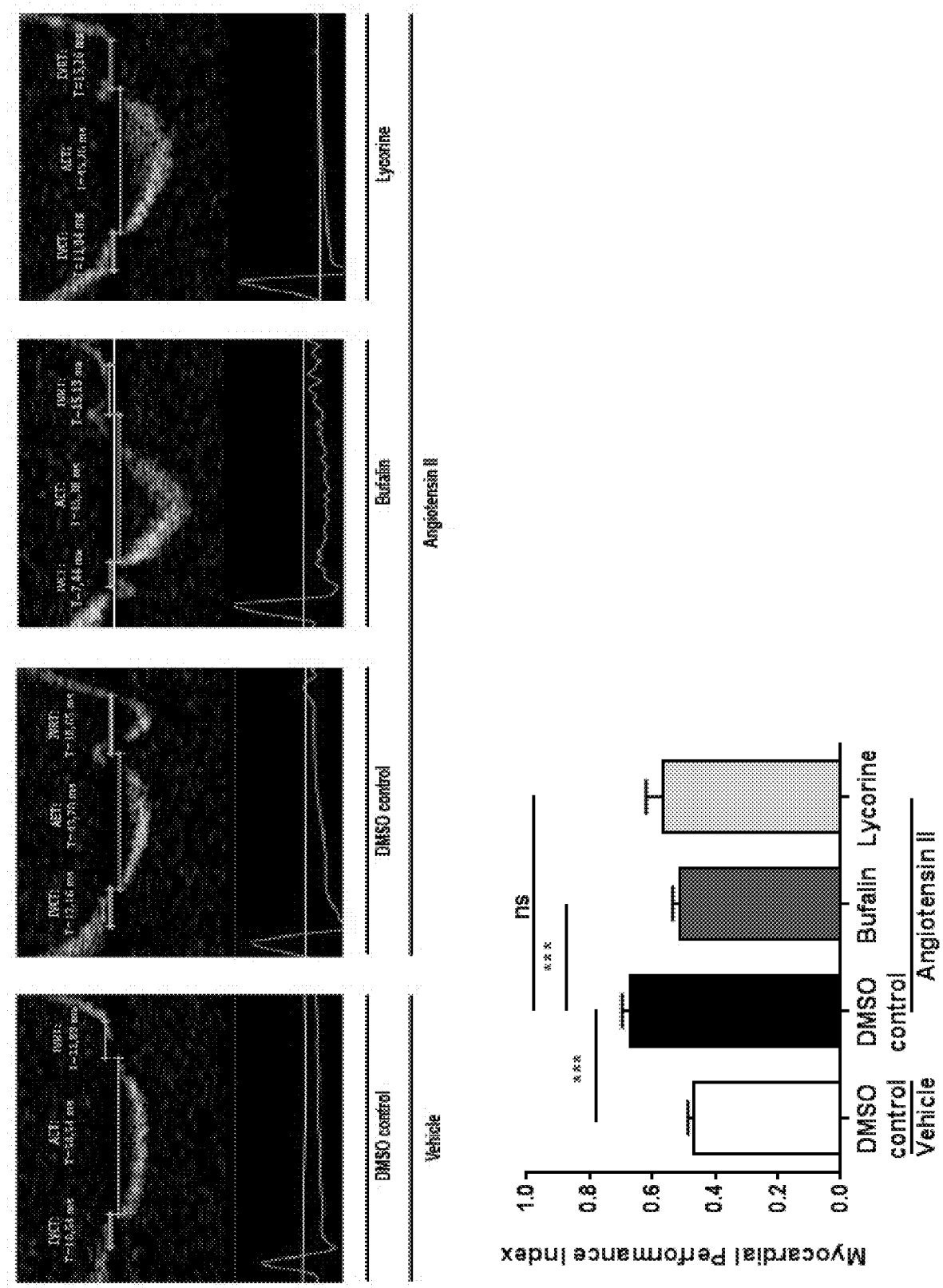
Figure 12:
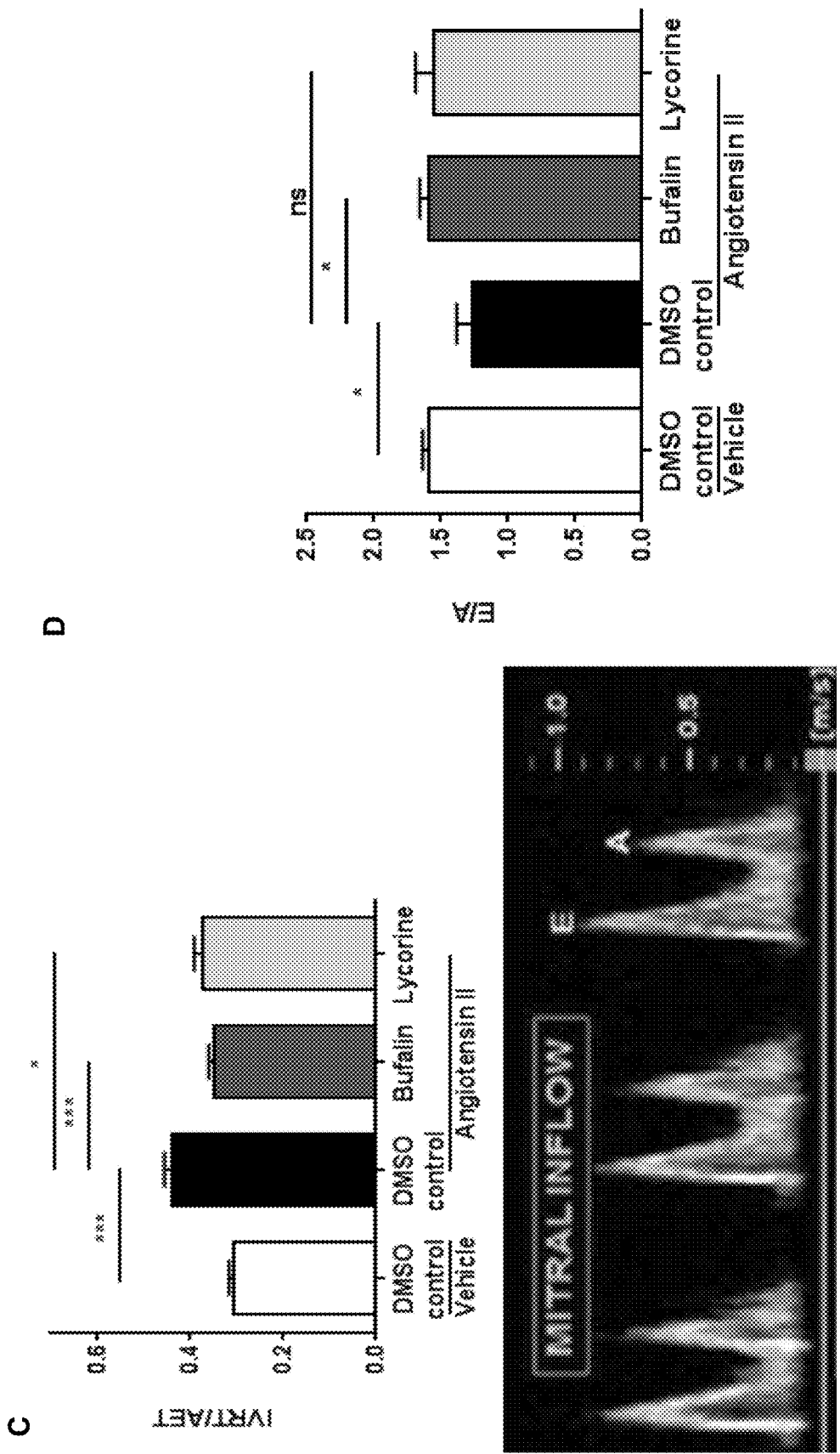

FIG. 12: Bufalin and Lycorine testing for cardiac fibrosis.

A) Bufalin and Lycorine prevent further development of cardiac fibrosis in established diastolic heart failure upon treatment as shown by a reduction of collagen deposition in representative images of histological sections of the hearts as well as the quantification of picrosirius-stained areas. Particularly Bufalin significantly improves both global and diastolic function of the heart as evidenced by a (B) decrease of the Myocardial Performance Index (MPI) as well as a (C) reduction of the isovolumetric relaxation time (IVRT) and an (D) increase in E to A peak ratio, respectively. DMSO refers as control. Data are represented as mean±SEM. *P<0.05; P<0.01; *P<0.001; ****P<0.0001. This is described in Example 6.

Figure 13:
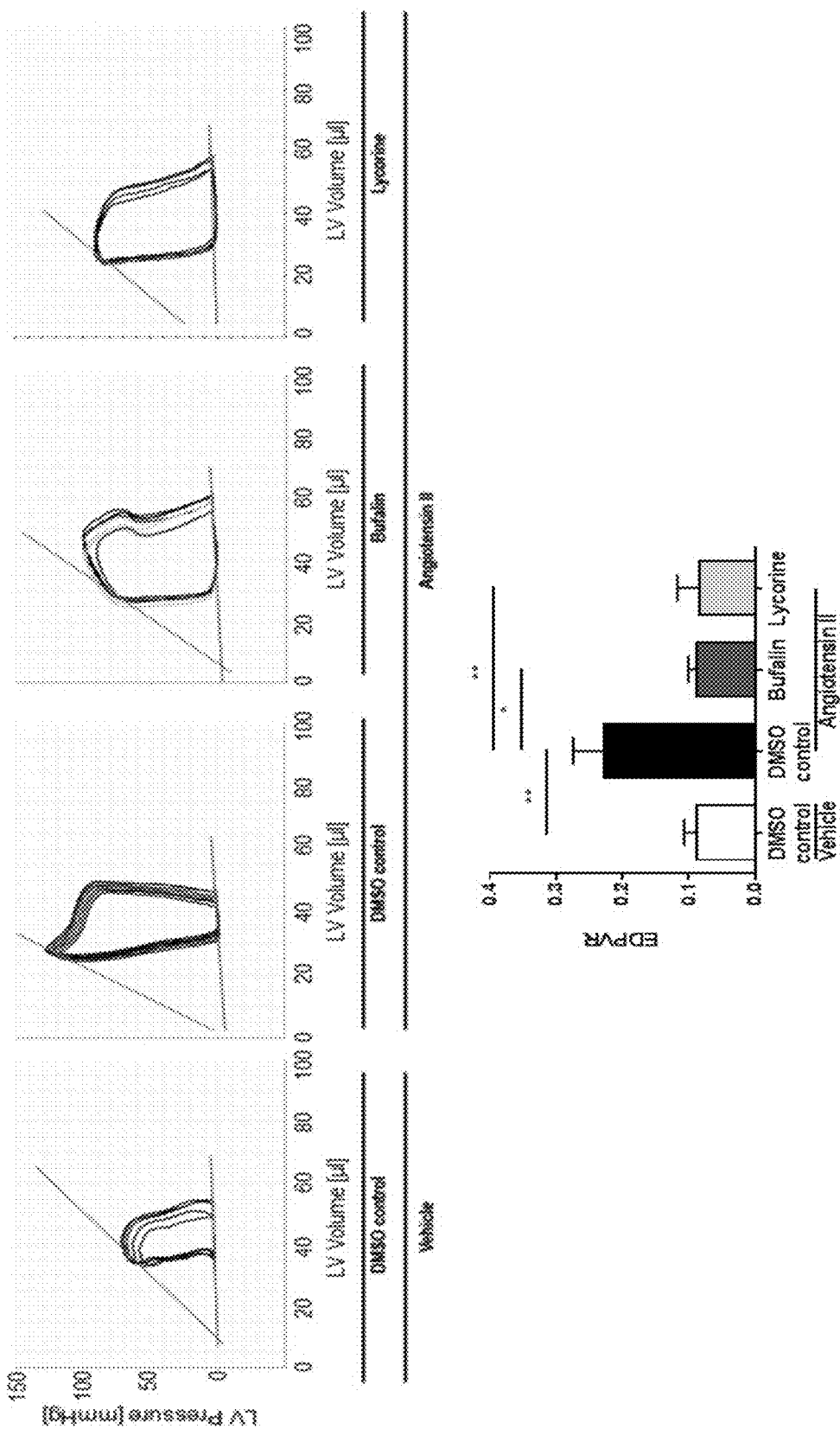

FIG. 13: Bufalin and Lycorine recover left ventricular compliance of the murine heart upon angiotensin II-infusion.

Bufalin and Lycorine reduce passive stiffness of the left ventricle induced by systemic hypertension, as evidenced by a significant reduction of the end-diastolic pressure-volume relationship (EDPVR) by Bufalin and Lycorine. DMSO refers as control. Data are represented as mean±SEM. *P<0.05; P<0.01; *P<0.001; ****P<0.0001. This is described in Example 7.

Figure 14:
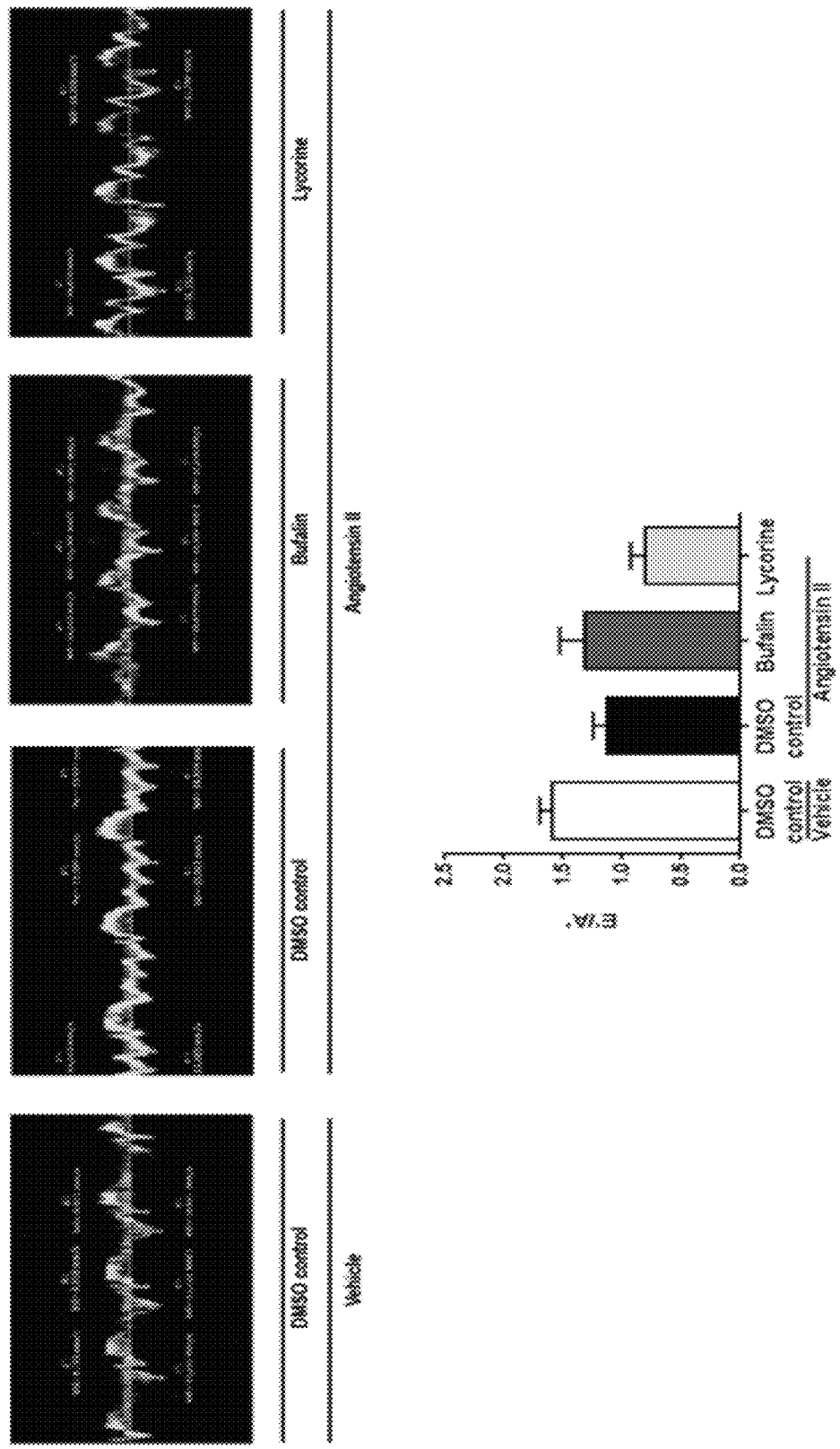

FIG. 14: Bufalin accelerates tissue motion during diastole in a murine model of angiotensin II-infusion.

Bufalin recovers the velocity of tissue motion in diastole (increased E' as compared to AngII solvent only control) decelerated upon angiotensin II-infusion (decreased E' as compared to vehicle solvent only control) shown in the quantification and representative images of tissue Doppler imaging. DMSO refers as control. Data are represented as mean±SEM. *P<0.05; P<0.01; *P<0.001; ****P<0.0001. This is described in Example 8.

Figure 15:
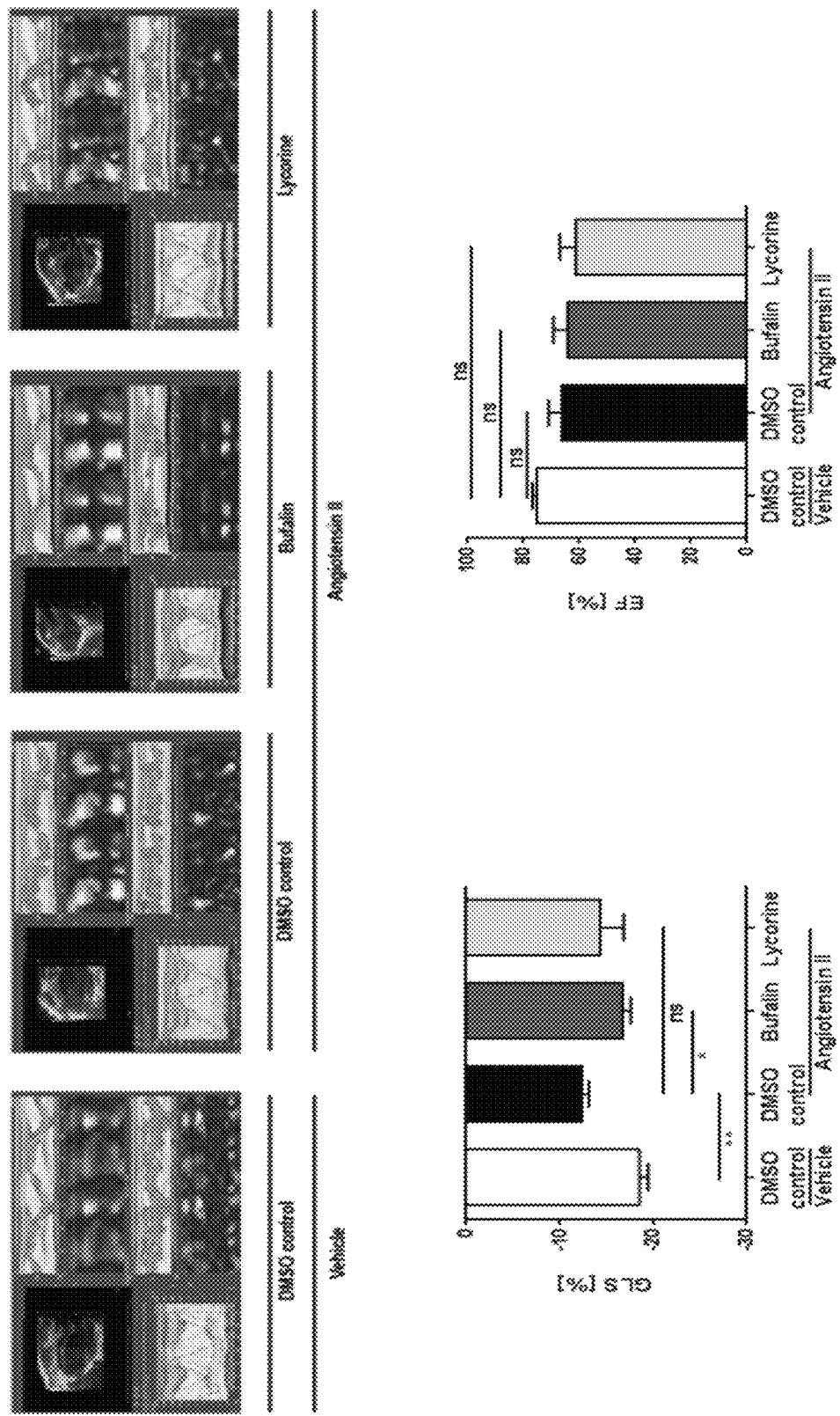

FIG. 15: Bufalin recovers global longitudinal strain (GLS) in a murine model of angiotensin II-induced cardiac fibrotic disease.

2-dimensional speckle-tracking strain echocardiography uncovered a significant reversal of the downshift of global longitudinal strain (GLS) of the heart caused by angiotensin II-infusion upon treatment with Bufalin as shown both in representative images and quantification. DMSO refers as control. In accordance with the murine model for heart failure with preserved ejection fraction (HFpEF), ejection fraction (EF) remained comparable in all tested groups. Data are represented as mean±SEM. *$P<0.05$; $P<0.01$; *$P<0.001$; ****$P<0.0001$. This is described in Example 8.

FIG. 16: High-throughput miRNA sequencing in human cardiac fibroblasts.

Bufalin impacts on the miRNA expression of HCFs in vitro and changes the miRNA-signature of HCFs. Some miRNAs, in particular 33 miRNAs are downregulated (A) and some miRNAs (in particular 14 miRNAs) are upregulated (B) in HCFS after treatment with Bufalin compared to the control DSMO. A table of the top-30 significantly deregulated miRNAs is shown in (A). Data represent pooled triplicates from 3 independent experiments. This is described in Example 9.

Figure 17:
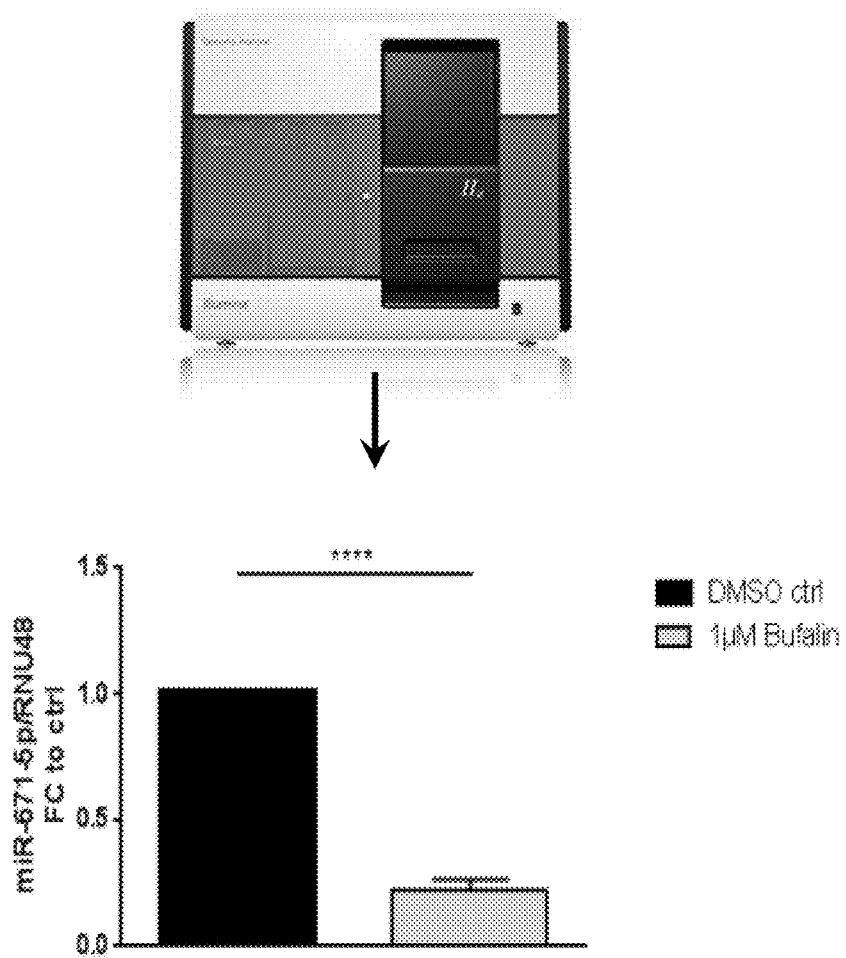
Figure 17:
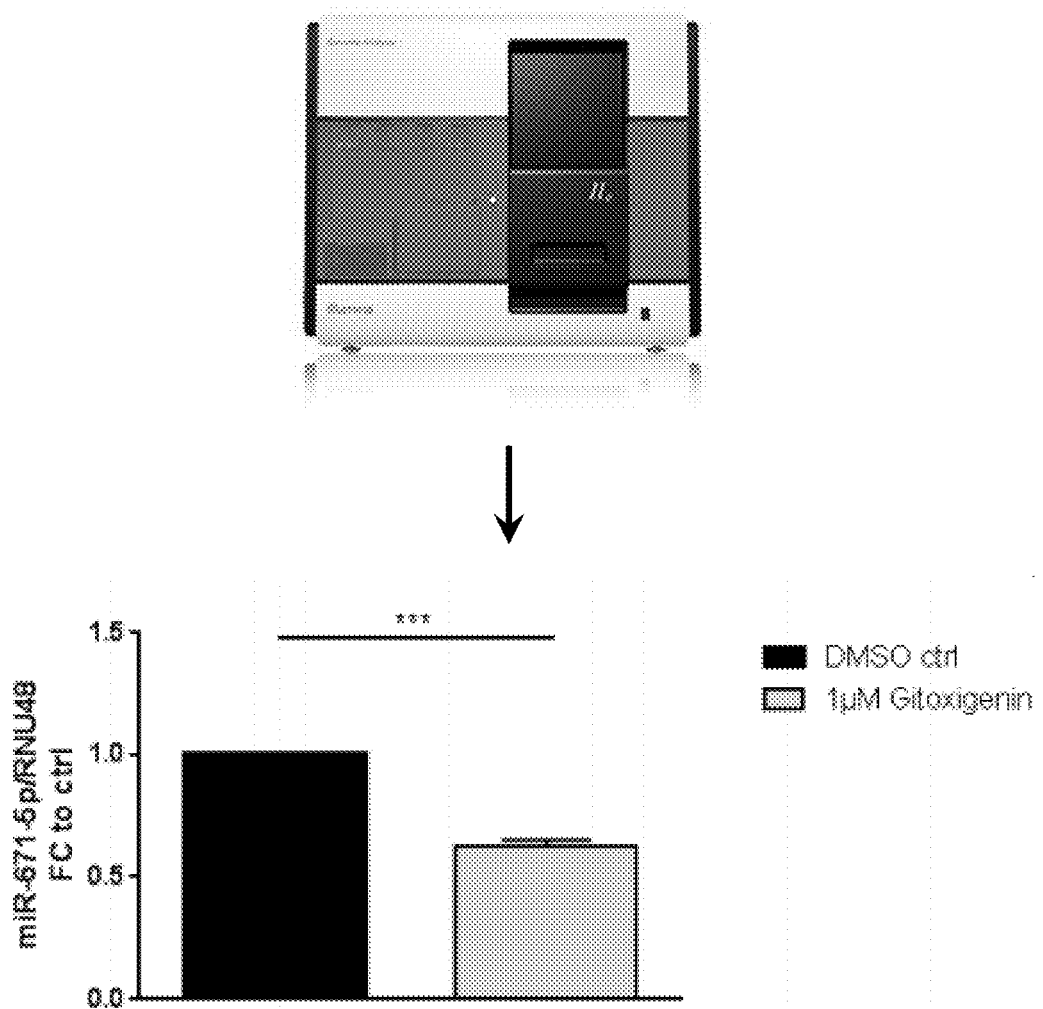
Figure 17:
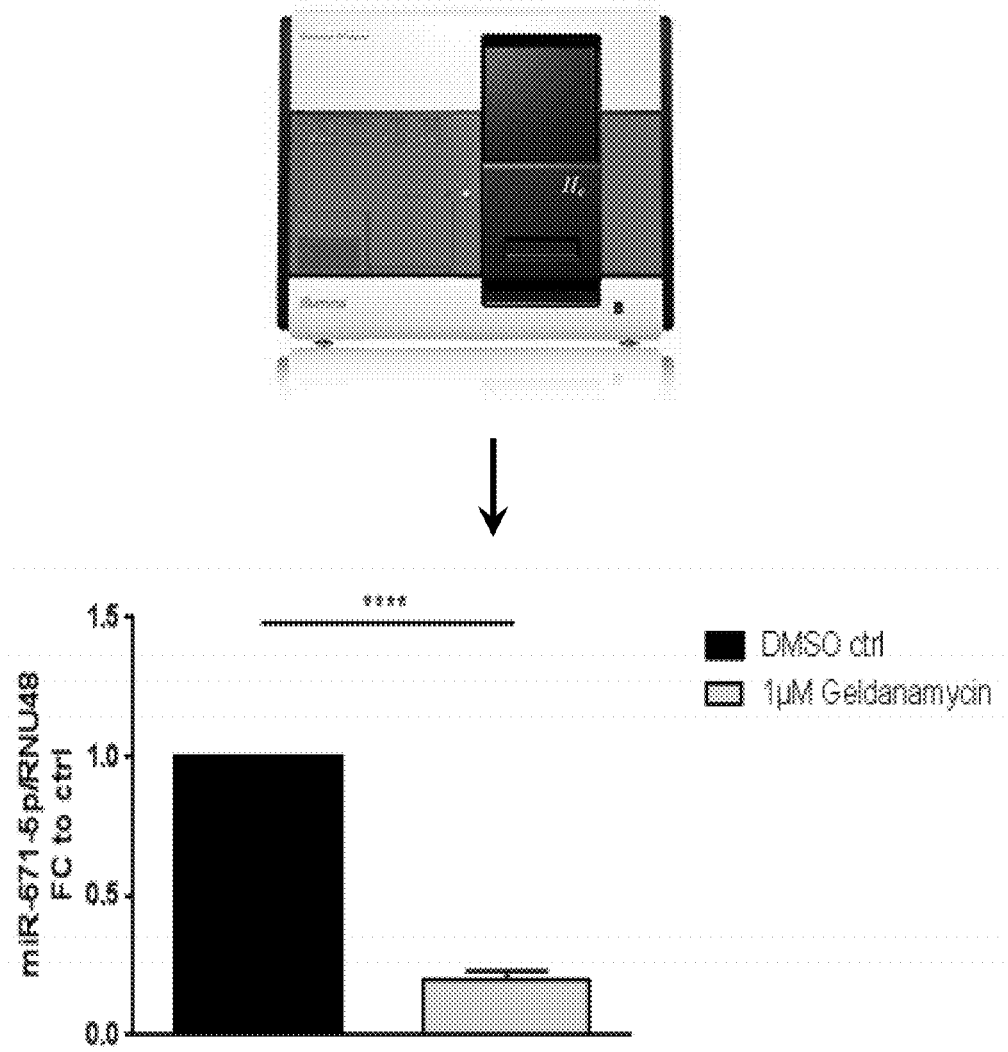
Figure 17:
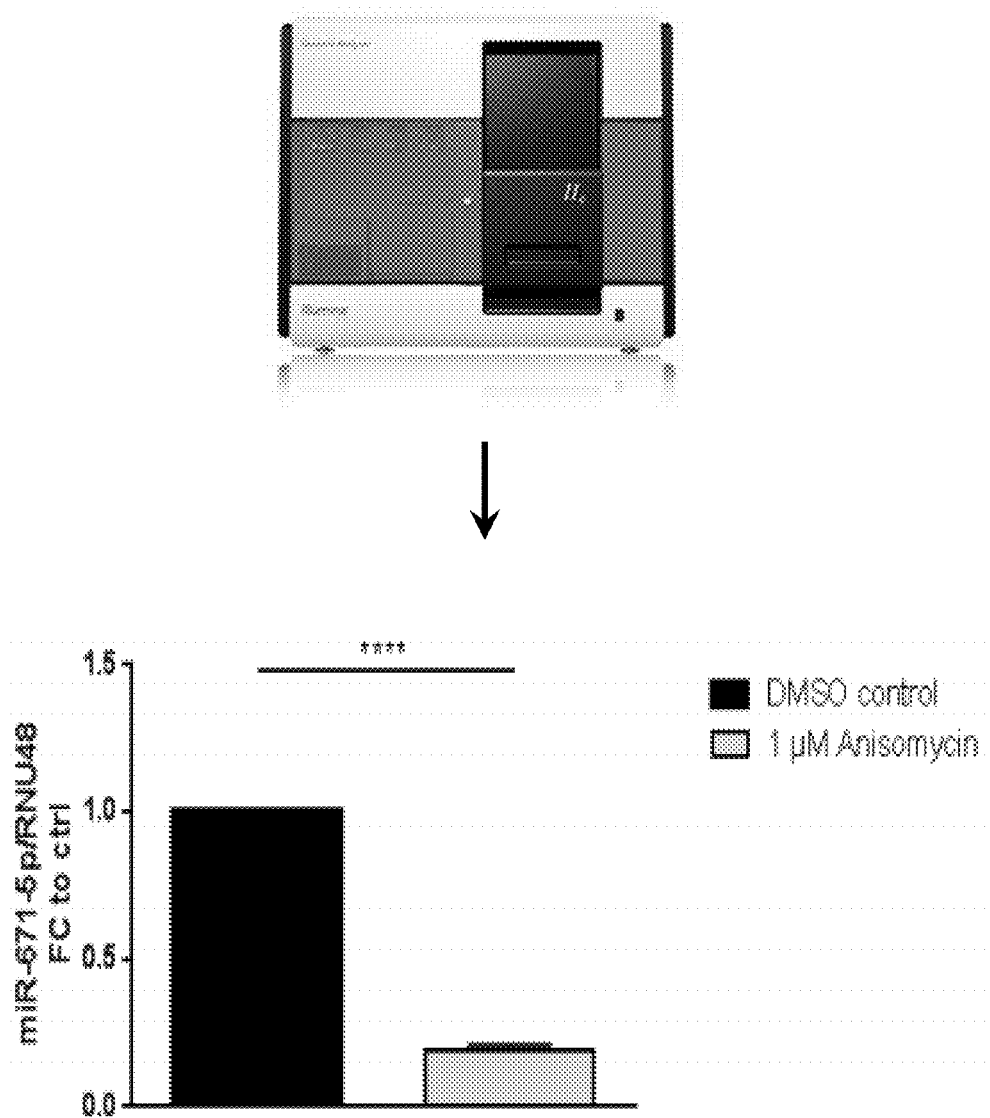
Figure 17:
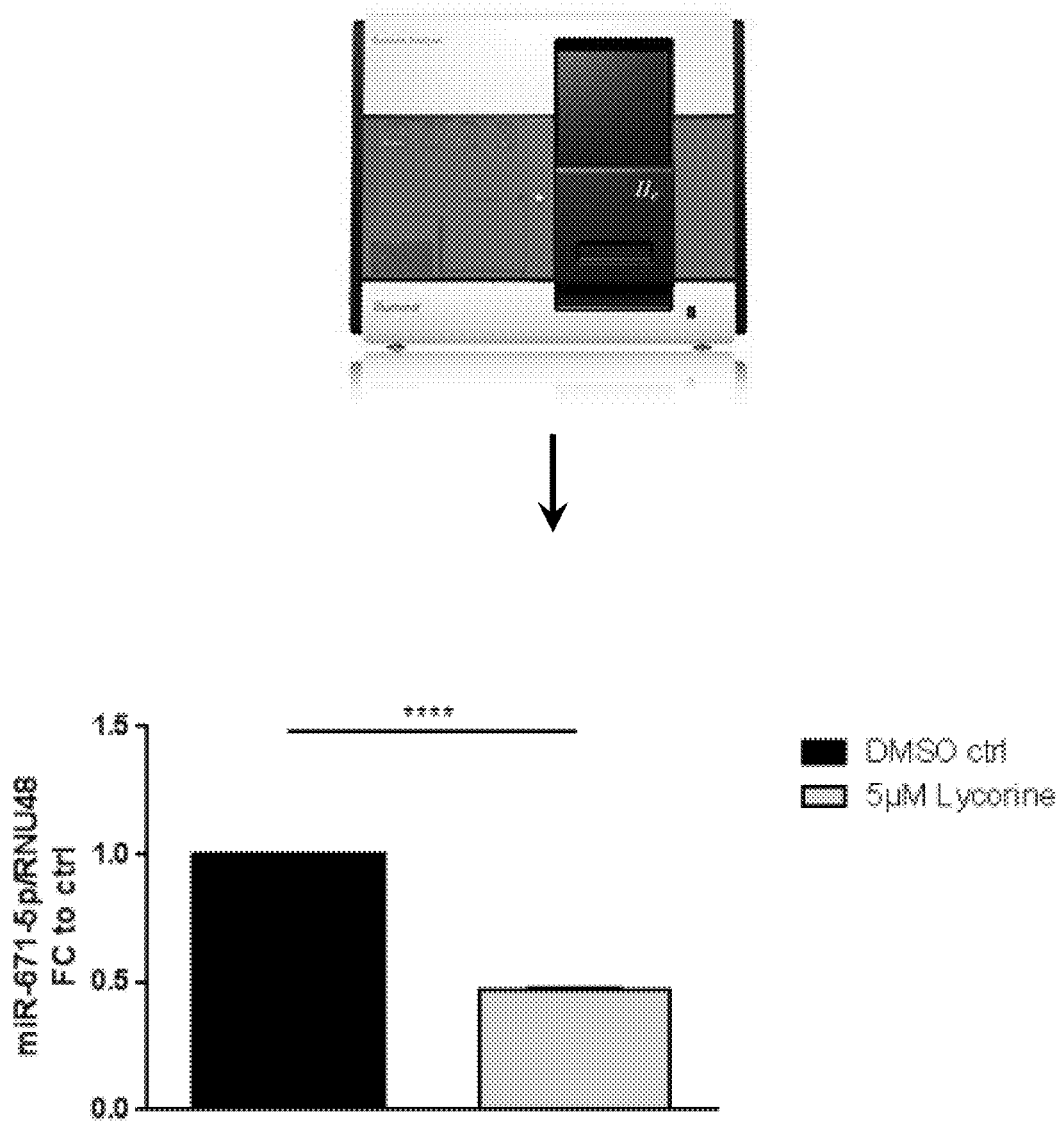

FIG. 17: miRNA sequencing in human cardiac fibroblasts.

miR-671-5p levels are significantly decreased by identified anti-fibrotic compounds in HCFs: Expression levels of miR-671-5p are decreased in primary HCFs upon treatment with Bufalin, Gitoxigenin, Lycorine, Anisomycin and Geldanamycin as compared to the DMSO-control. Downregulation of miR-671-5p (normalized to RNU48) by the respective compound was validated via qRT-PCR. Data are depicted as the average of 3 independent measurements performed in triplicates and represented as mean±SEM. *$P<0.05$; $P<0.01$; *$P<0.001$; ****$P<0.0001$. This is described in Example 10.

Figure 18:
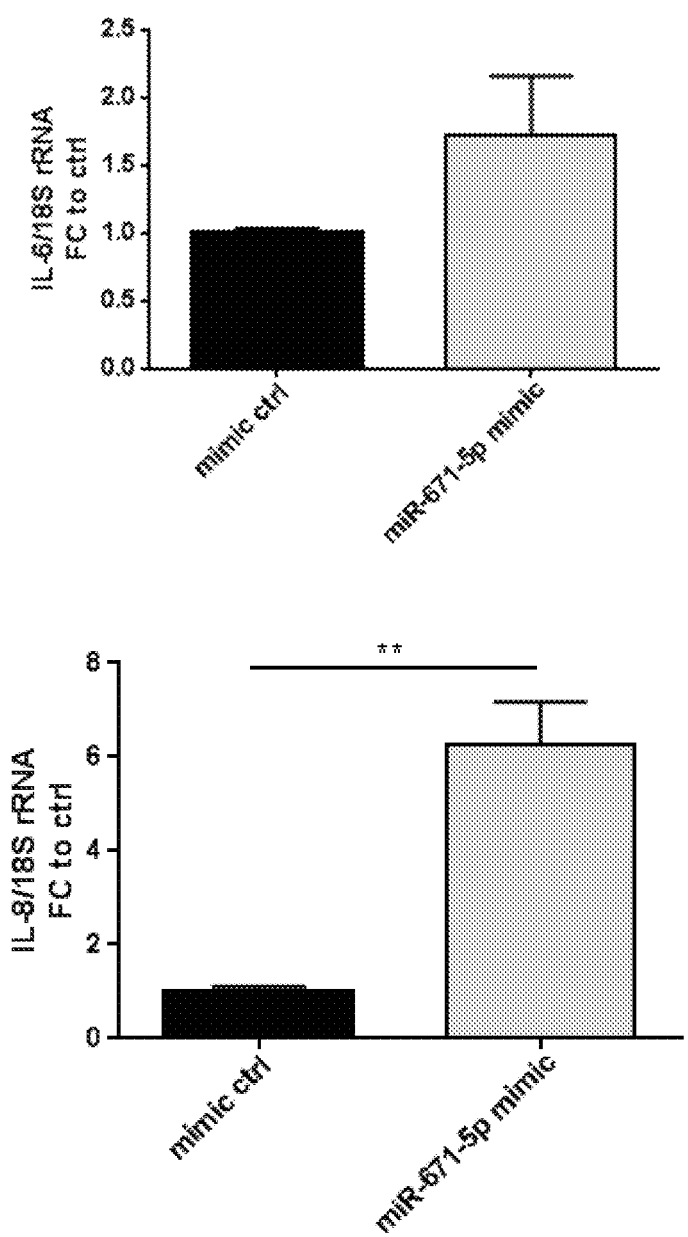

FIG. 18: In vitro experiments on miRNA in human cardiac fibroblasts.

miR-671-5p regulates fibrosis and inflammation in HCFs in vitro: A) Overexpression of miR-671-5p leads to activation of markers of fibrosis ($\alpha$-Smooth Muscle Actin, $\alpha$-SMA and Connective Tissue Growth Factor, CTGF) and inflammation (Interleukin-6, IL-6 and Interleukin-8, IL-8) in primary HCFs. B) Conversely, inhibition of miR-671-5p leads to a prominent decrease in above mentioned markers of fibrosis and inflammation (normalized to 18S rRNA) in primary HCFs. Data are depicted as the average of 4 independent measurements performed in triplicates and represented as mean±SEM. *$P<0.05$; $P<0.01$; *$P<0.001$; ****$P<0.0001$. This is described in Example 11.

Figure 19:
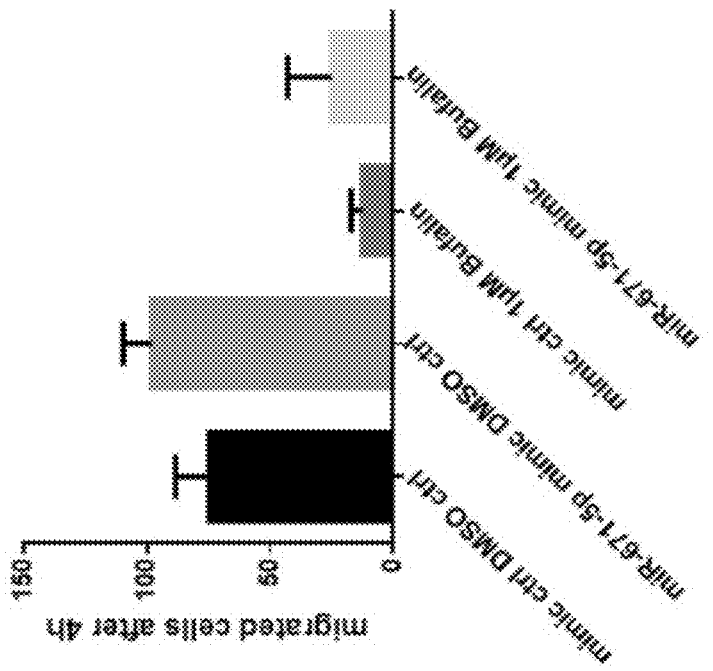

FIG. 19: Overexpression of miR-671-5p in human cardiac fibroblasts.

Overexpression of miR-671-5p enhances migration of HCFs both under control and under treatment conditions with Bufalin. Overexpression of miR-671-5p stimulates migration of primary HCFs both with and without treatment with anti-fibrotic Bufalin. Data are depicted as the average of 3 independent measurements performed in triplicates and represented as mean±SEM. *$P<0.05$; $P<0.01$; *$P<0.001$; ****$P<0.0001$. This is described in Example 11.

FIG. 20: In vivo study of miR-671-5p levels in cardiac fibrosis.

miR-671-5p levels change in cardiac fibrotic diseases. Expression of miR-671-5p is increased in various murine heart failure models (hypertension, pressure overload and allogenic heart transplantation). HF was induced in mice via (A) implantation of angiotensin II filled minipumps, (B) Transverse Aortic Constriction (TAC) or (C) allogenic transplantation of the hearts. D) miR-671-5p is activated in human hearts of aortic stenosis-patients. Increased levels of miR-671-5p (normalized to snoRNA-202 in murine and to RNU48 human heart tissue) were studied via qRT-PCR. Data are represented as mean±SEM. *$P<0.05$; $P<0.01$; *$P<0.001$; ****$P<0.0001$. This is described in Example 12.

FIG. 21: In vitro studies of CDR1as as a direct target of miR-671-5p.

The circular RNA CDR1as is a direct target of miR-671-5p: A) Predicted consequential pairing of CDR1as and miR-671-5p (www.targetscan.org/vert_71/) in humans. Divergent primers were used to specifically amplify the circular RNA, which is highly abundant in HCFs as represented by low CT-values. B) Circularity of CDR1as was evidenced by resistance to exonuclease treatment that was 10-times fold higher than the resistance of the linear transcript of GAPDH. C) Validation of miR-671-5p targeting CDR1as by qRT-PCR (normalized to 18S rRNA) after overexpression of miR-671-5p in primary HCFs. Data are depicted as the average of 2-4 independent measurements performed in triplicates and represented as mean±SEM. *$P<0.05$; $P<0.01$; *$P<0.001$; ****$P<0.0001$. This is described in Example 13.

Figure 22:
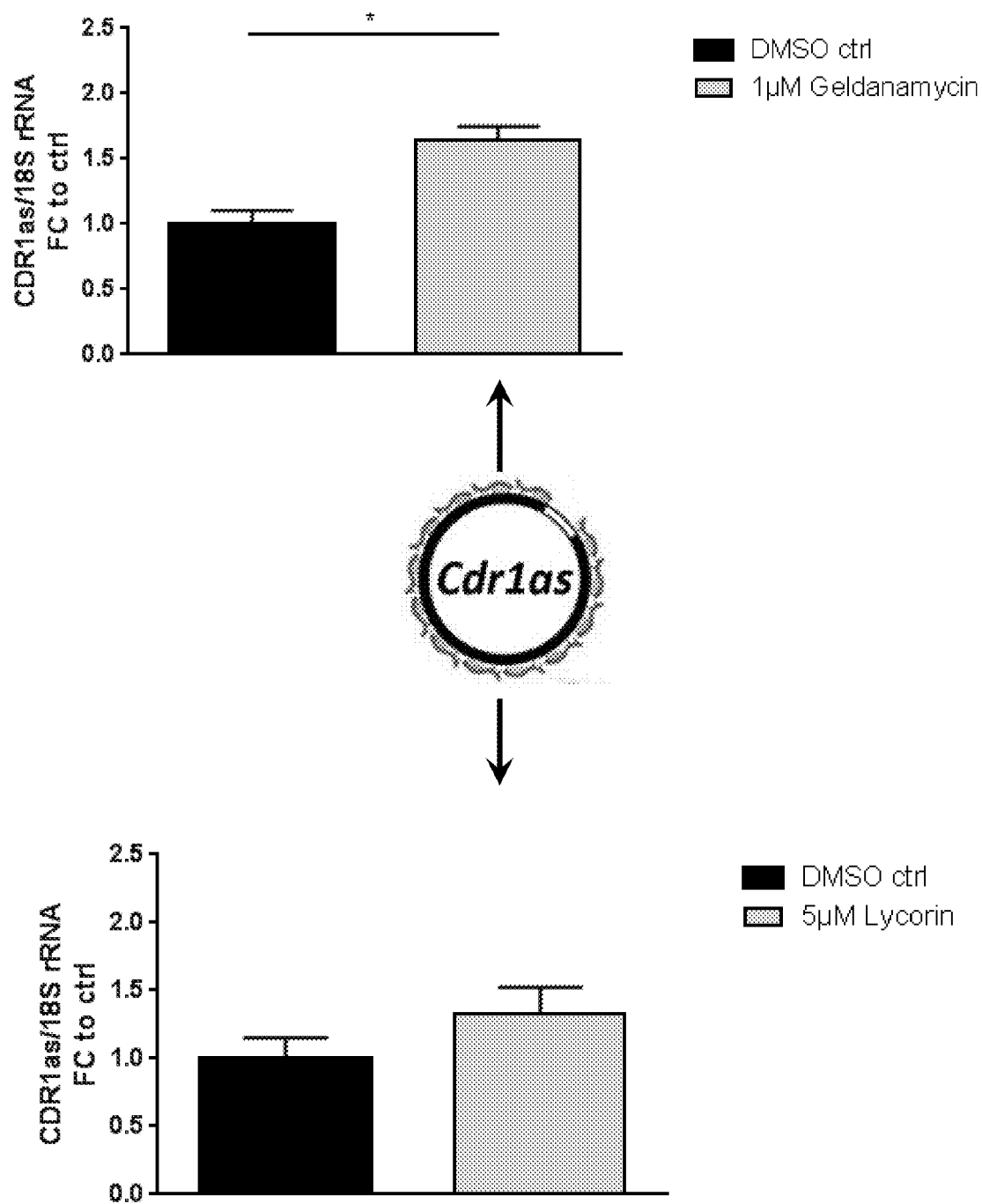
Figure 22:
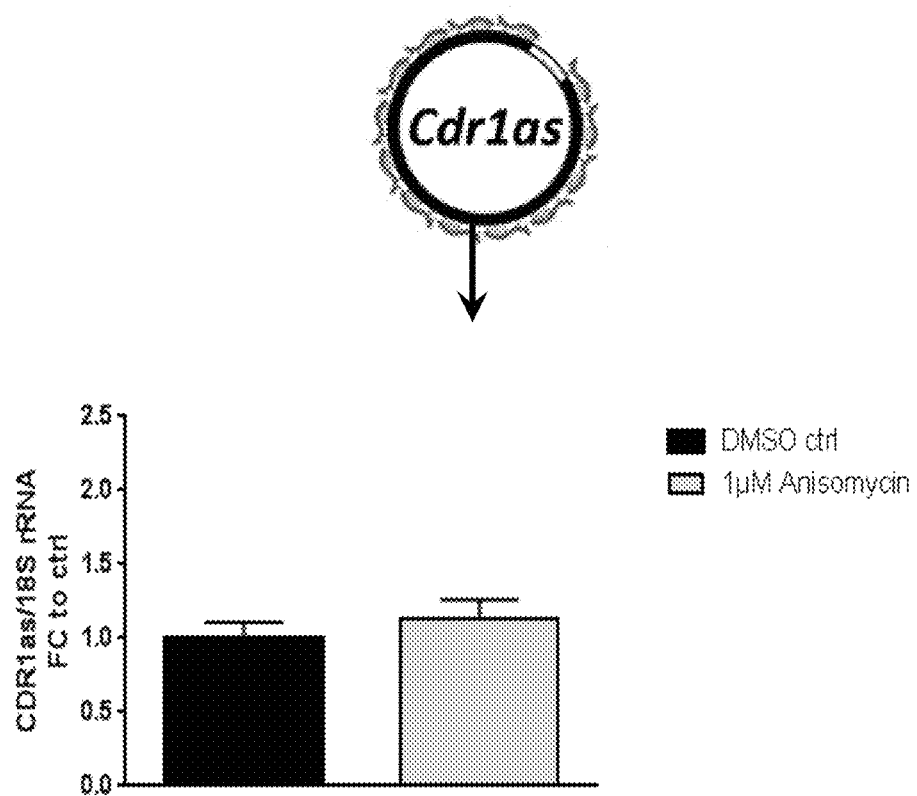

FIG. 22: Expression levels of circular RNA CDR1as in human cardiac fibroblasts.

The circular RNA CDR1as is increased after treatment with identified anti-fibrotic compounds in HCFs. Expression levels of CDR1as increase in primary HCFs upon treatment with Bufalin, Gitoxigenin, Lycorine, Anisomycin and Geldanamycin as compared to the DMSO-control, following an opposite pattern as compared to miR-671-5p. The respective compound was validated via qRT-PCR (normalized to 18S rRNA). Data are depicted as the average of 3 independent measurements performed in triplicates and represented as mean±SEM. *$P<0.05$; $P<0.01$; *$P<0.001$; ****$P<0.0001$. This is described in Example 14.

Figure 23:
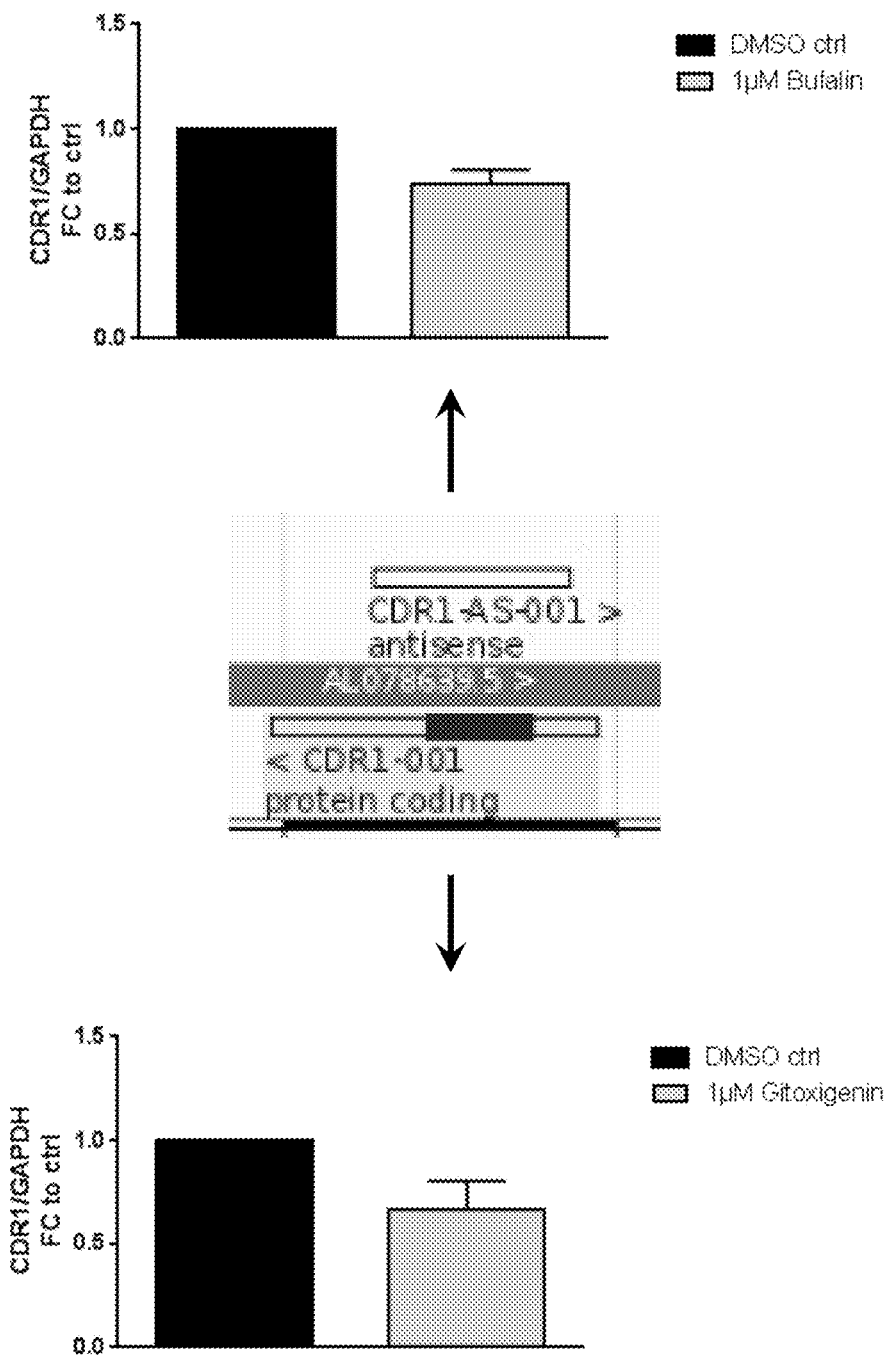
Figure 23:
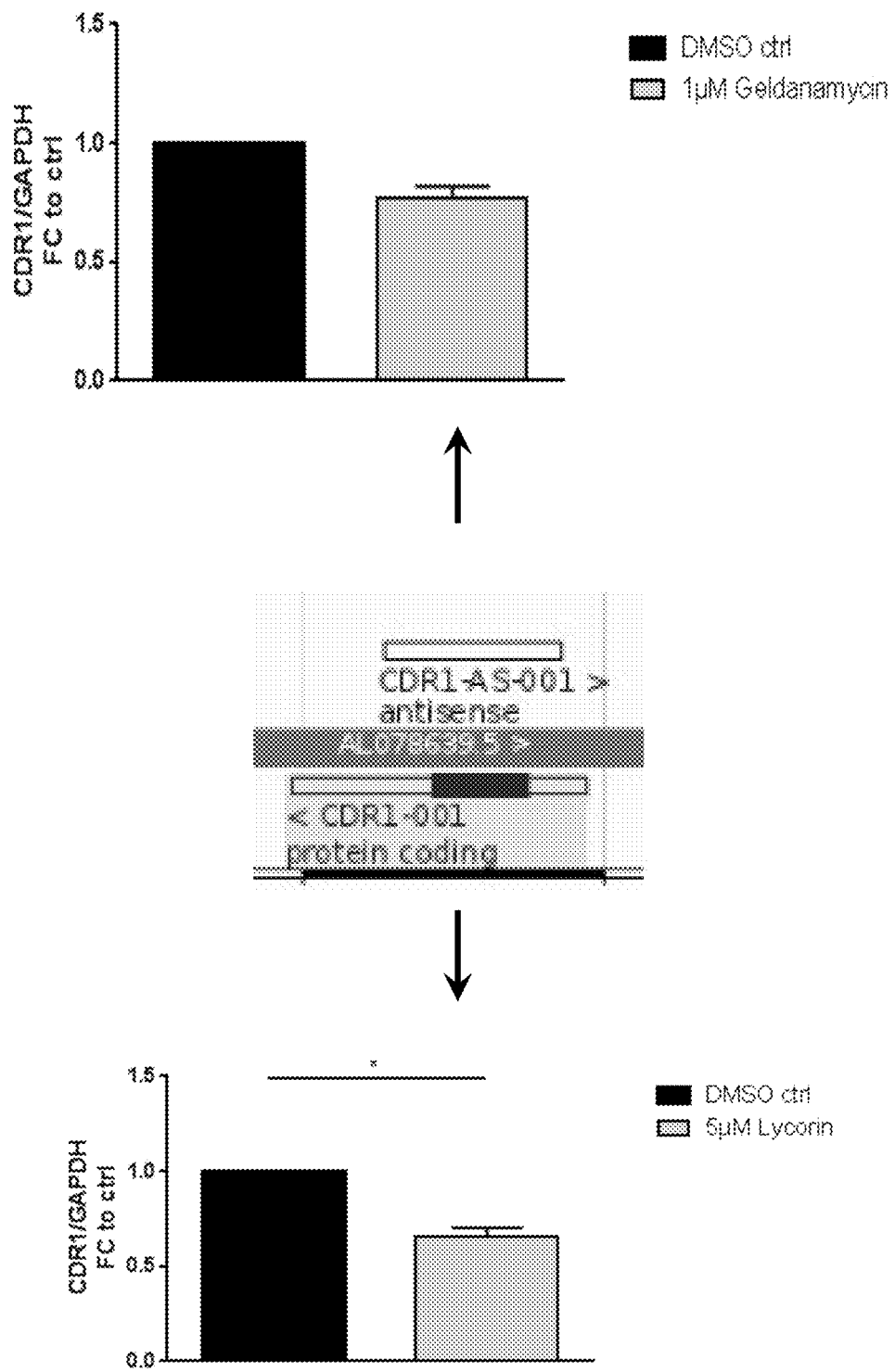
Figure 23:
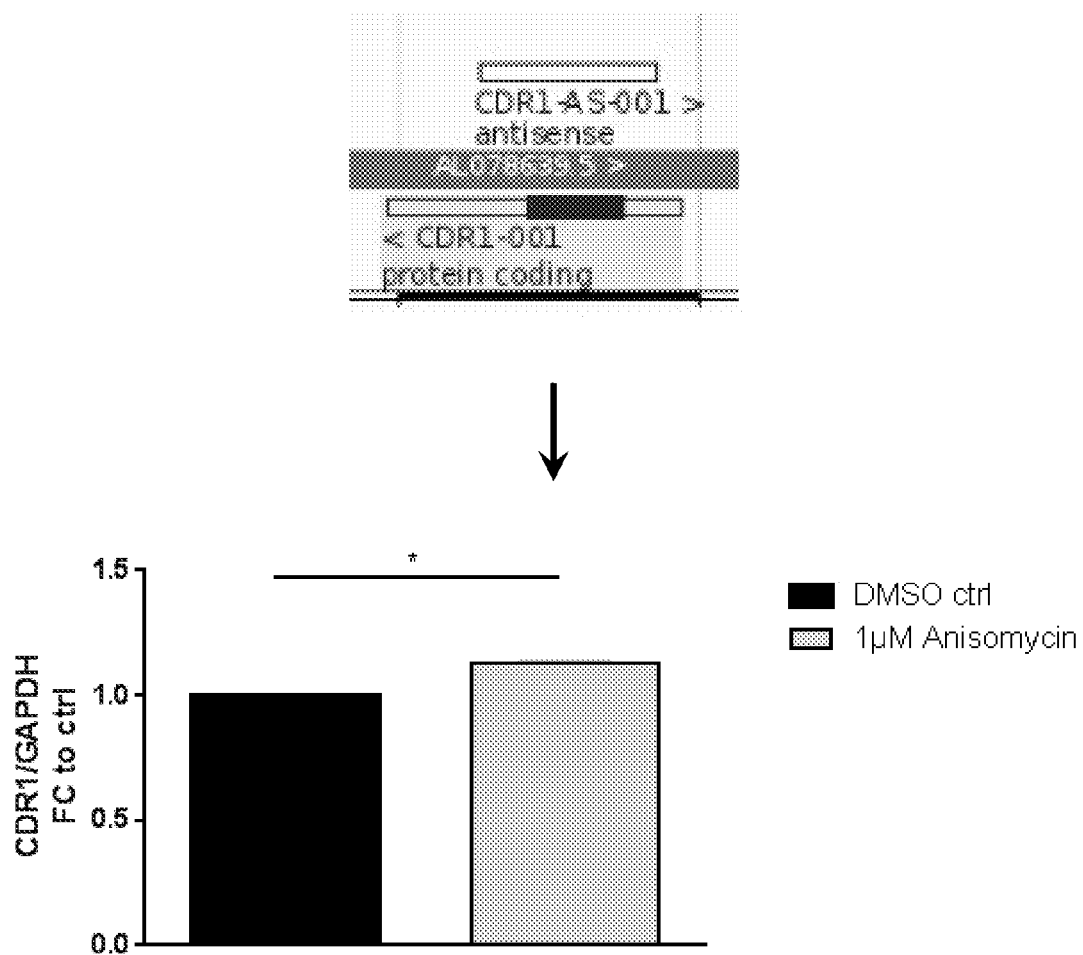

FIG. 23: In vitro study of effect of miR-671-5p on CDR1 mRNA.

The CDR1 mRNA encoded on the opposite strand of CDR1as changes discordantly to miR-671-5p after treatment with identified anti-fibrotic compounds in HCFs. Expression levels of CDR1 mRNA change independently of miR-671-5p or CDR1as in primary HCFs upon treatment with Bufalin, Gitoxigenin, Lycorine, Anisomycin and Geldanamycin as compared to the DMSO-control. Expression levels of CDR1 mRNA decrease in primary HCFs upon said treatment. The respective compound was validated via qRT-PCR (normalized to GAPDH). Data are depicted as the average of 3 independent measurements performed in triplicates and represented as mean±SEM. *$P<0.05$; $P<0.01$; *$P<0.001$; ****$P<0.0001$. This is described in Example 15.

Figure 24:
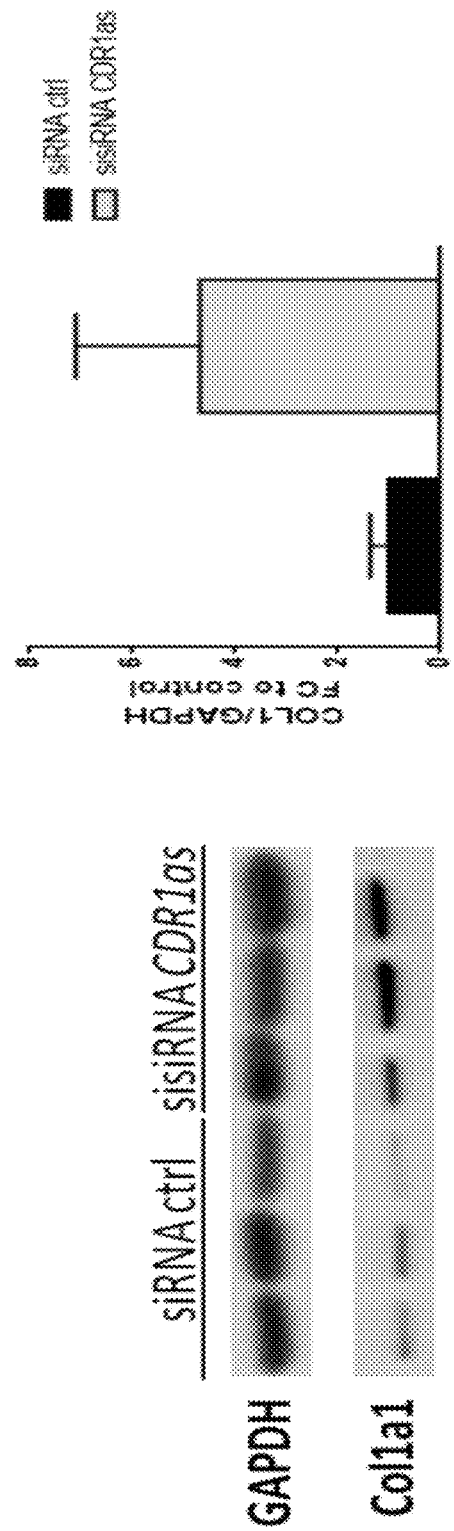

FIG. 24: In vitro study of silencing of CDR1as.

CDR1as is an anti-fibrotic circular RNA: Strand-specific silencing of CDR1as via sisiRNA-chemistry leads to an increase in expression levels of the extracellular matrix component Collagen1a1 in primary HCFs as shown in a representative Western Blot (normalized to GAPDH). Data are depicted as the average of 1 experiment performed in triplicates and represented as mean±SD. *$P<0.05$; $P<0.01$; *$P<0.001$; ****$P<0.0001$. This is described in Example 14.

FIG. 25: In vitro studies of Selenoprotein as a direct target of miR-671-5p.

Selenoprotein P is another direct target of miR-671-5p: A) Predicted consequential pairing of Selenoprotein P target region and miR-671-5p (www.targetscan.org/vert_71/) in humans. B) Validation of miR-671-5p targeting Selenoprotein P assayed by luciferase activity and qRT-PCR (normalized to 18S rRNA) after overexpression of miR-671-5p. Data are depicted as the average of 2-3 independent measurements performed in triplicates and represented as mean±SEM. *P<0.05; P<0.01; *P<0.001; ****P<0.0001. This is described in Example 16.

Figure 26:
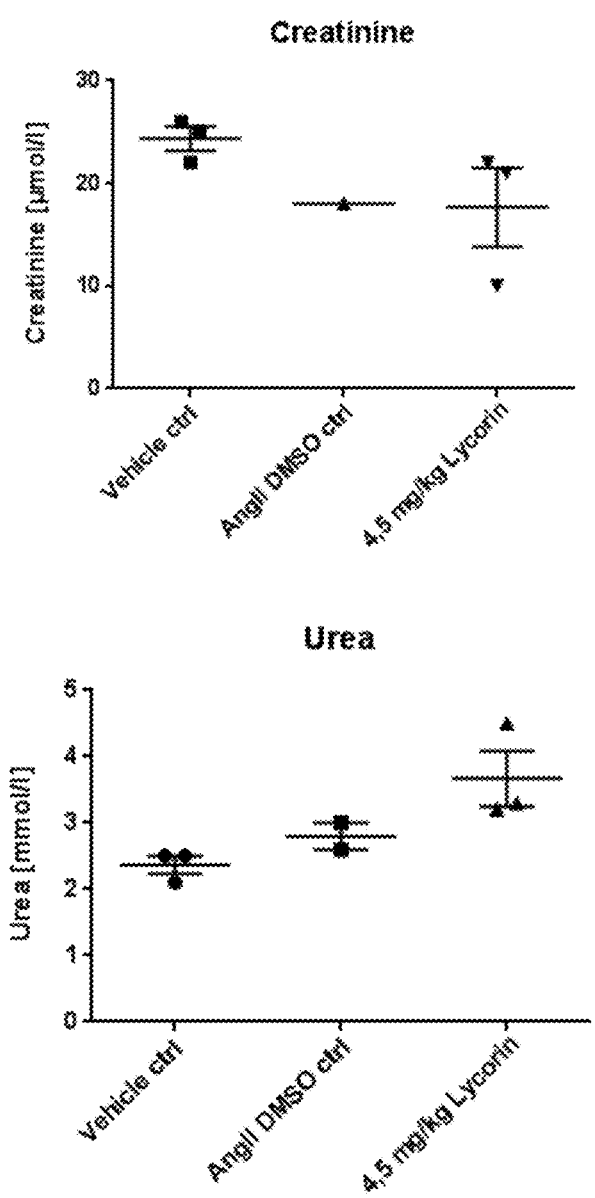
Figure 26:
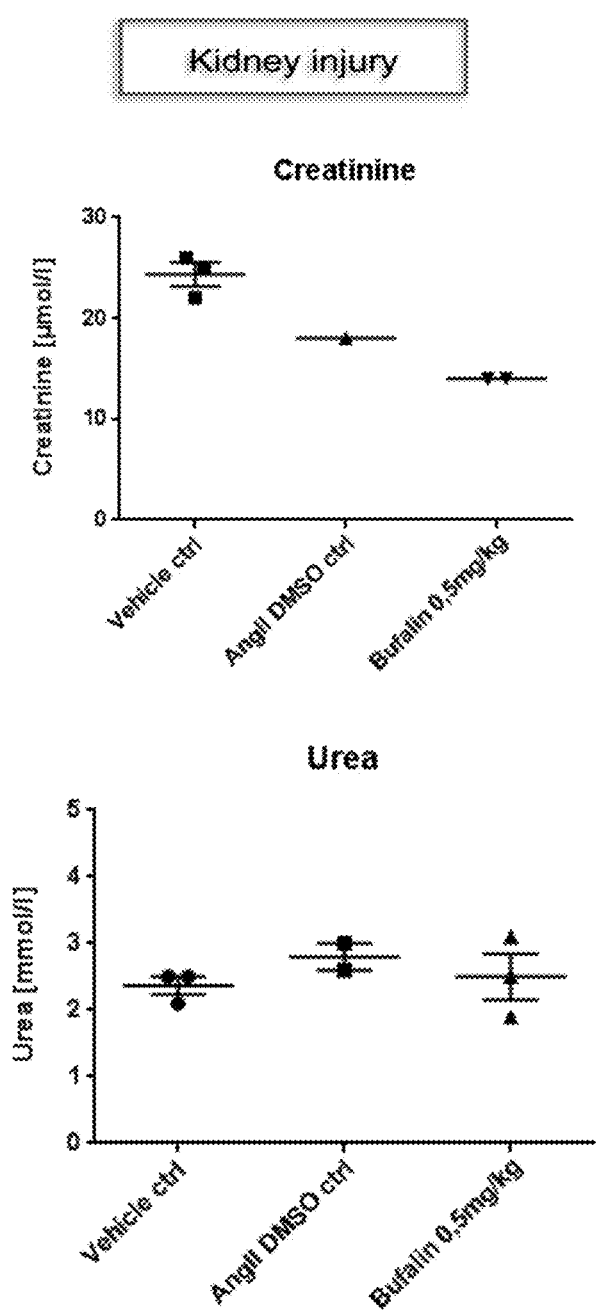

FIG. 26: In vivo studies of Lycorine and Bufalin on liver or kidney.

Administration of Lycorine and Bufalin does not provoke any changes in plasma marker of kidney and liver damage in vivo: Toxicological assessment of Lycorine (A) and Bufalin (B) in a murine model of Angiotensin II-induced HF shows no elevation of plasma marker of kidney and liver damage. Glutamate oxaloacetate transaminase (GOT), Glutamate pyruvate transaminase (GPT) as liver plasma markers and creatinine and urea as kidney markers. Data are represented as mean±SEM. *P<0.05; P<0.01; *P<0.001; ****P<0.0001. This is described in Example 17.

Figure 27:
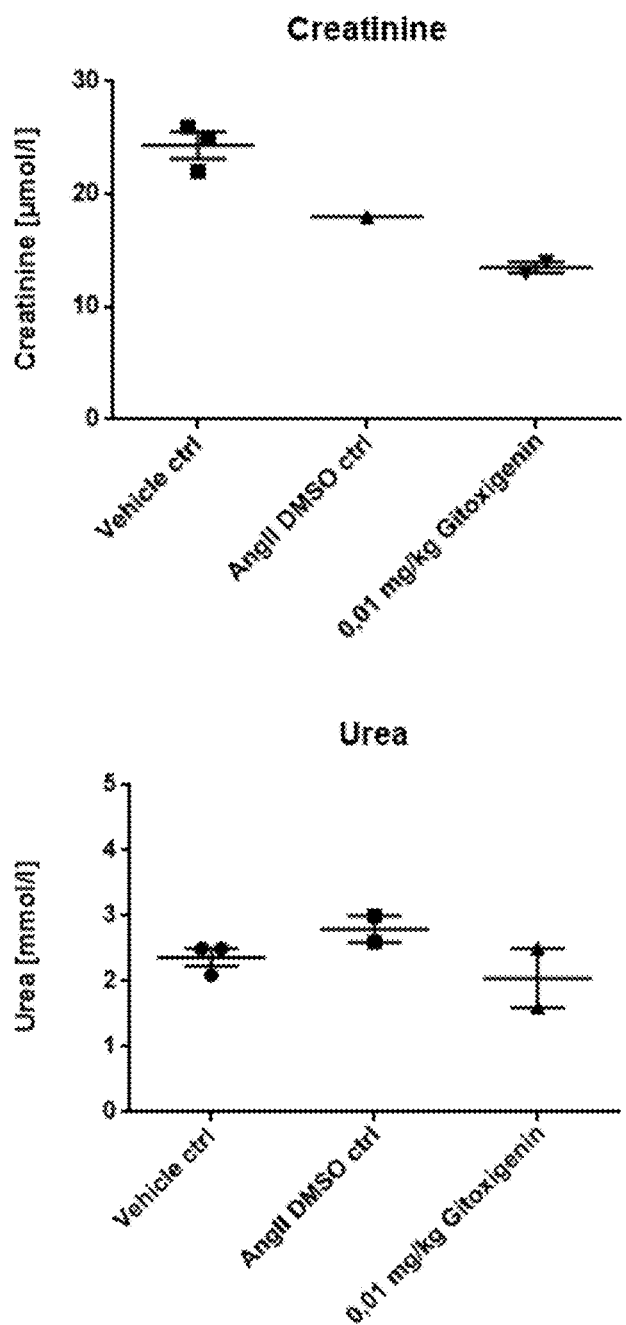

FIG. 27: In vivo studies of Anisomycin and Gitoxigenin on liver or kidney.

Administration of Anisomycin and Gitoxigenin does not provoke any changes in plasma marker of kidney and liver damage in vivo: Toxicological assessment of Anisomycin (A) and Gitoxigenin (B) in a murine model of Angiotensin II-induced HF shows no elevation of plasma marker of kidney and liver damage. Glutamate oxaloacetate transaminase (GOT), Glutamate pyruvate transaminase (GPT) as liver plasma markers and creatinine and urea as kidney markers. Data are represented as mean±SEM. *P<0.05; P<0.01; *P<0.001; ****P<0.0001. This is described in Example 17.

Figure 28:
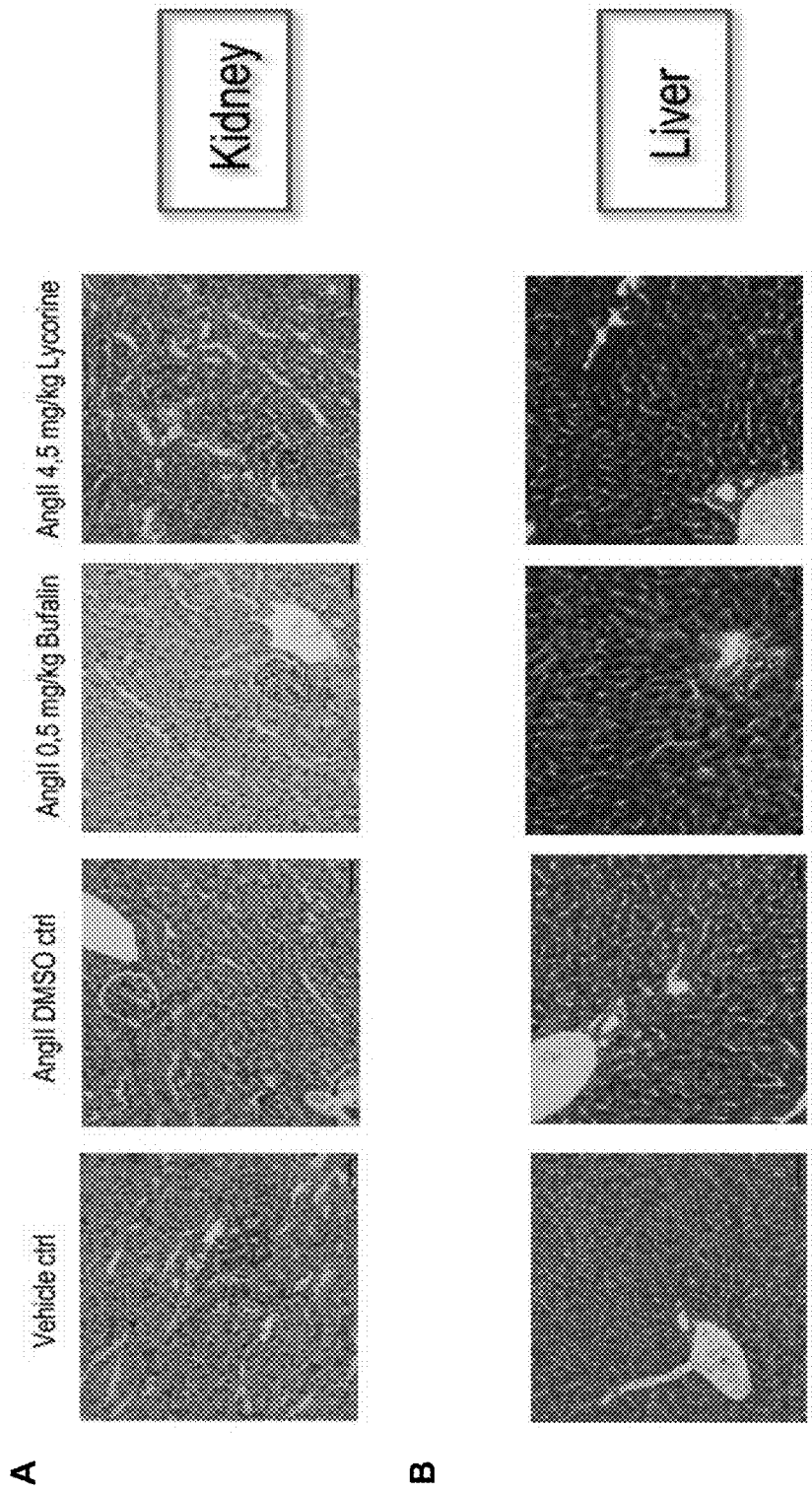

FIG. 28: In vivo studies of Lycorine and Bufalin on liver or kidney.

Administration of Bufalin and Lycorine does not provoke any changes in kidney and liver morphology in vivo: Toxicological assessment of Bufalin and Lycorine in a murine model of Angiotensin II-induced HF does not induce necrosis, inflammation or any morphological changes in kidney (A) and liver (B), respectively. Fourteen days after the operation, kidneys and livers were subjected to histological assessment via Hematoxylin and Eosin (HE) and Periodic acid-Schiff (PAS) stain (n=2-4 per group). Representative image of each group is shown. This is described in Example 17.

Figure 29:
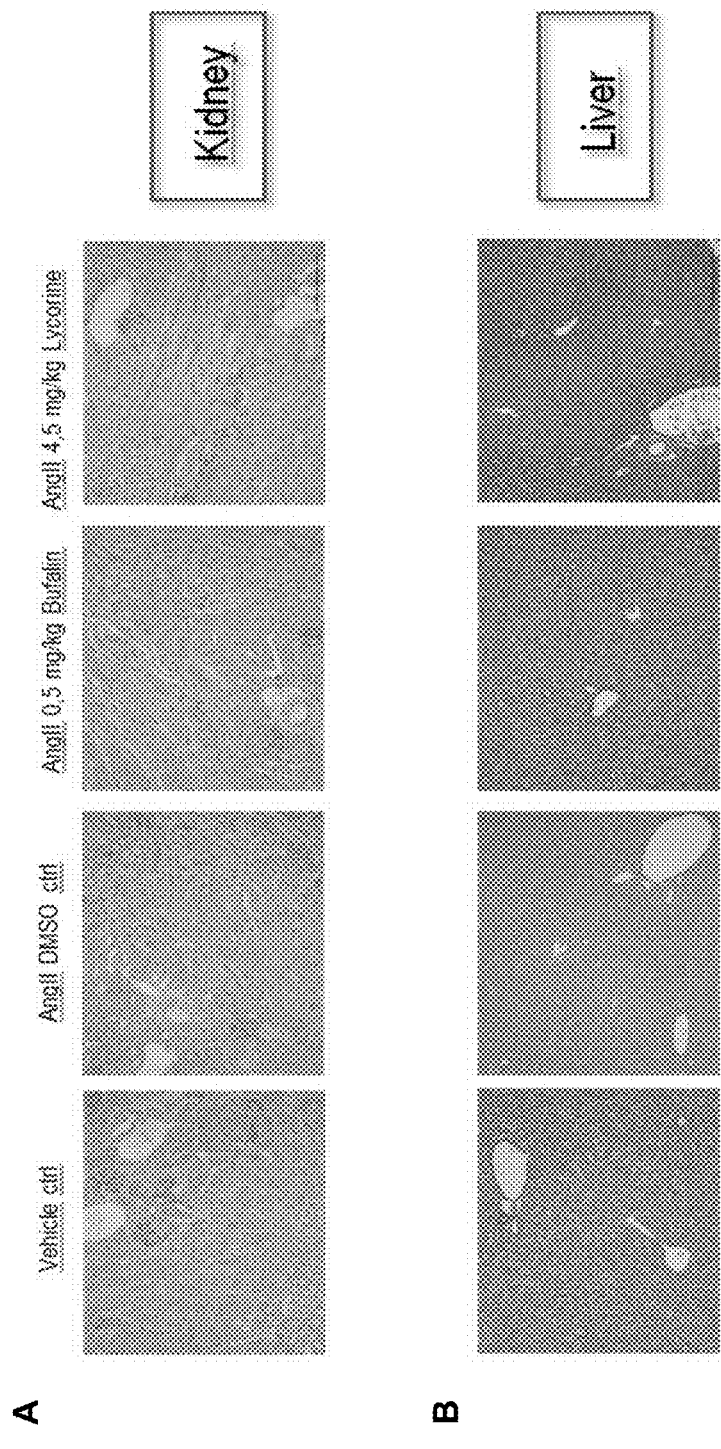

FIG. 29: In vivo studies of Lycorine and Bufalin on liver or kidney (therapeutic approach).

Administration of Bufalin and Lycorine does not provoke any changes in kidney and liver morphology in vivo in mice: Toxicological assessment of Bufalin and Lycorine in the therapeutic approach using a murine model of hypertension-induced HF does not induce necrosis, inflammation or any morphological changes in kidney (A) and liver (B), respectively. Eight weeks after the operation, kidneys and livers were subjected to histological assessment via Hematoxylin and Eosin (HE) and Periodic acid-Schiff (PAS) stain (n=4 per group). Representative image of each group is shown. This is described in Example 18.

Figure 30:
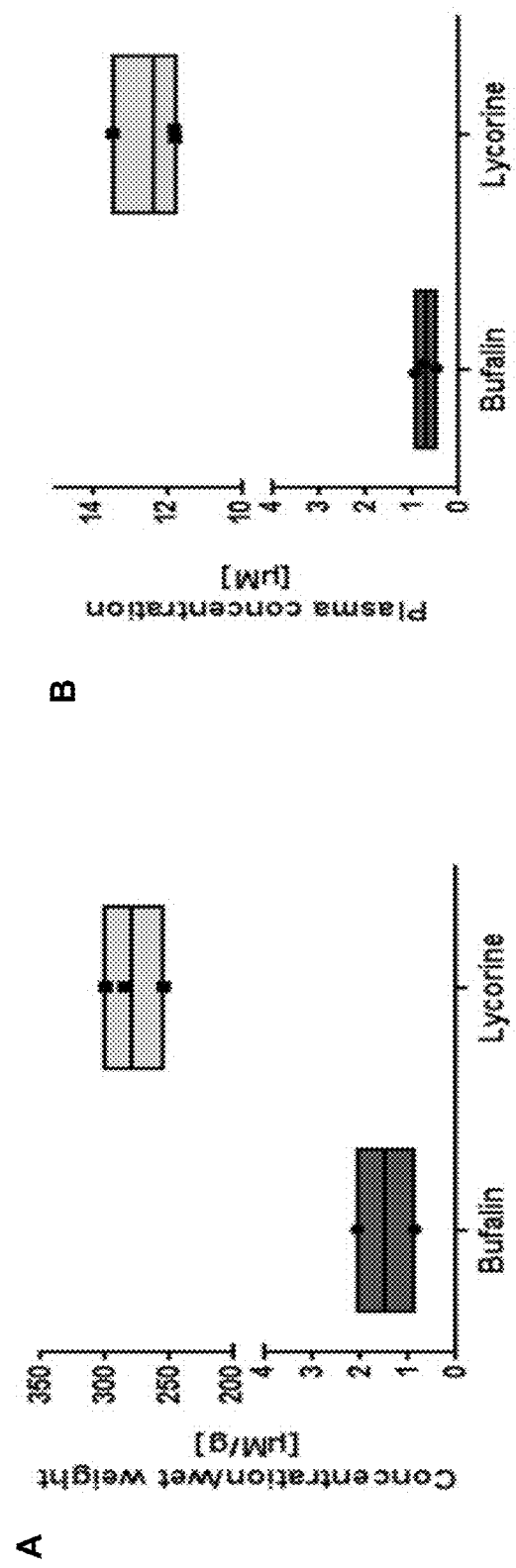

FIG. 30: Evaluation of myocardial and plasma concentrations of Bufalin and Lycorine in vivo.

Bufalin and particularly Lycorine are effectively taken up by the heart, as evidenced by higher levels in (A) the myocardium as compared to (B) the plasma after injections at the respective effective doses. This is described in Example 19.

Figure 31:
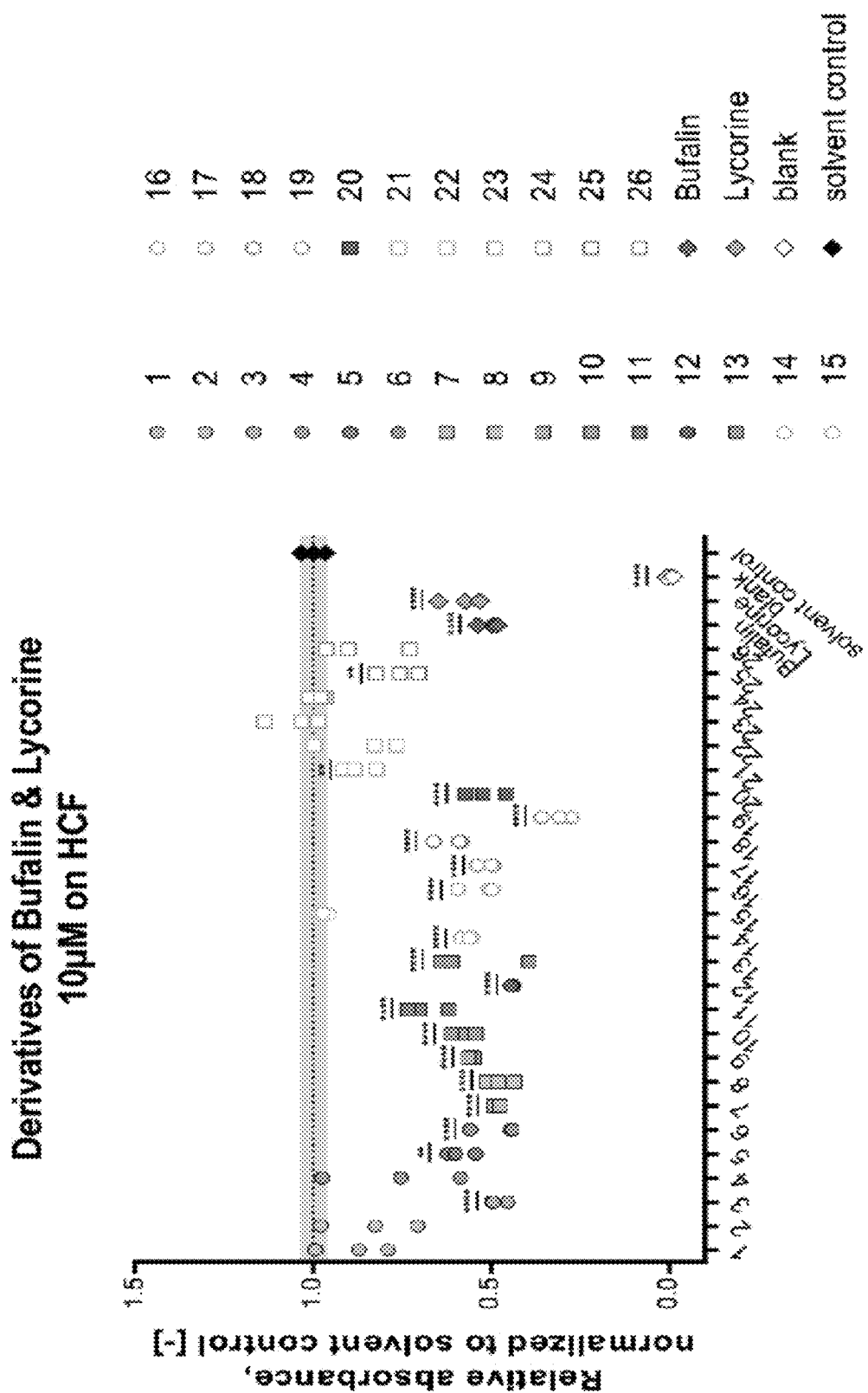

FIG. 31: Screening of chemical derivatives of Bufalin and Lycorine in vitro.

Effects of 26 chemical derivatives of Bufalin (derivatives 3, 5, 6, 7, 8, 9, 10, 11, 12, 13, 14, 16, 17, 18 and 25) and Lycorine (derivative 1, 2, 4, 15, 19, 20, 21, 22, 23, 24 and 26) (10 µM) on the proliferation of human cardiac fibroblasts (HCFs). Solvent control refers to DMSO. This is described in Example 20.

Figure 32:
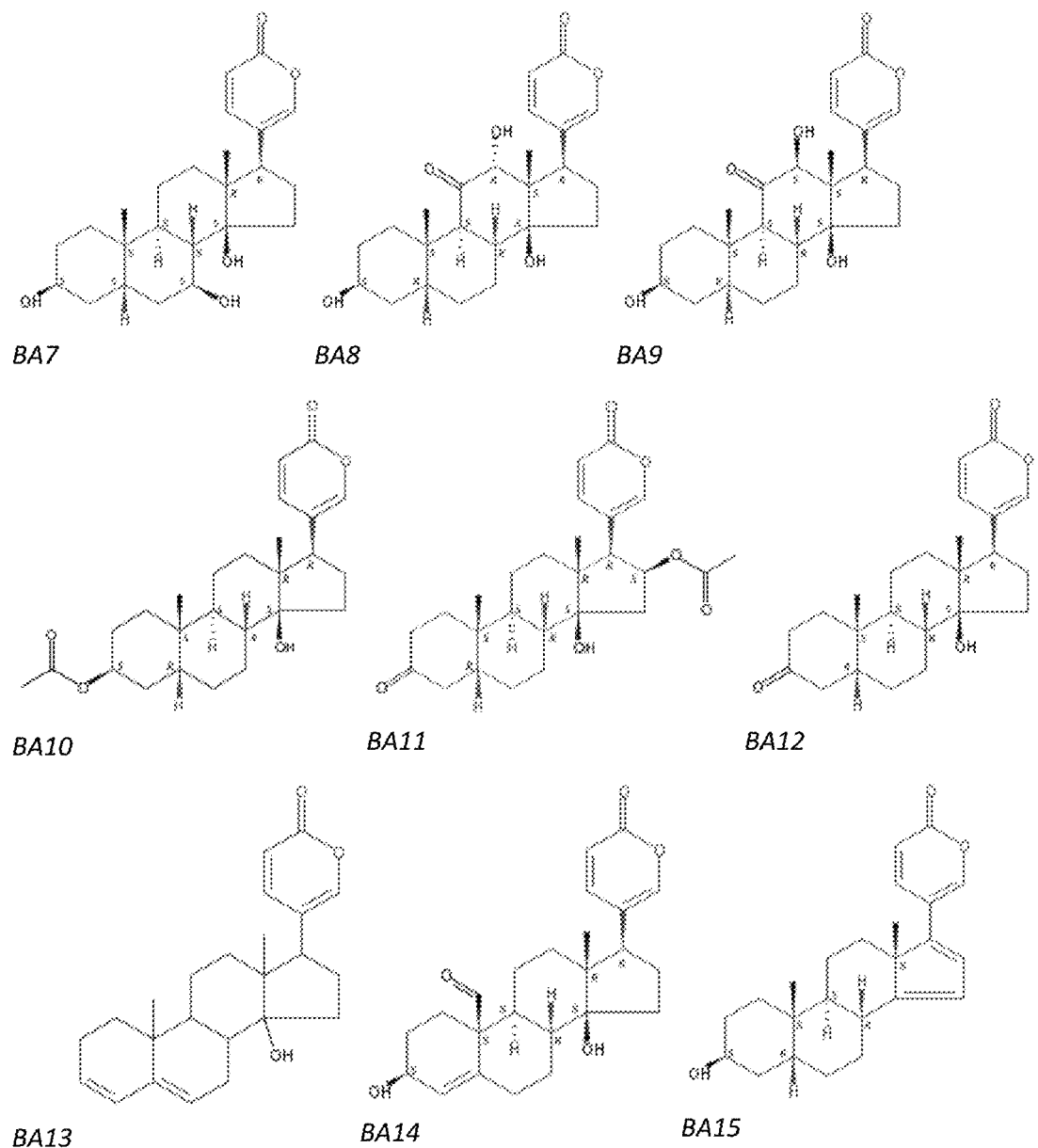
Figure 32:
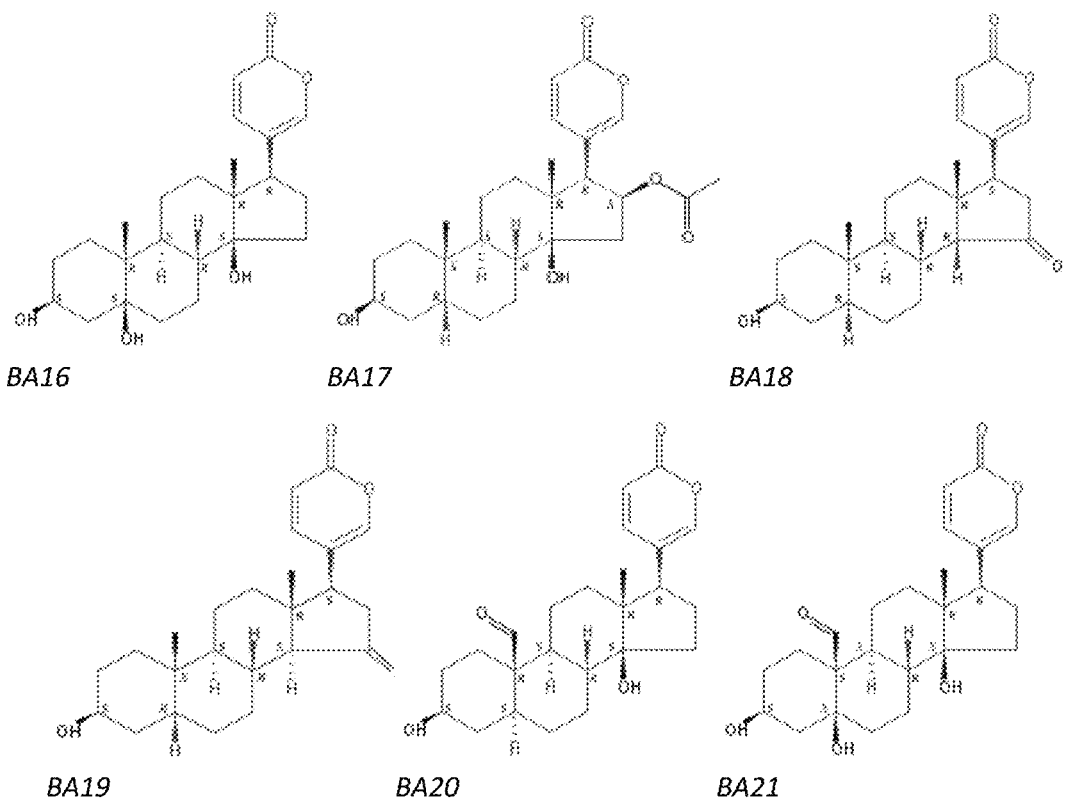
Figure 32:
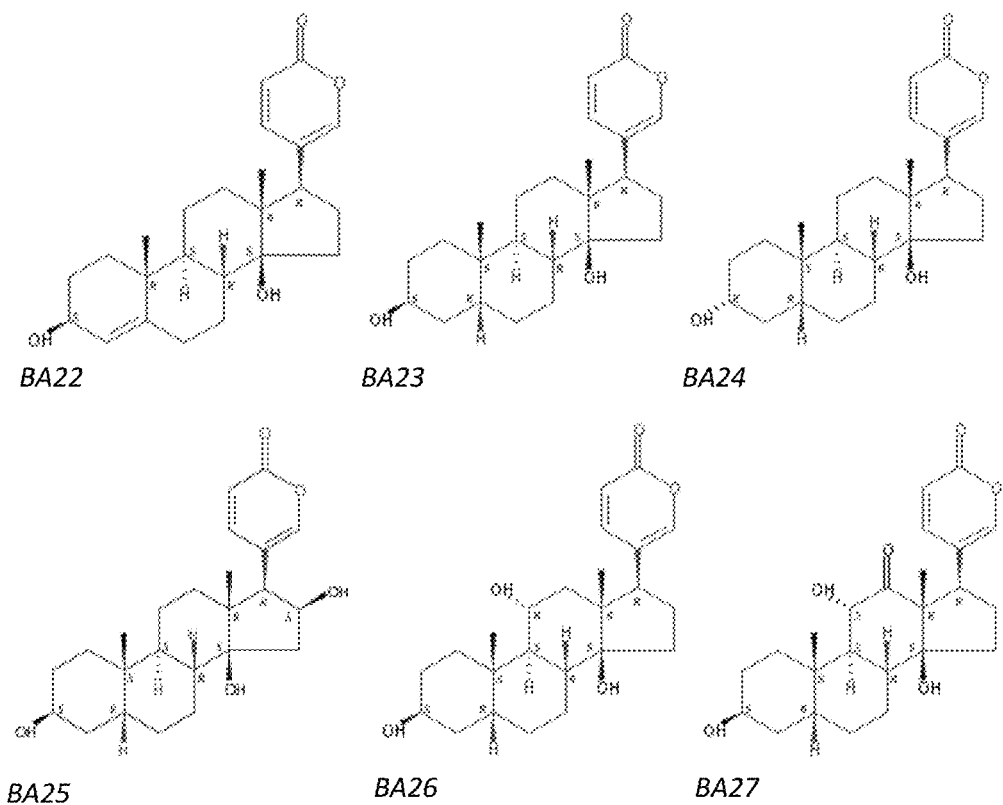

FIG. 32: Bufalin and analogs thereof.

A) Bufalin structure is illustrated. B) Structures of Bufalin analogs are depicted. Only aglycone analogs are shown in (B).

Figure 33:
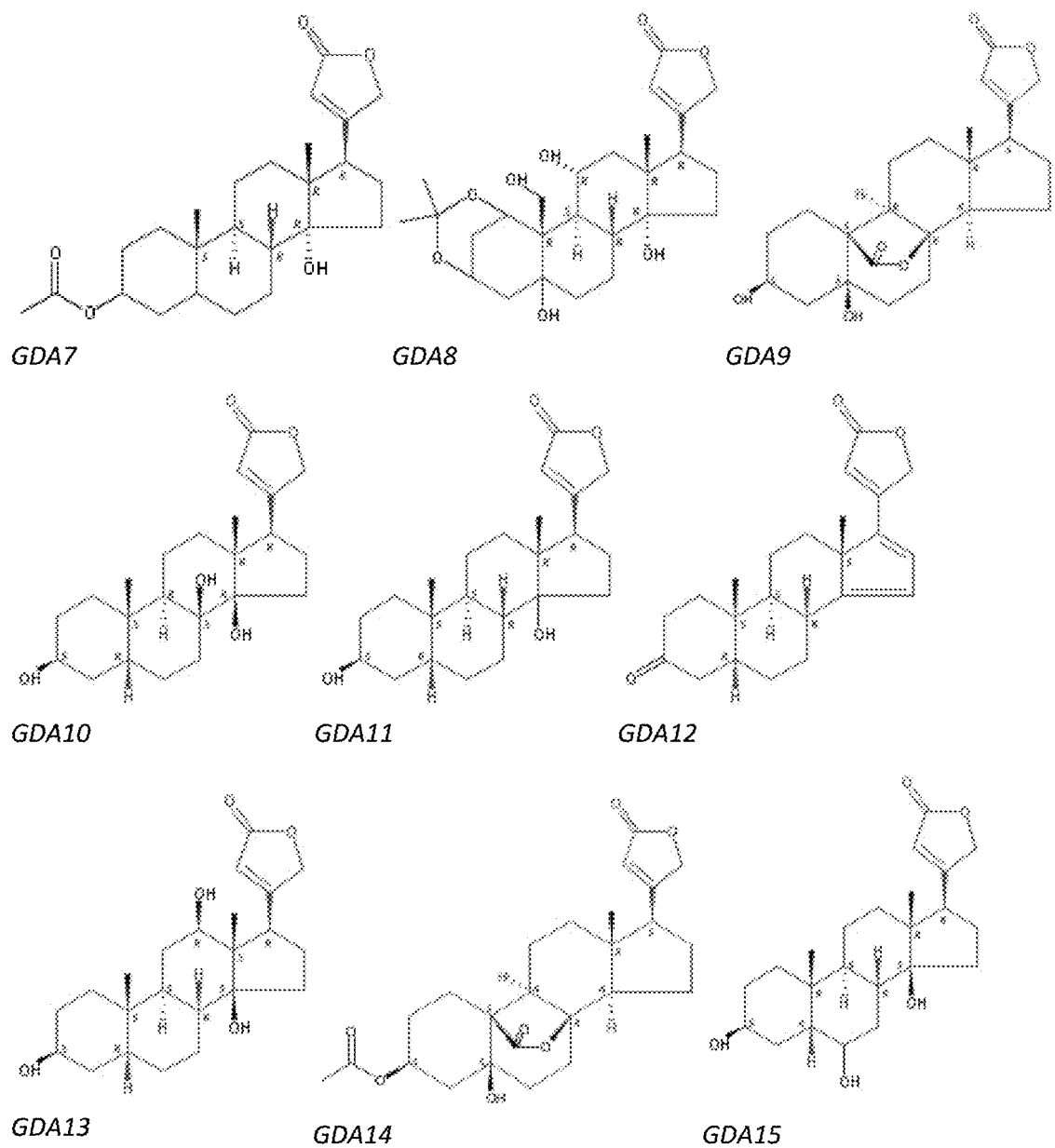
Figure 33:
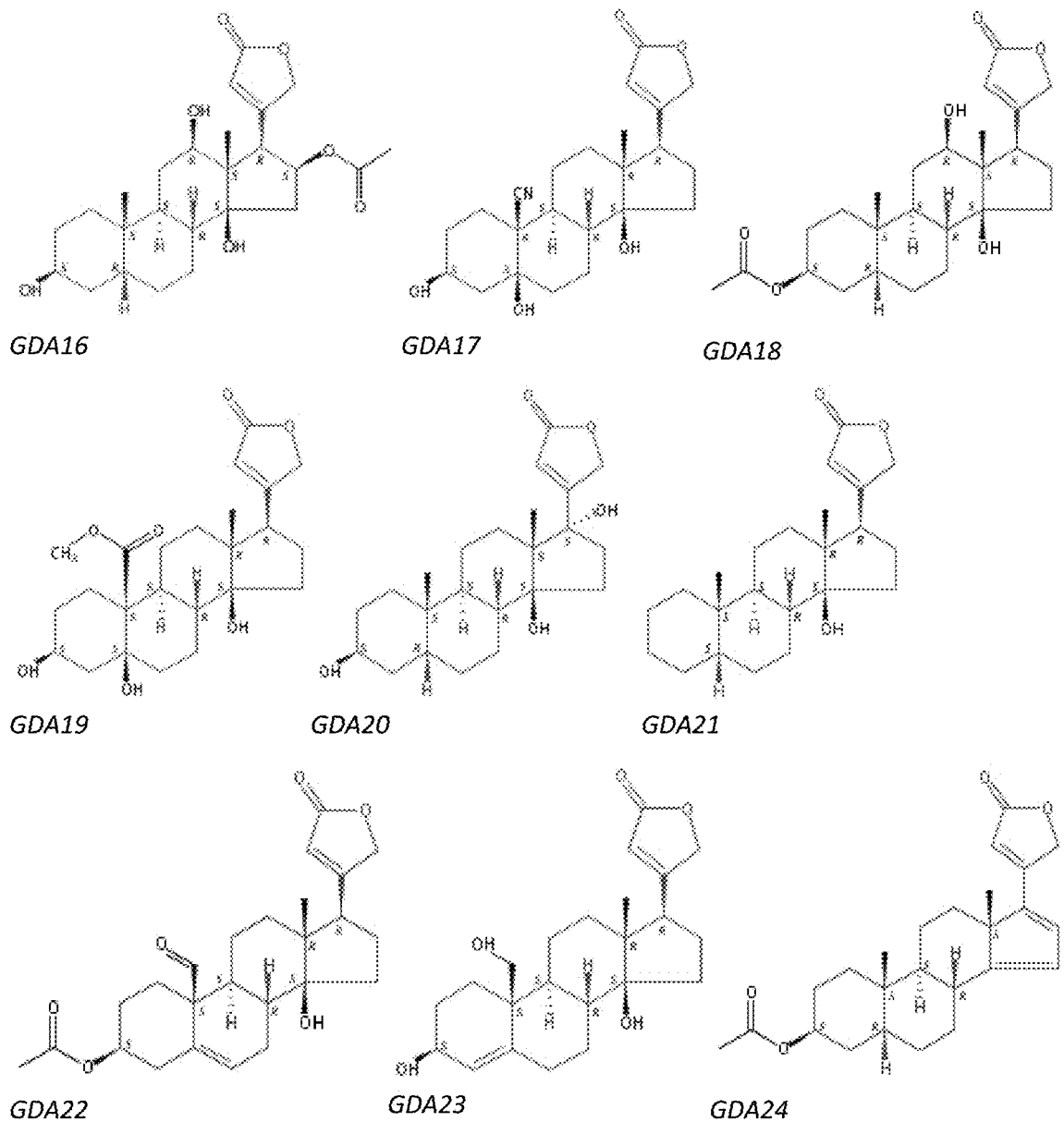
Figure 33:
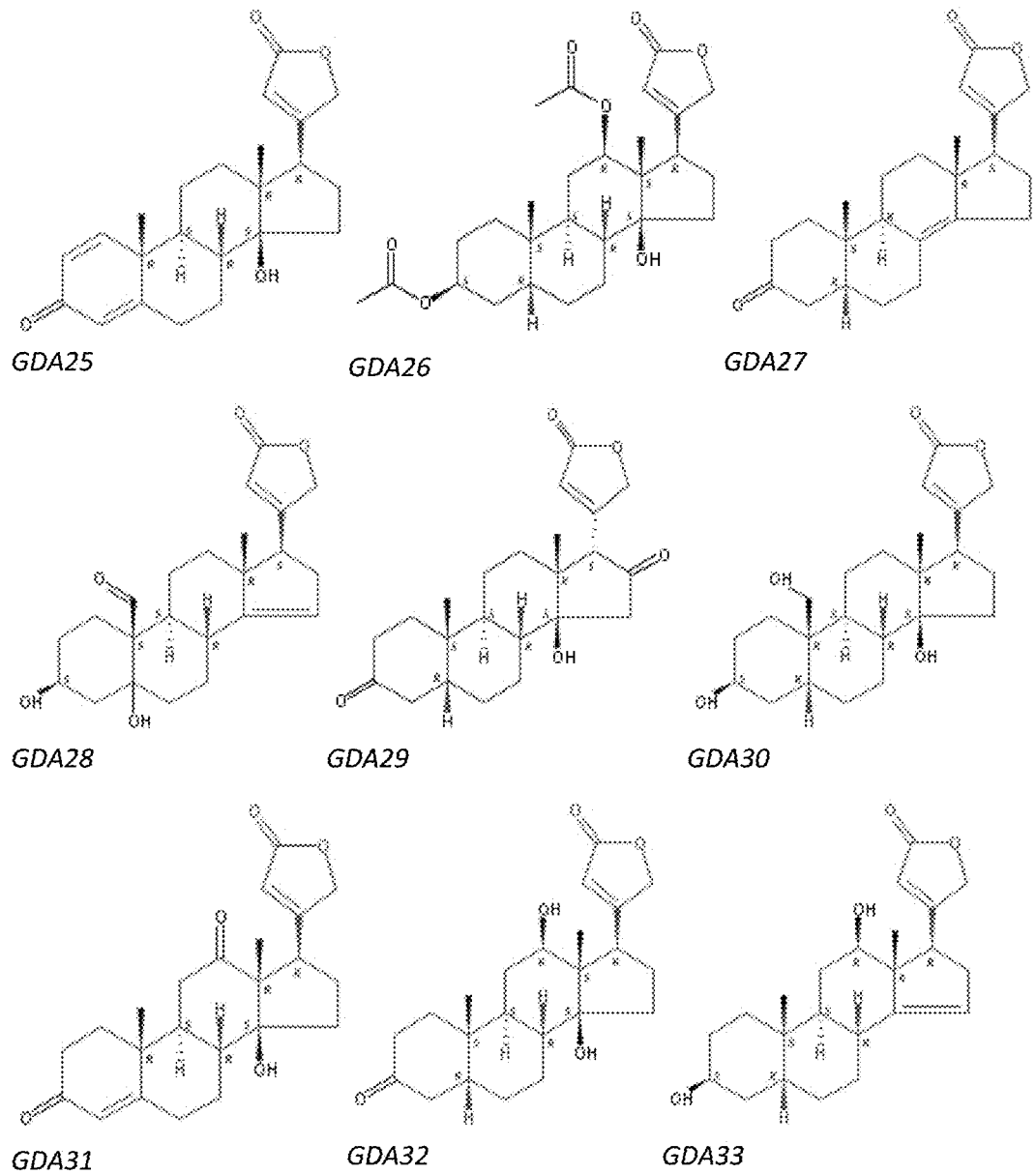
Figure 33:
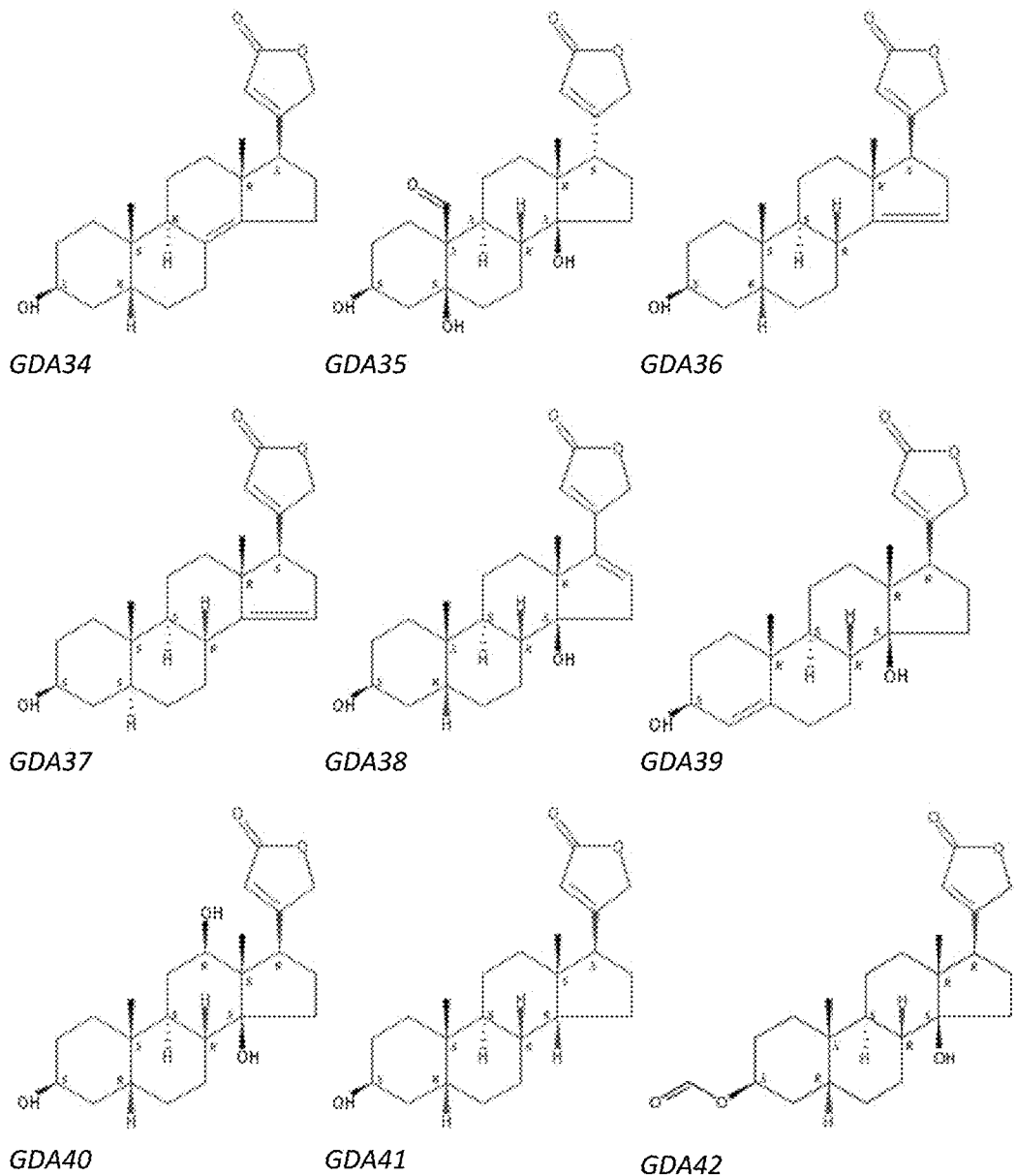
Figure 33:
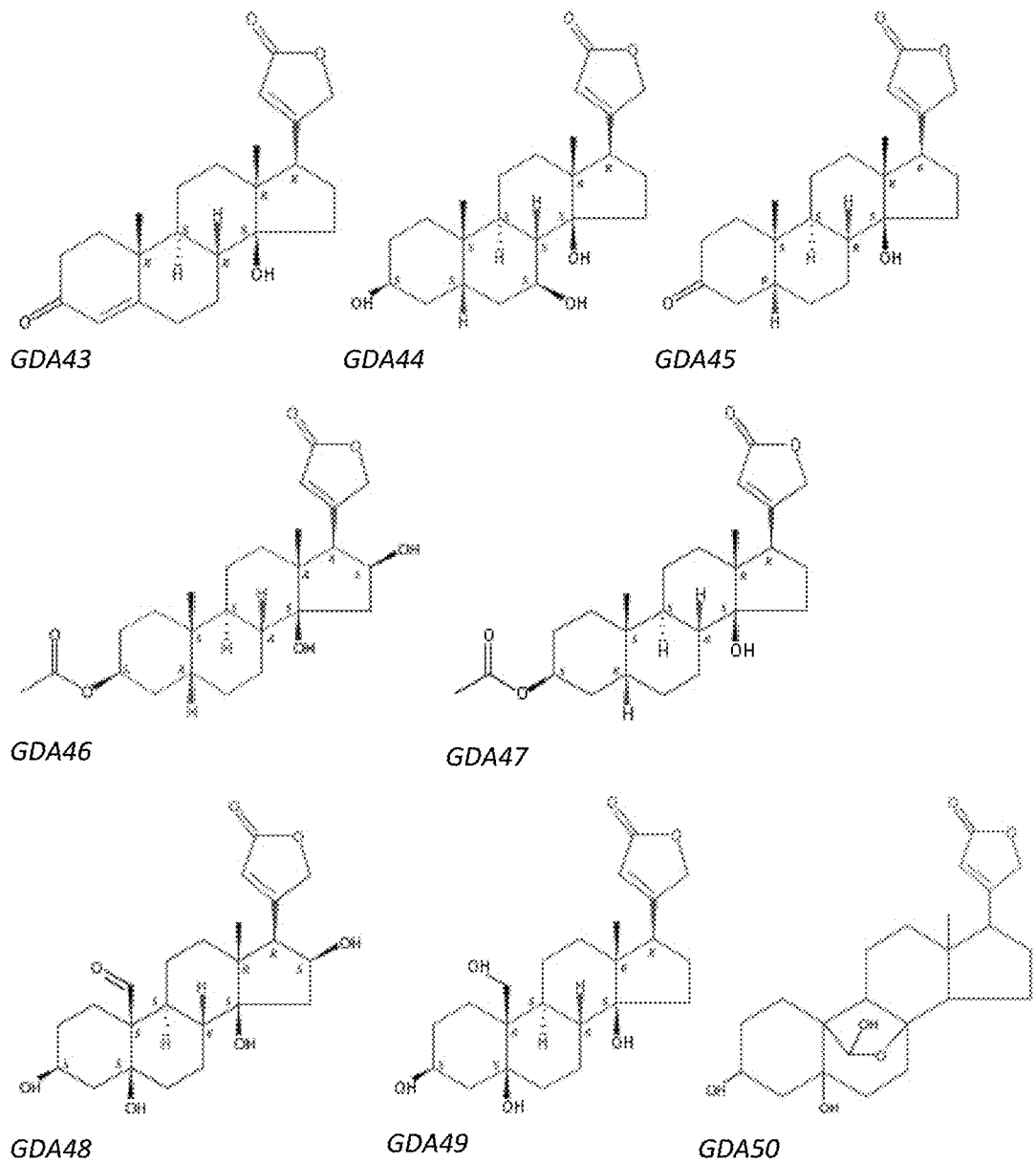
Figure 33:
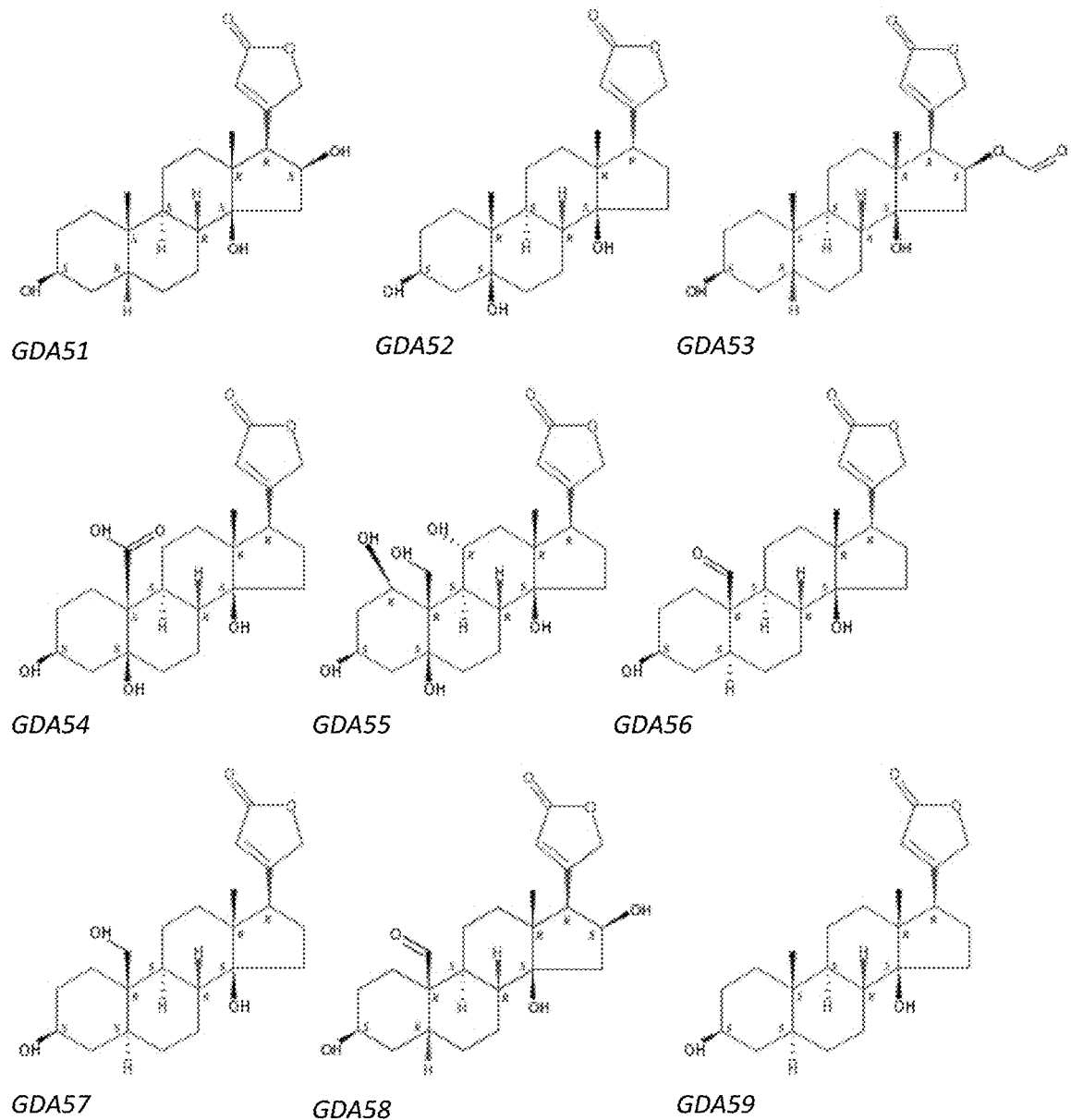
Figure 33:
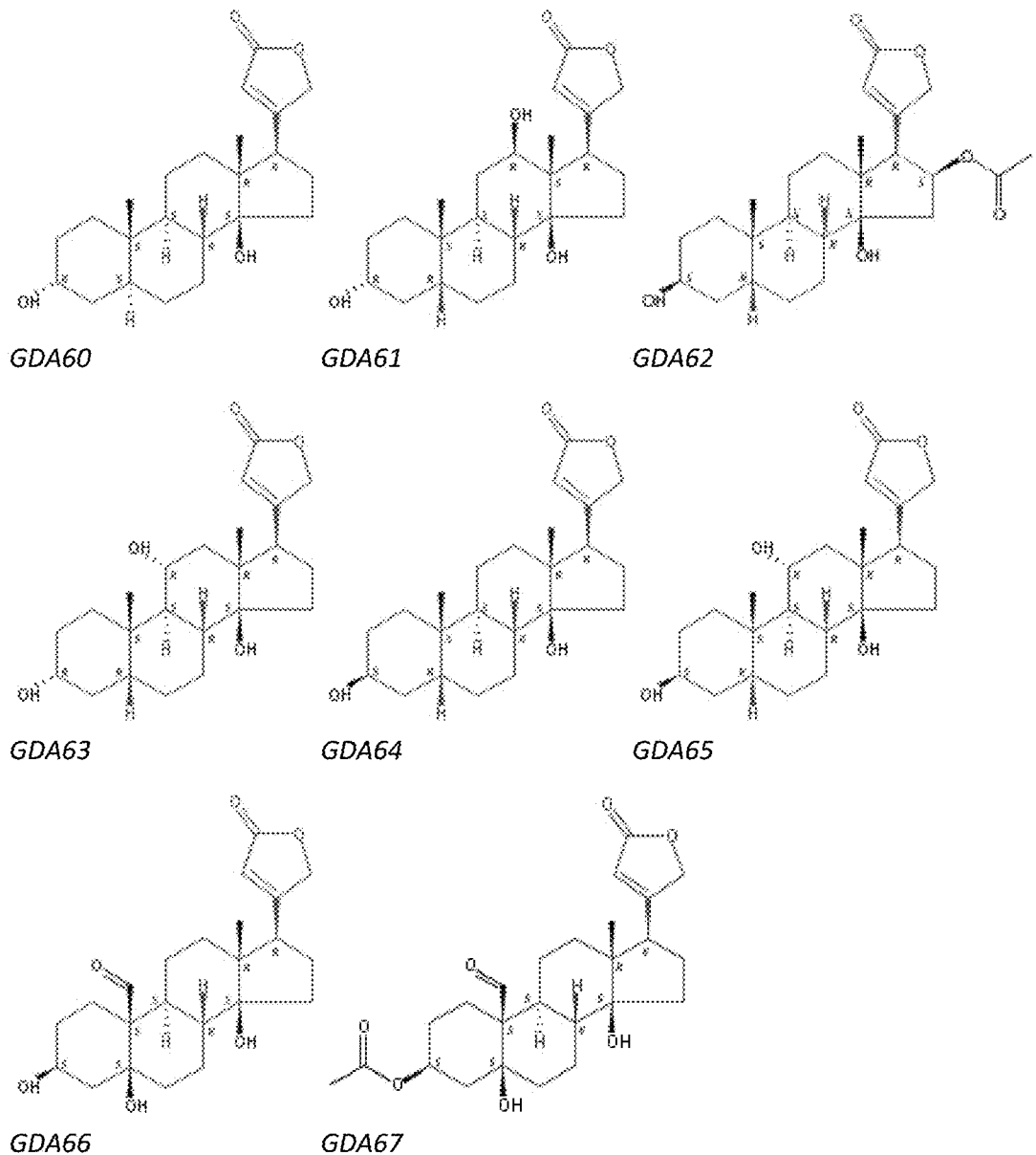

FIG. 33: Gitoxigenin and analogs thereof.

A) Gitoxigenin structure is illustrated. B) Structures of Gitoxigenin analogs are depicted as well as structures of Digitoxigenin analogs. Only aglycone analogs are shown in (B).

Figure 34:
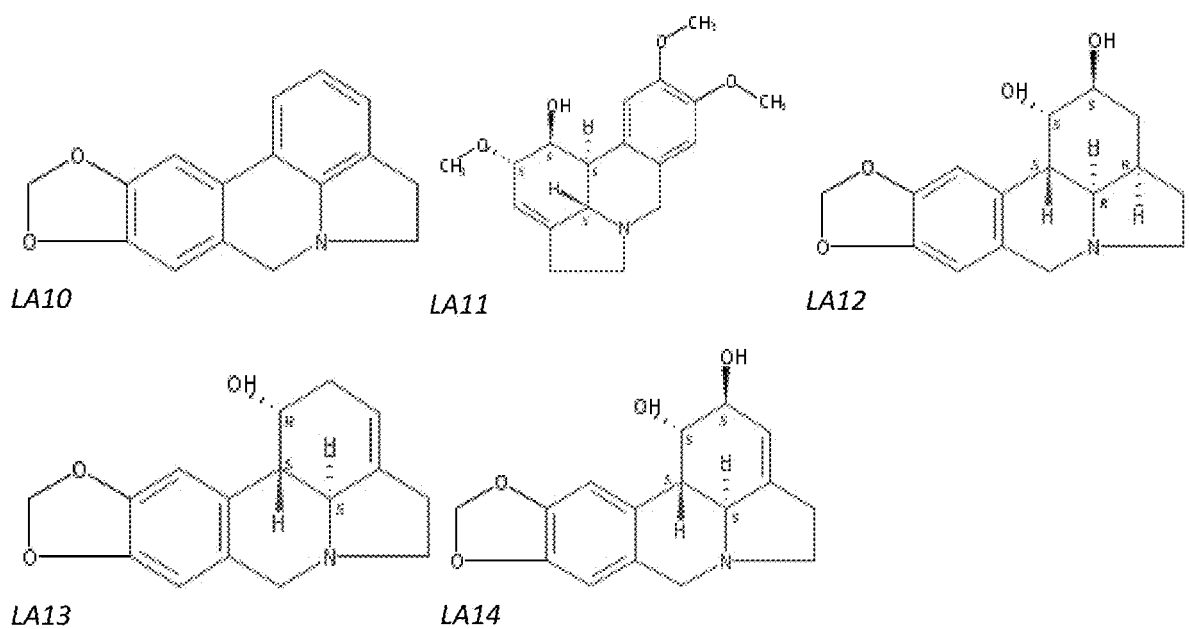

FIG. 34: Lycorine and analogs thereof.

A) Lycorine structure is illustrated. B) Structures of Lycorine analogs are depicted.

Figure 35:
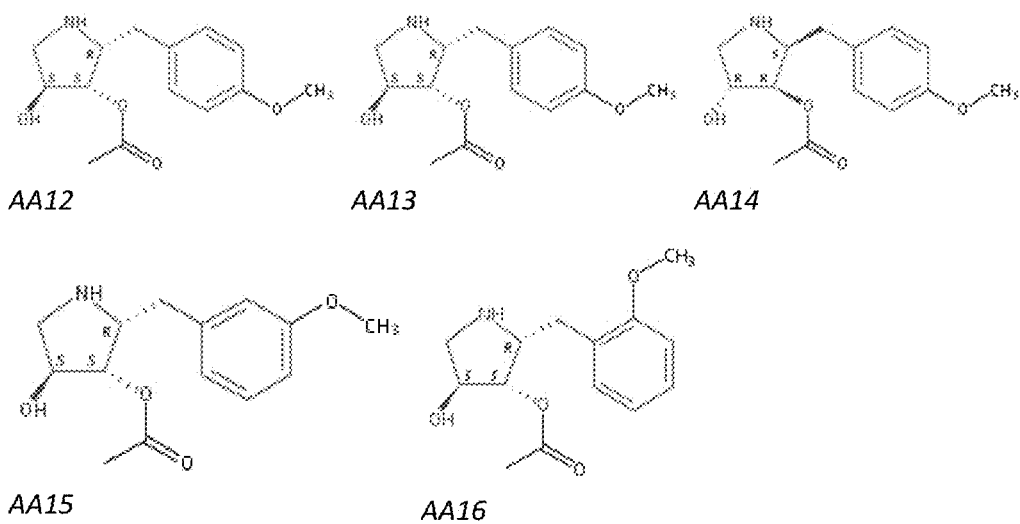

FIG. 35: Anisomycin and analogs thereof.

A) Anisomycin structure is illustrated. B) Structures of Anisomycin analogs are depicted.

Figure 36:
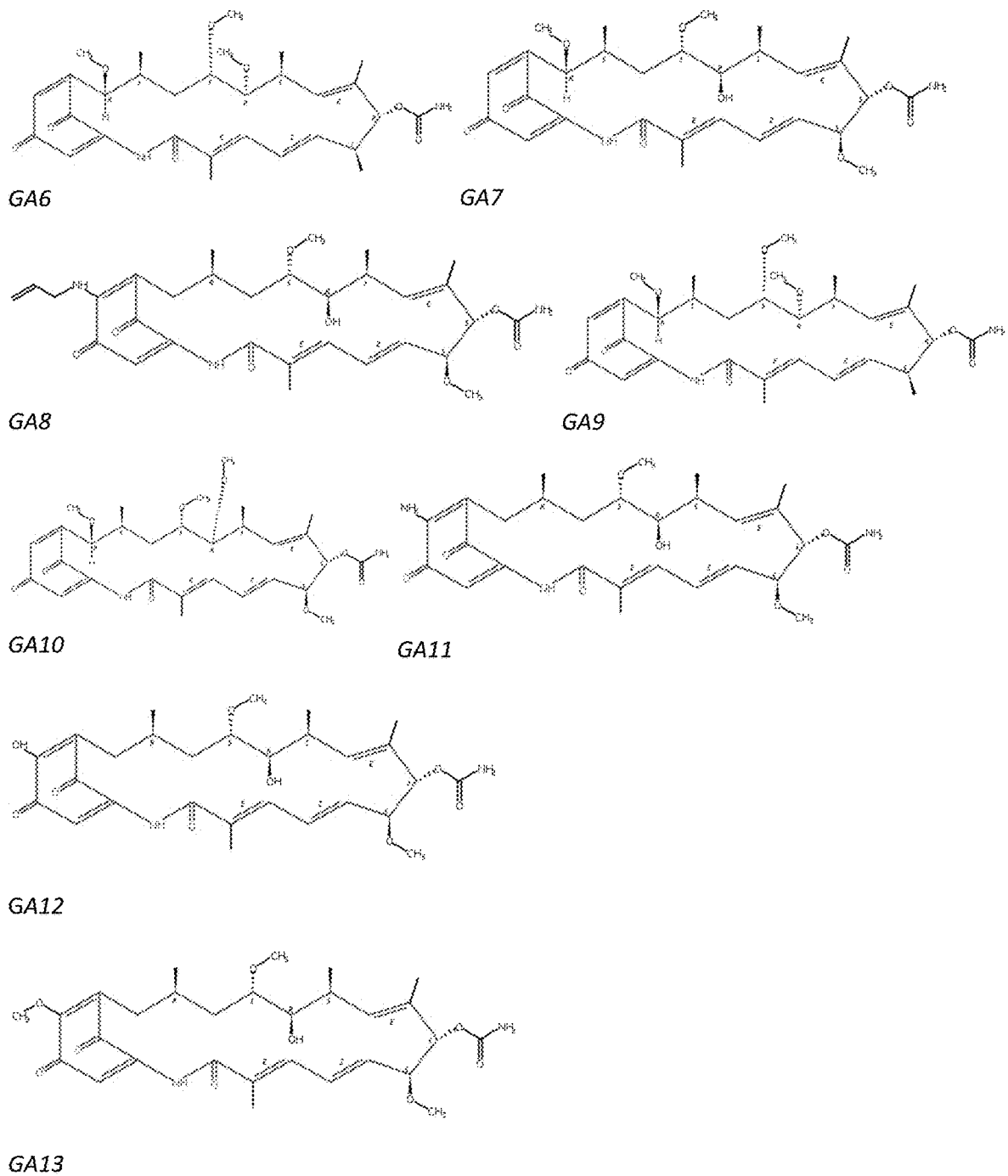

FIG. 36: Geldanamycin and analogs thereof.

A) Geldanamycin structure is illustrated. B) Structures of Geldanamycin analogs are depicted.

FIG. 37: Chemical derivatives of Lycorine.

Chemical derivatives of Lycorine are depicted herein.

Figure 38:
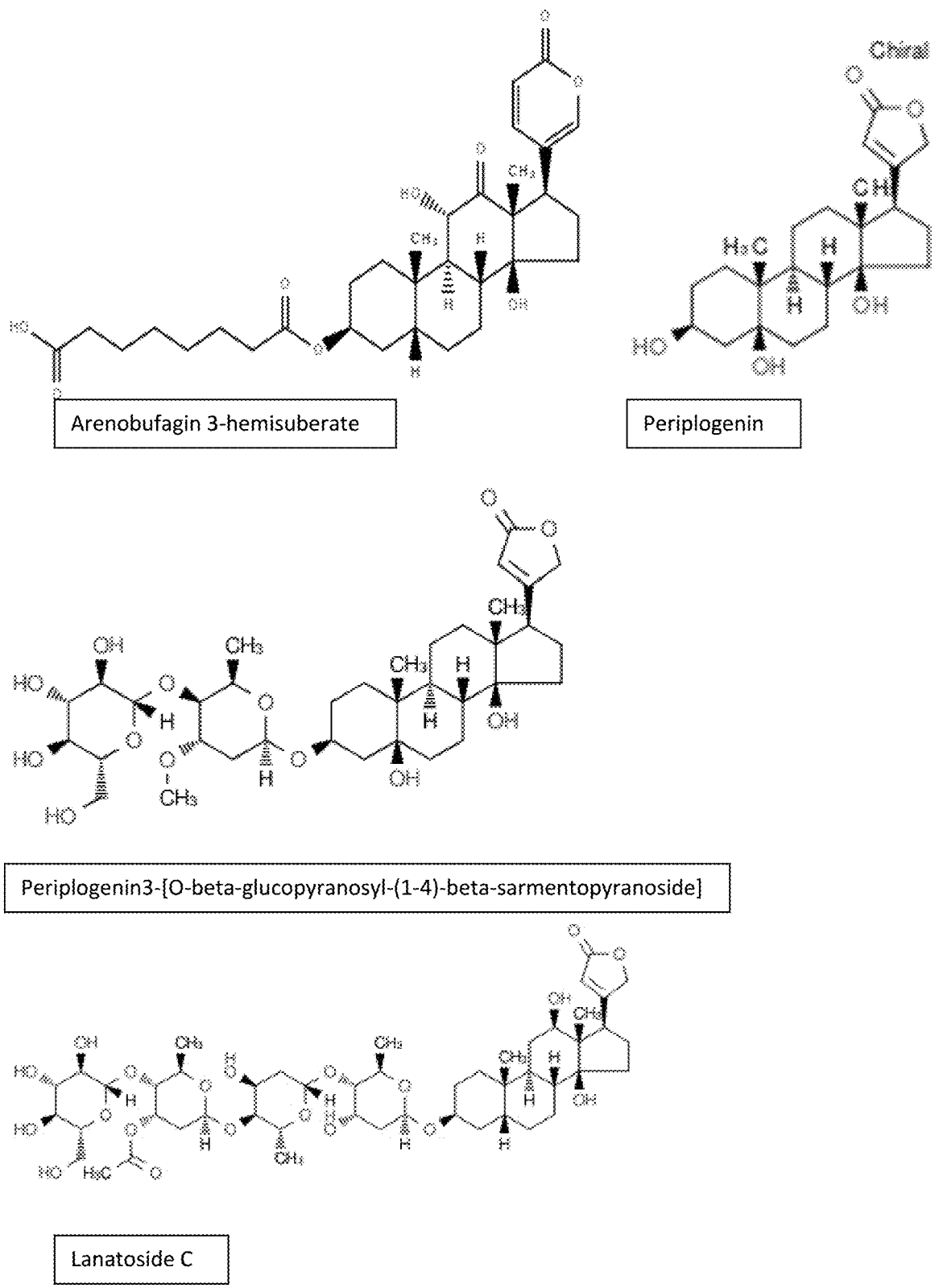
Figure 38:
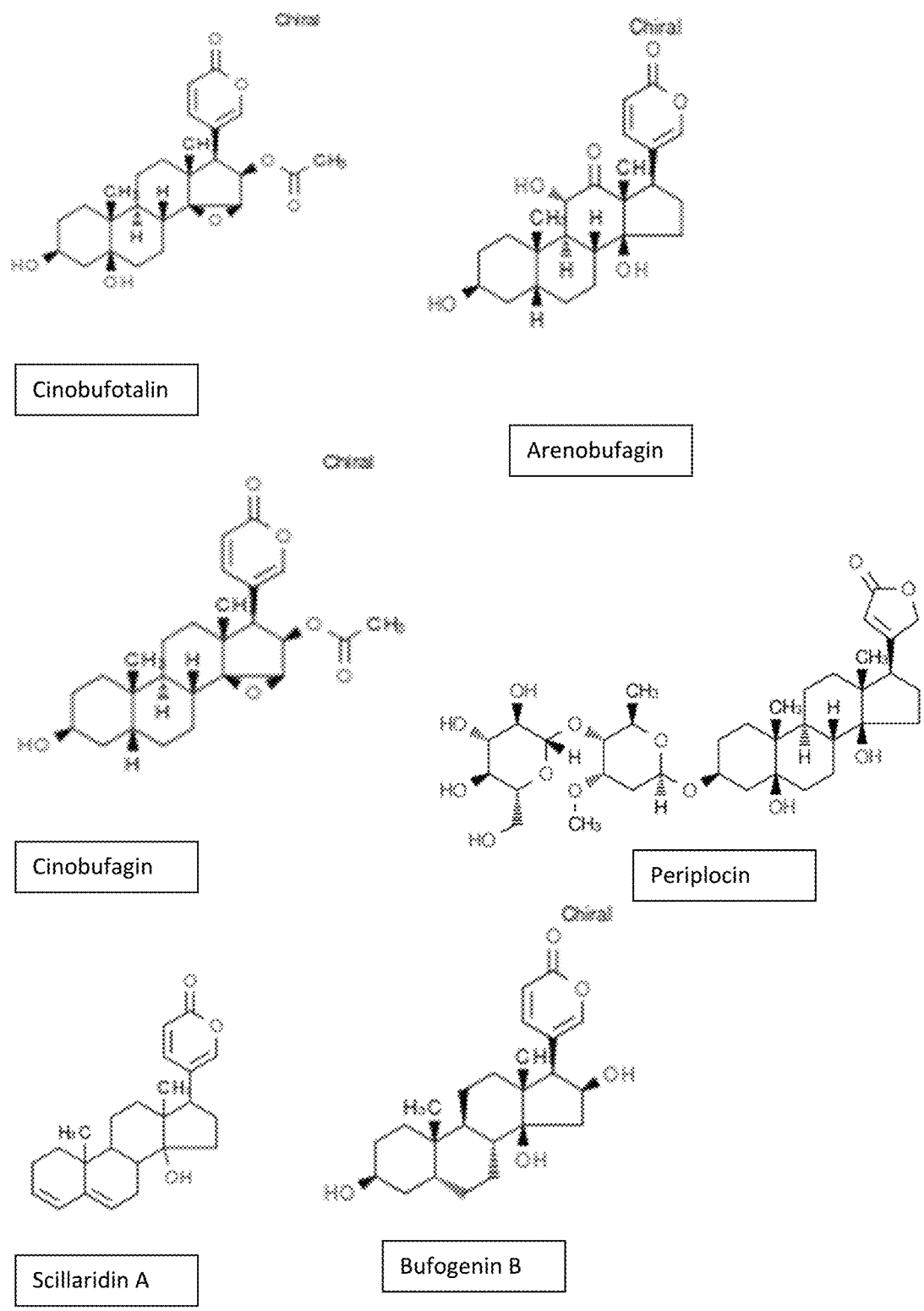

FIG. 38: Chemical derivatives of Bufalin.

Chemical derivatives of Bufalin are depicted herein.

Figure 39:
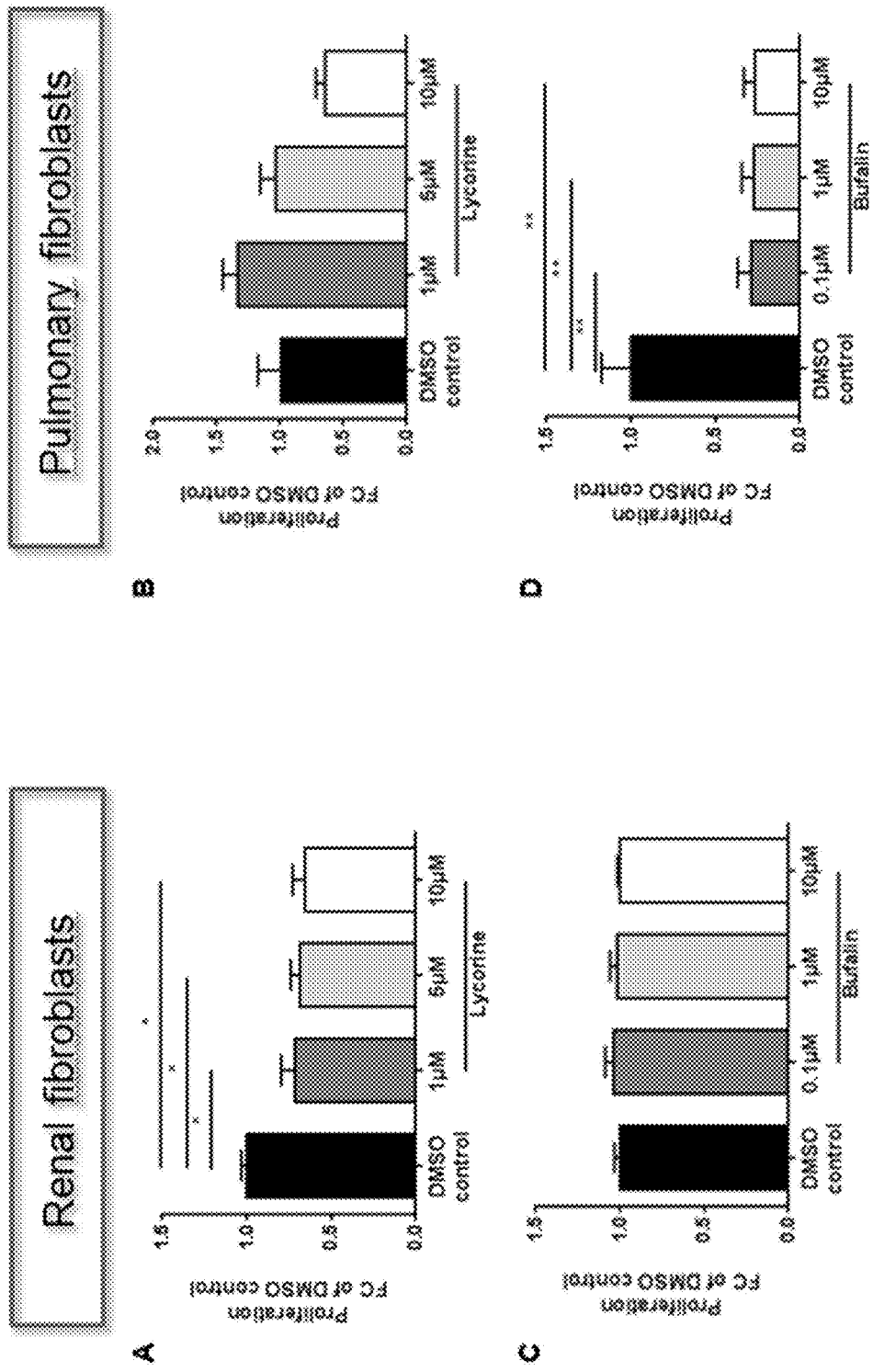

FIG. 39: In vitro assessment of Bufalin and Lycorine on non-cardiac fibroblasts.

Dose-dependency of proliferation-inhibitory effects of lycorine was evident (A) in the rat renal fibroblast cell line NRK49F, whereas bufalin potently inhibited the proliferation of (D) primary human pulmonary fibroblasts (HPFs). DMSO refers as control. Data are represented as mean±SEM. *P<0.05; P<0.01; *P<0.001; ****P<0.0001. This is described in Example 21.

DETAILED DESCRIPTION OF THE INVENTION

The object of the present invention is to provide a compound for use in a method of preventing or treating fibrosis.

A functional screen of 480 natural compounds that were selected for a maximum of chemical diversity was performed in vitro in primary human cardiac fibroblasts (HCFs) to see which compounds led to an altered expression of miRNAs. Hits obtained in this screen were further tested for their capacity to decrease proliferation of HCFs in a dose-dependent manner as measured by BrdU-ELISA, yielding the five most successful compounds Bufalin, Gitoxigenin, Lycorine, Anisomycin and Geldanamycin. Next, an in vivo mouse model of diastolic heart failure was used to test the compounds Bufalin, Gitoxigenin, Lycorine, Anisomycin demonstrating that these compounds ameliorate cardiac fibrosis. For in vivo therapeutic approach using a mouse model, the focus was drawn to Bufalin and Lycorine. Further, Bufalin and Lycorine were also tested on pulmonary fibroblasts and renal fibroblasts demonstrating that those compounds also ameliorate lung and kidney fibrosis.

Bufalin and Gitoxigenin are cardiac glycosides, Lycorine is an alkaloid and Anisomycin and Geldanamycin are antibiotics.

According to Prassas and Diamandis (2008), cardiac glycosides play further potential therapeutic roles in various human diseases, such as cancer. Additionally, cardiac glycosides may also act as possible therapeutics in the context of ischaemic stroke. Data also reveal potential applications of these compounds for treating cystic fibrosis. Cardiac glycosides have been identified as a diverse family of naturally derived compounds capable of binding to and inhibiting Na+/K+-ATPase, which is a ubiquitous membrane protein using energy derived from ATP hydrolysis to perform the transport of potassium ions into the cell and on the other hand sodium ions out of the cell. An inhibition of said Na+/K+-ATPase increases the level of sodium ions in cardiac myocytes, leading to an increase of calcium level and cardiac contractile force.

Bufalin itself belongs to the group of Bufadienolide and refers to a cardiotonic steroid isolated from the Chinese toad venom. It exhibits an antitumor effect against various malignancies. In vitro, Bufalin shows anti-proliferative and/or apoptotic effects of cancer cells in prostate or leukaemia cancer types (Prassas and Diamandis 2008).

Gitoxigenin structurally belongs to the group of Cardenolides and is isolated from the foxglove Digitalis lanata. It was found that Gitoxigenin exhibits anticancer activities and was already tested in cancer cell lines of breast cancer indicating anti-proliferative effects. The "generic" scaffold of Gitoxigenin derived from Digitoxigenin, which is the more general compound in the literature and also shows anticancer effects, such as anti-proliferative effects in renal or myeloma cancer cell types (Presses and Diamandis 2008). In FIGS. 32 and 33 analogs of Bufalin and Gitoxigenin, but also Digitoxigenin are illustrated. These figures only include aglycones, since the active forms are most likely the aglycones. Besides Bufalin, Gitoxigenin and Digitoxigenin analogs, stereoisomers of said analogs are disclosed in the present invention as well.

Lycorine refers to the most abundant alkaloid isolated from Amaryllidaceae family of plants. Known in the art, Lycorine has promising anticancer activities, but also other diverse biological properties, such as antiplasmodial, antitrypanosomal, anti-inflammatory, analgesic, and emetic properties. Further, Lycorine and its derivatives and analogs are also capable of inhibiting several virus species, including severe acute respiratory syndrome-associated coronavirus, herpes simplex virus and poliovirus (Guo et al. 2016 and Wang et al. 2014). The analog structures of Lycorine are illustrated in FIG. 34. Besides analogs, stereoisomers of Lycorine analogs are disclosed in the present invention as well.

According to Grollmann (1967) Anisomycin is an antibiotic which is isolated from Streptomyces griseolus and is able to inhibit eukaryotic protein synthesis. Protein synthesis as well as partially DNA synthesis is due to inhibition of peptidyl transferase or the 80S ribosome system.

According to Schulte et al. (1998) Geldanamycin was identified as a benzoquinone ansamycin, a class of naturally occurring antibiotics and was originally discovered in the organism Streptomyces hygroscopicus. It acts as an inhibitor of the Heat Shock Protein Hsp90 by binding to the ATP/ADP binding site in the amino terminus of the protein that is specific of regulating the Hsp90 conformation. Hsp90 can only be bound by drugs exhibiting the benzoquinone ansamycin moiety. The analogs of Anisomycin and Geldanamycin are illustrated in FIGS. 35 and 36. Besides analogs, stereoisomers of Anisomycin and Geldanamycin analogs are disclosed in the present invention as well.

As mentioned above, an in vitro method of identifying an anti-fibrotic compound was used in the present invention. First, a functional screen of 480 natural compounds was performed in vitro in primary human cardiac fibroblasts (HCFs) yielding the five most successful compounds Bufalin, Gitoxigenin, Lycorine, Anisomycin and Geldanamycin. Then, HCFs were contacted with an effective amount of a compound selected from the group consisting of Bufalin, Gitoxigenin, Lycorine, Anisomycin or Geldanamycin, wherein the amount of the test compound was from 0.05 µM to 20 µM for said compound. The effective amount of said compound is 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 16.0, 17.0, 18.0, 19.0 and 20.0. The effective amount for said compound is from 0.1 µM to 10 µM. Preferably, the effective amount is 0.1 µM, preferably 1 µM, more preferably 10 µM for Bufalin, Gitoxigenin, Anisomycin or Geldanamycin. For Lycorine, the preferred effective amount is 1 µM, preferably 5 µM, more preferably 10 µM. Said compounds with different concentrations were tested for their ability to decrease proliferation of HCFs. The most effective amount for each compound is 10 µM (see FIG. 1). Further, the compounds, in particular Bufalin and Lycorine were tested on renal fibroblasts and pulmonary fibroblasts. It was shown, that Lycorine significantly inhibits proliferation of renal fibroblasts, but also of pulmonary fibroblasts. Additionally, Bufalin significantly inhibits only proliferation of pulmonary fibroblasts. Here, the most effective amount for Lycorine and Bufalin is 10 µM (see FIG. 39).

Second, it was found that the compound selected from Bufalin, Gitoxigenin, Lycorine and Anisomycin does not exert its effect by inducing cell death confirmed by Annexin-7AAD-staining. Moreover, it was observed that expression levels of the extracellular matrix component Collagen1a1 were lower under treatment conditions by quantitative real time PCR and Western Blot. Standard techniques known to the person skilled in the art were used for quantitative real time PCR, PCR and Western Blot.

Additionally, no effect on proliferation of the cardiomyocyte cell line HL-1 could be detected, pointing towards a fibroblast-specific effect of said compounds (see FIG. 2-5).

In addition to the findings above, the invention also provides a method of preventing or treating fibrosis, preferably cardiac fibrosis, lung fibrosis and/or kidney fibrosis, more preferably cardiac fibrosis, using at least one compound selected from the group comprising Lycorine, Bufalin, Gitoxigenin, Anisomycin, and Geldanamycin, as well as salts, analogs and derivatives thereof.

For in vivo confirmation of the in vitro data, cardiac remodeling was induced in C57BL/6 mice via implantation of minipumps with Angiotensin II, a hormone that causes hypertension and cardiac remodeling, and said compounds were injected intraperitoneally every other day during two consecutive weeks (see FIG. 6). This technique for inducing cardiac remodeling is known to the person skilled in the art and can be performed in all non-human mammals.

After induction of cardiac remodeling in a non-human mammal, an effective amount of said test compound was applied every other day for a time period of two weeks to said non-human mammal, optionally for two consecutive weeks. The administration of said compound can also be performed for three weeks, four weeks, five weeks, six weeks, seven weeks or eight weeks, over 2 months, three months, four months, five months or six months. The effective amount is above 0.005 mg/kg, preferably from 0.005 mg/kg to 20 mg/kg. The effective amount for said compound is from 0.01 mg/kg to 10 mg/kg. The effective amount for Bufalin is from 0.1 mg/kg to 1 mg/kg, preferably 0.5 mg/kg. The effective amount for Gitoxigenin is from 0.005 mg/kg to 0.05 mg/kg, preferably 0.01 mg/kg. The effective amount for Lycorine is from 1 mg/kg to 10 mg/kg, preferably 4.5 mg/kg. The effective amount for Anisomycin is from 5 mg/kg to 15 mg/kg, preferably 10 mg/kg.

Those test compounds tested above also induce amelioration of heart function which was evidenced by echocardiographic assessment (see FIGS. 7 and 9). Moreover, collagen staining in histological sections of the hearts revealed a prominent reduction of fibrosis-development upon treatment with said compound (see FIGS. 8 and 10).

Further, the experiments described in Example 17 show that administration of said compounds in the murine model of Angiotensin II-induced HF did not provoke any changes in plasma marker of kidney and liver damage (see FIGS. 26 and 27), nor in the morphology of the two organs after application of said compound (see FIGS. 28 and 29). This provides first promising data of toxicological assessment of the inhibition of miRNA-671-5p for the treatment of fibrosis.

Additionally, in vivo therapeutic studies were performed with the preferred compounds Lycorine and Bufalin (see FIG. 11 and Example 5). Those compounds, particularly Lycorine are effectively taken up by the heart evidenced by higher levels in the myocardium in comparison to the plasma after injection of the compounds (see FIG. 30).

It was found that Bufalin and Lycorine tested as therapeutic agents prevent further development (progression) of cardiac fibrosis in diastolic heart failure in mice and upon treatment with those. Particularly, it was shown that Bufalin significantly improves both global and diastolic function of the heart (see FIG. 12). Further, Bufalin and Lycorine also recover left ventricular compliance of the murine heart upon angiotensin II-infusion by reducing passive stiffness of the left ventricle induced by systemic hypertension (see FIG. 13).

In particular, focus was drawn to Bufalin, which recovers velocity of tissue motion in diastole as well as recovers global longitudinal strain (GLS) in a murine model of angiotensin II-induced cardiac fibrotic disease (see FIGS. 14 and 15).

In conclusion, the compound selected from the group consisting of Bufalin, Gitoxigenin, Lycorine, Anisomycin or Geldanamycin as well as salts, analogs and derivatives thereof may be used as an anti-fibrotic compound, in a method of preventing or treating fibrosis in a subject, preferably cardiac fibrosis, lung fibrosis and/or kidney fibrosis, more preferably cardiac fibrosis.

The subject can be any subject as defined herein, preferably a human subject. The subject is preferably in need of the administration of said compounds.

Also contemplated by the present invention are derivatives of an inhibitor of miR-671-5p for use in a method of preventing or treating fibrosis, wherein the inhibitor is selected from the group of Lycorine, Bufalin, Gitoxigenin, Anisomycin and Geldanamycin.

Derivatives of Bufalin and Lycorine are preferred in the present invention. In particular, derivatives of Lycorine being selected from the group consisting of Amb24051775, Cephalotaxine, Dihydrolycorine, Pseudolycorine, Homoharringtonine, Lycobetaine, Amb24179473, N-methyl-Nartazine, alpha-Dihydrolycorine, N-methyl-lycorine and Galanthine are being preferred (see FIG. 37). Derivatives of Bufalin being selected from the group consisting of Arenobufagin 3-hemisuberate, Periplogenin, Periplogenin3-[O-beta-glucopyranosyl-(1-4)-beta-sarmentopyranoside], lanatoside C, Cinobufotalin, Arenobufagin, Cinobufagin, Periplocin, Scillaridin A, Bufogenin B, Bufarenogenin, Bufogenin, Gamabufotalin, Bufotalin, Deacetylcinobufagin are also being preferred (see FIG. 38). The derivatives of the present invention are capable of preventing the proliferation of HCF such as the proliferation is prevented by Bufalin and Lycorine themselves (see FIG. 31). Preferably, Homoharringtonine (No. 19 in FIG. 31), a lycorine derivative, prevents the proliferation of HCF best. Thus, not only the inhibitors of miR-671-5p of the present invention, but also the derivatives of said inhibitors are for use in a method for preventing or treating fibrosis, preferably cardiac fibrosis, lung fibrosis and/or kidney fibrosis, more preferably cardiac fibrosis.

Further, it was shown that not only cardiac fibrosis is prevented or treated by the inhibitors of the present invention, but also lung fibrosis and/or kidney fibrosis. Preferably, Lycorine and/or Bufalin inhibit proliferation of renal and pulmonary fibroblasts (see FIG. 39). Thus, the present invention demonstrates plausibly that an inhibitor of miR-671-5p being selected from the group consisting of Lycorine, Bufalin, Gitoxigenin, Anisomycin and Geldanamycin as well as salts, analogs and derivatives thereof is able to prevent or treat fibrosis.

TABLE 1

Overview of derivatives of Bufalin and Lycorine (see Example 20 and FIG. 31).

| Molecular name of derivatives | Group | Derivative No. in FIG. 31 |
|---|---|---|
| Amb24051775 | alkaloid | 1 |
| Cephalotaxine | alkaloid | 2 |
| Arenobufagin 3-hemisuberate | bufadienolide | 3 |
| Dihydrolycorine | alkaloid | 4 |
| Periplogenin | cardenolide | 5 |
| Periplogenin3-[O-beta-glucopyranosyl-(1-4)-beta-sarmentopyranoside] | cardenolide | 6 |
| lanatoside C | cardenolide | 7 |
| Cinobufotalin | bufadienolide | 8 |
| Arenobufagin | bufadienolide | 9 |
| Cinobufagin | bufadienolide | 10 |
| Periplocin | cardenolide | 11 |
| Scillaridin A | bufadienolide | 12 |
| Bufogenin B | bufadienolide | 13 |
| Bufarenogenin | bufadienolide | 14 |
| Pseudolycorine | alkaloid | 15 |
| Bufogenin | bufadienolide | 16 |
| Gamabufotalin | bufadienolide | 17 |
| Bufotalin | bufadienolide | 18 |
| Homoharringtonine | alkaloid | 19 |
| Lycobetaine | alkaloid | 20 |
| Amb24179473 | alkaloid | 21 |
| N-methyl-Nartazine | alkaloid | 22 |
| alpha-Dihydrolycorine | alkaloid | 23 |
| N-methyl-lycorine | alkaloid | 24 |
| Deacetylcinobufagin | bufadienolide | 25 |
| Galanthine | alkaloid | 26 |

During fibrosis different miRNAs are important as disease-specific biomarkers and are either up- or downregulated as fibrotic stages during the disease increases.

Therefore, a further aspect of the invention was the investigation of the mechanism underlying the anti-fibrotic potential of the identified compounds. Hereto, researchers performed a miRNA profiling approach via RNA deep sequencing in HCFs (see FIG. 16). Via qPCR it was found that miR-671-5p is downregulated by said test compounds, highlighting its potential importance in fibrosis-development (see FIG. 17).

In particular, the focus lies here on the human miRNA called miR-671-5p which is located on Chromosome 7, 151,232,499-151,238,827 on the forward strand. The mature miRNA sequence is as follows: 5' AGGAAGCCCUG-GAGGGGCUGGAG 3'.

As already mentioned, according to Murakami et al. (2012) miR-671-5p is known to play a role in liver fibrosis. In addition, according to Schulte et al. (2015) and Vegter et al. (2016), miR-671-5p plays a role in cardiovascular disease, mainly heart failure. However, the prevalence of elevated miR-671-5p levels in cardiac fibrosis was not reported in the prior art. In the experiments that led to the present invention, high-throughput miRNA sequencing was performed in human cardiac fibroblasts (HCFs), where almost 50 miRNAs were investigated to be considered as either pro- or anti-fibrotic miRNAs upon treatment with the anti-fibrotic compound Bufalin, a specific inhibitor of miR-671-5p (see FIG. 16). These miRNAs investigated in HCFs are as follows: hsa-miR-7974, hsa-miR-103a-3p, hsa-miR-4521, hsa-miR-23b-5p, hsa-miR-100-3p, hsa-miR-3648, hsa-miR-128-1-5p, hsa-miR-29b-1-5p, hsa-miR-605-3p, hsa-miR-370-5p, hsa-miR-152-5p, hsa-miR-25-5p, hsa-miR-671-3p, hsa-miR-1226-3p, hsa-miR-296-3p, hsa-miR-409-5p, hsa-miR-221-5p, hsa-miR-502-3p, hsa-miR-1301-3p, hsa-miR-125b-5p, hsa-miR-671-5p, hsa-miR-1271-5p, hsa-miR-100-5p, hsa-miR-181b-3p, hsa-miR-27b-5p, hsa-miR-330-3p, hsa-miR-92a-1-5p, hsa-miR-543, hsa-miR-188-5p, hsa-miR-128-3p, hsa-miR-1185-1-3p, hsa-miR-1343-3p, hsa-miR-26b-3p, hsa-miR-668-3p, hsa-miR-770-5p, hsa-miR-142-5p, hsa-miR-675-5p, hsa-miR-451a, hsa-miR-132-5p, hsa-miR-218-1-3p, hsa-miR-27a-5p, hsa-miR-215-5p, hsa-miR-132-3p, hsa-miR-33b-5p, hsa-miR-192-5p, hsa-miR-7977, hsa-miR-4443. Of the tested miRNAs, 33 miRNAs are considered as being potentially pro-fibrotic. Here, those miRNAs are downregulated in HCFs after treatment with Bufalin. These miRNAs illustrated in FIG. 16 are: hsa-miR-7974, hsa-miR-103a-3p, hsa-miR-4521, hsa-miR-23b-5p, hsa-miR-100-3p, hsa-miR-3648, hsa-miR-128-1-5p, hsa-miR-29b-1-5p, hsa-miR-605-3p, hsa-miR-370-5p, hsa-miR-152-5p, hsa-miR-25-5p, hsa-miR-671-3p, hsa-miR-1226-3p, hsa-miR-296-3p, hsa-miR-409-5p, hsa-miR-221-5p, hsa-miR-502-3p, hsa-miR-1301-3p, hsa-miR-125b-5p, hsa-miR-671-5p, hsa-miR-1271-5p, hsa-miR-100-5p, hsa-miR-181b-3p, hsa-miR-27b-5p, hsa-miR-330-3p, hsa-miR-92a-1-5p, hsa-miR-543, hsa-miR-188-5p, hsa-miR-128-3p, hsa-miR-1185-1-3p, hsa-miR-1343-3p, hsa-miR-26b-3p.

TABLE 2

47 mature miRNA sequences, whose miRNA expression of HCFs was observed using high-throughput miRNA sequencing (see Example 9).

| SEQ ID No. | mature hsa (homo sapiens) miRNAs | miRNA sequences |
|---|---|---|
| 1 | hsa-miR-671-5p | aggaagcccuggaggggcuggag |
| 2 | hsa-miR-7974 | aggcugugaugcucuccugagccc |
| 3 | hsa-miR-103a-3p | agcagcauuguacagggcuauga |
| 4 | hsa-miR-4521 | gcuaaggaaguccugugcucag |
| 5 | hsa-miR-4443 | uuggaggcguggguuuu |
| 6 | hsa-miR-23b-5p | uggguuccuggcaugcugauuu |
| 7 | hsa-miR-100-3p | caagcuuguaucuauagguaug |
| 8 | hsa-miR-7977 | uucccagccaacgcacca |
| 9 | hsa-miR-3648 | agccgcggggaucgccgaggg |
| 10 | hsa-miR-128-1-5p | cggggccguagcacugucugaga |
| 11 | hsa-miR-29b-1-5p | gcugguuucauauggugguuuaga |
| 12 | hsa-miR-192-5p | cugaccaugaauugacagcc |
| 13 | hsa-miR-605-3p | agaaggcacuaugagauuuaga |
| 14 | hsa-miR-370-5p | caggucacgucucugcaguuac |
| 15 | hsa-miR-152-5p | agguucugugauacacuccgacu |
| 16 | hsa-miR-25-5p | aggcggagacuugggcaauug |
| 17 | hsa-miR-671-3p | uccgguucucagggcuccacc |
| 18 | hsa-miR-1226-3p | ucaccagcccuguguucccuag |
| 19 | hsa-miR-296-3p | gagggugggguggaggcucucc |
| 20 | hsa-miR-409-5p | agguuacccgagcaacuuugcau |
| 21 | hsa-miR-221-5p | accuggcauacaauguagauuu |
| 22 | hsa-miR-33b-5p | gugcauugcuguugcauugc |
| 23 | hsa-miR-502-3p | aaugcaccugggcaaggauuca |
| 24 | hsa-miR-132-3p | uaacagucuacagccauggucg |
| 25 | hsa-miR-1301-3p | uugcagcugccugggagugacuuc |
| 26 | hsa-miR-125b-5p | ucccugagacccuaacuuguga |
| 27 | hsa-miR-27a-5p | augaccuaugaauugacagac |
| 28 | hsa-miR-215-5p | augaccuaugaauugacagac |
| 29 | hsa-miR-1271-5p | cuuggcaccuagcaagcacuca |
| 30 | hsa-miR-100-5p | aacccguagauccgaacuugug |
| 31 | hsa-miR-218-1-3p | augguuccgucaagcaccaugg |
| 32 | hsa-miR-181b-3p | cucacugaacaaugaaugcaa |
| 33 | hsa-miR-27b-5p | agagcuuagcugauuggugaac |
| 34 | hsa-miR-132-5p | accguggcuuucgauuguuacu |
| 35 | hsa-miR-330-3p | gcaaagcacacggccugcagaga |
| 36 | hsa-miR-675-5p | uggugcggagagggcccacagug |

TABLE 2-continued 47 mature miRNA sequences, whose miRNA expression of HCFs was observed using high-throughput miRNA sequencing (see Example 9).

| SEQ ID No. | mature hsa (homo sapiens) miRNAs | miRNA sequences |
|---|---|---|
| 37 | hsa-miR-451a | aaaccguuaccauuacugaguu |
| 38 | hsa-miR-92a-1-5p | agguugggaucgguugcaaugcu |
| 39 | hsa-miR-543 | aaacauucgcggugcacuucuu |
| 40 | hsa-miR-770-5p | uccaguaccacgugucagggcca |
| 41 | hsa-miR-142-5p | cauaaaguagaaagcacuacu |
| 42 | hsa-miR-188-5p | caucccuugcaugguggaggg |
| 43 | hsa-miR-128-3p | ucacagugaaccggucucuuu |
| 44 | hsa-miR-1185-1-3p | auauacaggggagacucuuau |
| 45 | hsa-miR-668-3p | ugucacucggcucggcccacuac |
| 46 | hsa-miR-1343-3p | cuccuggggcccgcacucucgc |
| 47 | hsa-miR-26b-3p | ccuguucuccauuacuuggcuc |

The present inventors also surprisingly found that miR-671-5p regulates fibrosis and inflammation in primary HCFs. This was found by testing that after overexpression of said miRNA, markers of fibrosis (α-Smooth Muscle Actin, α-SMA and Connective Tissue Growth Factor, CTGF) and inflammation (Interleukin-6, IL-6 and Interleukin-8, IL-8) were activated in HCFs (see FIG. 18). Further, overexpression of miR-671-5p also enhances migration of HCFs (see FIG. 19). These data reveal that miR-671-5p can be considered as being pro-fibrotic.

Moreover, it was shown that miR-671-5p is not only activated in various mouse models of heart failure, but also in human heart tissue of aortic stenosis-patients. This underscores the potential therapeutic relevance of regulation of this miRNA (see FIG. 20).

Further, the present invention contemplates identification of potential targets of miR-671-5p by using different web based bioinformatics target prediction tools. It was found, that miR-671-5p targets a circular RNA CDR1as, which is highly abundant in HCFs as well as Selenoprotein P as an additional target due to consequential pairing of target region to miR-671-5p (see FIGS. 21 and 20).

Assessment of levels of CDR1as as well as the mRNA encoded on the opposite strand on the same genomic locus were investigated in vitro. CDR1as levels were found to be increased in HCFs after treatment with the anti-fibrotic substances (see FIG. 22), whereas CDR1 mRNA levels decreased in HCFs after treatment with said compounds (see FIG. 23).

CDR1as can act as an antagonist of miRNAs and is encoded in the genome antisense to the human CDR1 (gene) locus (hence the name CDR1as). Selenoprotein is any protein that includes selenocysteine (Se-Cys) amino acid residues and is well established to be considered with an anti-fibrotic potential.

Additionally, it was discovered that the CDR1as is an anti-fibrotic target of miR-671-5p due to a silencing of CDR1as via sisiRNA-chemistry leading to an increase in expression levels of the extracellular matrix component Collagen1a1 in primary HCFs (see FIG. 24).

Therefore, the present invention further encompasses an activator of CDR1as for use in a method of preventing or treating fibrosis, preferably cardiac fibrosis, lung fibrosis and/or kidney fibrosis, more preferably cardiac fibrosis. In this context, the activator is selected from the group consisting of Lycorine, Bufalin, Gitoxigenin, Anisomycin and Geldanamycin, as well as salts, analogs and derivatives thereof. Preferably, the activator is Bufalin, more preferably the activator is Lycorine.

Again, the therapeutically effective amount of said test compound per administration is at least 0.1 µM, or more than 0.1 µM and less than 50 µM, or from 0.5 to 10 µM, or from 1 µM to 5 µM, preferably 1 µM for said compound. The amount of the test compound is at least 0.5 µM, 1 µM, 2 µM, 3 µM, 4 µM, 5 µM, 6 µM, 7 µM, 8 µM, 9 µM, or at least 10 µM. The amount of Bufalin, Anisomycin, Gitoxigenin and/or Geldanamycin is from 0.5 to 10 µM, or is from 0.5 µM to 5 µM, preferably 0.5 µM, 0.6 µM, 0.7 µM, 0.8 µM, 0.9 µM, 1 µM, 2 µM, 3 µM, 4 µM and/or 5 µM, more preferably 1 µM.

The amount of Lycorine is from 0.5 to 20 µM, or is from 0.5 µM to 10 µM, preferably 0.5 µM, 0.6 µM, 0.7 µM, 0.8 µM, 0.9 µM, 1 µM, 2 µM, 3 µM, 4 µM, 5 µM, 6 µM, 7 µM, 8 µM, 9 µM and/or 10 µM, more preferably 5 µM.

This particular finding can be considered as another unitary feature of the natural compound selected from the group consisting of Bufalin, Gitoxigenin, Lycorine, Anisomycin and Geldanamycin.

To sum it up, miR-671-5p regulates fibrosis and inflammation via its direct anti-fibrotic targets, the circular RNA CDR1as and Selenoprotein P.

Thus, the present invention provides an inhibitor of miR-671-5p for use in a method of preventing or treating fibrosis.

This particular finding, the inhibition of miR-671-5p, was observed for all of the natural compounds selected from the group consisting of Bufalin, Gitoxigenin, Lycorine, Anisomycin and Geldanamycin.

The present invention also envisages an inhibitor of miR-671-5p for use in a method of preventing or treating fibrosis, wherein said use comprises administering the inhibitor every other day for a time period of two weeks, three weeks, four weeks, five weeks, six weeks, seven weeks, eight weeks or about two months, three months, four months, five months, six months or even longer than half a year and/or a year. Preferably, said inhibitor is administered during two weeks, preferably for two consecutive weeks.

The administration of said inhibitor is performed by injections or by infusions, preferably by injections. The administration of the inhibitor is performed intraperitoneally, intravenously, subcutaneously, intramuscularly or orally, preferably intraperitoneally.

Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. The inhibitor is preferably injected. This injection is administered intraperitoneally.

The present invention also provides a kit that can be used including the inhibitor. The kit comprises the inhibitor of miR-671-5p and contains sufficient amounts of said inhibitor of miR-671-5p for effectively preventing or treating fibrosis.

In one embodiment, the kit comprises one or more containers filled with the pharmaceutical composition of the invention. Furthermore, one or more additional prophylactic or therapeutic agents useful for the treatment of a fibrosis, preferably cardiac fibrosis, lung fibrosis and/or kidney fibrosis, more preferably cardiac fibrosis can also be included in the pharmaceutical pack or kit.

The present invention further encompasses an in vitro method for identifying a compound for preventing or treating fibrosis. High-throughput miRNA sequencing was performed prior and after the treatment of anti-fibrotic compounds. miR-671-5p was used as a general target (see FIG. 17).

First, the in vitro method includes measuring the amount of miR-671-5p in cells undergoing fibrosis; and second, contacting the cells undergoing fibrosis with a test compound and third, comparing the amount of miR-671-5p in said fibrotic cells after step two with the amount of miR-671-5p measured in the first step, wherein a decrease in miR-671-5p levels indicates that the test compound is a compound for preventing or treating fibrosis.

The experiment described in Example 10 shows that the expression levels of miR-671-5p are decreased in primary HCFs upon treatment with Lycorine, Bufalin, Gitoxigenin, Anisomycin and Geldanamycin as compared to the DMSO-control.

In this context, the amount of the test compound per administration is at least 0.1 µM. The amount of the test compound per administration is 0.1 µM, 0.2 µM, 0.3 µM, 0.4 µM, 0.5 µM, 0.6 µM, 0.7 µM, 0.8 µM, 0.9 µM and/or 1 µM. The amount of the test compound per administration is at least 0.5 µM, 1 µM, 2 µM, 3 µM, 4 µM, 5 µM, 6 µM, 7 µM, 8 µM, 9 µM, or at least 10 µM. The amount of said test compound per administration is less than 50 µM. The amount of said test compound per administration is 50 µM, 45 µM, 40 µM, 35 µM, 30 µM, 25 µM, 20 µM, 15 µM, 10 µM. The amount of said test compound per administration is more than 0.1 µM or less than 50 µM, or from 0.5 to 10 µM, or from 1 µM to 5 µM, preferably 1 µM for said compound. In particular, the therapeutically effective amount of Bufalin, Anisomycin, Gitoxigenin and/or Geldanamycin is from 0.5 to 10 µM, or is from 0.5 µM to 5 µM, preferably 0.5 µM, 0.6 µM, 0.7 µM, 0.8 µM, 0.9 µM, 1 µM, 2 µM, 3 µM, 4 µM and/or 5 µM, more preferably 1 µM. The therapeutically effective amount of Lycorine is from 0.5 to 20 µM, or is from 0.5 µM to 10 µM, preferably 0.5 µM, 0.6 µM, 0.7 µM, 0.8 µM, 0.9 µM, 1 µM, 2 µM, 3 µM, 4 µM, 5 µM, 6 µM, 7 µM, 8 µM, 9 µM and/or 10 µM, more preferably 5 µM.

In one aspect, the cells undergoing fibrosis used for the in vitro methods described above can be cardiac cells, lung cells, liver cells, kidney cells, intestinal cells, skeletal muscle cells or dermal cells, preferably human cardiac fibroblasts (HCFs), renal fibroblasts, and/or primary pulmonary fibroblasts (HPFs), more preferably human cardiac fibroblasts (HCFs).

In conclusion, the present invention provides an inhibitor of miR-671-5p for use in a method of preventing or treating fibrosis, wherein the inhibitor is selected from the group consisting of Lycorine, Bufalin, Gitoxigenin, Anisomycin and Geldanamycin, as well as salts, analogs and derivatives thereof. Preferably, the inhibitor is Bufalin, more preferably the inhibitor is Lycorine. In a preferred embodiment, Bufalin and Lycorine are the preferred inhibitors of the present invention.

Further provided by the present invention is a use of an inhibitor of miR-671-5p for the manufacture of a medicament for therapeutic application of fibrosis. Preferably, the inhibitor is selected from the group consisting of Lycorine, Bufalin, Gitoxigenin, Anisomycin, Geldanamycin as well as salts, analogs and derivatives thereof.

Additionally, a method of preventing or treating fibrosis comprising administering an effective amount of an inhibitor of miR-671-5p to a subject in need thereof is also contemplated by the present invention. Preferably, the inhibitor is selected from the group consisting of Lycorine, Bufalin, Gitoxigenin, Anisomycin, Geldanamycin as well as salts, analogs and derivatives thereof. The subject can be any subject as defined herein. The subject is preferably in need of the administration.

Definitions

The term "fibrosis" refers to the formation of excess fibrous connective tissue in an organ or tissue in a reparative or reactive process, which can destroy the architecture and function of the underlying organ or tissue. As used herein, "fibrosis" in this context "fibrosis" can be selected from cardiac fibrosis, lung fibrosis, liver fibrosis, kidney fibrosis, gastrointestinal fibrosis, skeletal muscle fibrosis, systemic sclerosis, multifocal fibrosclerosis, sclerodermatous graft-versus-host disease (GVHD) in bone marrow transplantation recipients, nephrogenic systemic fibrosis or dermal fibrosis, preferably fibrosis is cardiac fibrosis, lung fibrosis and/or kidney fibrosis, more preferably cardiac fibrosis (in particular myocardial fibrosis).

The term "inhibitor" as used herein refers to a compound that inhibits a molecule, either directly by binding to it or indirectly.

A "molecule" refers to any amino acid, a protein, any nucleic acid, DNA and/or RNA. A RNA can be, in particular, mRNA, rRNA, tRNA, siRNA, sisiRNA and/or miRNA, preferably miRNA.

The term "directly by binding to" would include binding of the compound (e.g. inhibitor) to the promoter of said molecule. In this context, the inhibitor preferably does not bind directly to said molecule (e.g. miRNA). The inhibitor indirectly inhibits the miRNA, preferably its target miR-671-5p, thus having an indirect inhibitor of miR-671-5p for use in a method of preventing or treating fibrosis, preferably cardiac fibrosis, lung fibrosis and/or kidney fibrosis, more preferably cardiac fibrosis.

As used herein, the term "treating" and analogs terms refer to a management and care of a patient and/or the combating of disease or disorder.

As used herein, the terms "prevent", "preventing" and "prevention" refer to the prevention of the recurrence or the onset of one or more symptoms of a disorder or disease, especially in individuals which have been analyzed to be susceptible or likely to develop the disease. Such analysis can for example take into account certain marker substances in body fluids of individuals or a known or suspected hereditary disposition or risk for developing such diseases.

The term "compound" or "test compound" refers to a natural compound, a synthetic compound or a hemisynthetic compound, preferably the compound is selected from the group consisting of Lycorine, Bufalin, Gitoxigenin, Anisomycin and Geldanamycin, salts, analogs and derivatives thereof as well as the stereoisomers of said analogs. In this context, the compound acting as an inhibitor refers to a natural compound.

The term "cardiac glycoside" used herein refers to the category of compounds that have a positive inotropic effect on the heart. As a general class of compounds, cardiac glycosides comprise a steroid core with either a pyrone or butenolide substituent at C17 (the "pyrone form" and "butenolide form"). Additionally, cardiac glycosides may optionally be glycosylated at C3. The form of cardiac glycosides without glycosylation is also known as "aglycone." Most cardiac glycosides include one to four sugars attached to the 3β-OH group. The sugars most commonly used include L-rhamnose, D-glucose, D-digitoxose, D-digitalose, D-digginose, D-sarmentose, L-vallarose, and D-fructose. In general, the sugars affect the pharmacokinetics of a cardiac glycoside with little other effect on biological activity.

A large number of cardiac glycosides are known in the art. Exemplary cardiac glycoside include, but are not limited to, bufalin, ouabain, digitoxigenin, digoxin, lanatoside C, Strophantin K, uzarigenin, desacetyllanatoside A, digitoxin, actyl digitoxin, desacetyllanatoside C, strophanthoside, scillarenin, scillaren A, proscillaridin, proscillaridin A, BNC-1, BNC-4, digitoxose, gitoxin, strophanthidiol, oleandrin, acovenoside A, strophanthidine digilanobioside, strophanthidin-d-cymaroside, digitoxigenin-L-rhamnoside, digitoxigenin theretoside, strophanthidin, strophanthidine, strophanthidine digilanobioside, strophanthidin-Dcymaroside, digoxigenin, digoxigenin 3,12-diacetate, gitoxigenin, gitoxigenin 3-acetate, gitoxigenin 3,16-diacetate, 16-acetyl gitoxigenin, acetyl strophanthidin, ouabagenin, 3-epigoxigenin, neriifolin, acetylneriifolin cerberin, theventin, somalin, odoroside, honghelin, desacetyl digilanide, calotropin, calotoxin, lanatoside A, uzarin, strophanthidine-3β-digitoxoside, strophanthidin a-L-rhamnopyranoside, as well as analogs, derivatives, pharmaceutically acceptable salts, and/or prodrugs thereof.

The term "alkaloid" as used herein refers to a group of naturally occurring chemical compounds that mostly contain basic nitrogen atoms. Alkaloids are produced by a large variety of organisms including bacteria, fungi, plants, and animals. They can be purified from crude extracts of these organisms by acid-base extraction. Alkaloids have a wide range of pharmacological activities including antimalarial, antiasthma, anticancer, cholinomimetic, vasodilatory, antiarrhythmic, analgesic, antibacterial and antihyperglycemic activities.

The term "antibiotic" as used herein describes a type of antimicrobial drug used in the treatment and prevention of bacterial infections, by either killing or inhibiting the growth of bacteria. Antibiotics have normally no positive influence on viruses such as the influenza virus. The classification of antibiotics is commonly based on their mechanism of action, chemical structure, or spectrum of activity, mostly targeting bacterial function. Either antibiotics target the cell wall (penicillins) or the cell membrane (polymyxins) or interfere with essential bacterial enzymes. These antibiotics have bactericidal activities. Those that target protein synthesis (anisomycin and tetracyclines) are usually bacteriostatic. Another criteria for a further characterization includes the target specificity. Such antibiotics target either a limited spectrum of specific bacteria or a broad spectrum of a wide range of bacteria.

The term "non-human mammal" as used herein refers to the group consisting of rodents, dogs, felids, primates, rabbits, pigs and ruminants, preferably a pig, more preferably a mouse.

The term "subject" refers to a mammal in particular a human, non-human primate, a rodent, a dog, a felid, a rabbit, a pig and a ruminant. Preferably the subject is a human subject.

The term "analog" or "structural analog" refers to a compound having a structure similar to that of another compound, but differing from it in respect to a certain component, differing in one or more atoms, functional groups, or substructures, which are replaced with other atoms, groups, or substructures.

The term "derivative" refers to a compound that is derived from a similar compound by a chemical reaction. In this context, derivatives of an inhibitor of miR-671-5p, wherein the inhibitor is selected from the group consisting of Lycorine, Bufalin, Gitoxigenin, Anisomycin and Geldanamycin have a similar structure to the inhibitors of the present invention per se and are also capable of preventing or treating fibrosis.

It is noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "less than" or in turn "greater than" includes the concrete number. For example, less than 20 means less than or equal to. Similarly, more than or greater than means more than or equal to, or greater than or equal to, respectively.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having". When used herein "consisting of" excludes any element, step, or ingredient not specified.

The term "including" means "including but not limited to". "Including" and "including but not limited to" are used interchangeably.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications cited throughout the text of this specification (including all patents, patent application, scientific publications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

The content of all documents and patent documents cited herein is incorporated by reference in their entirety.

A better understanding of the present invention and of its advantages will be had from the following examples, offered for illustrative purposes only. The examples are not intended to limit the scope of the present invention in any way.

EXAMPLES

Hereinafter, the present invention is described in more detail and specifically with reference to the Examples, which however are not intended to limit the present invention.

Example 1: Identification of Anti-Fibrotic Natural Compounds Bufalin, Gitoxigenin, Lycorine, Anisomycin and Geldanamycin In Vitro Functional screen of 480 nature-derived substances in vitro in primary human cardiac fibroblasts (HCFs) uncovers compounds inhibiting proliferation of HCFs.

Figure 1:
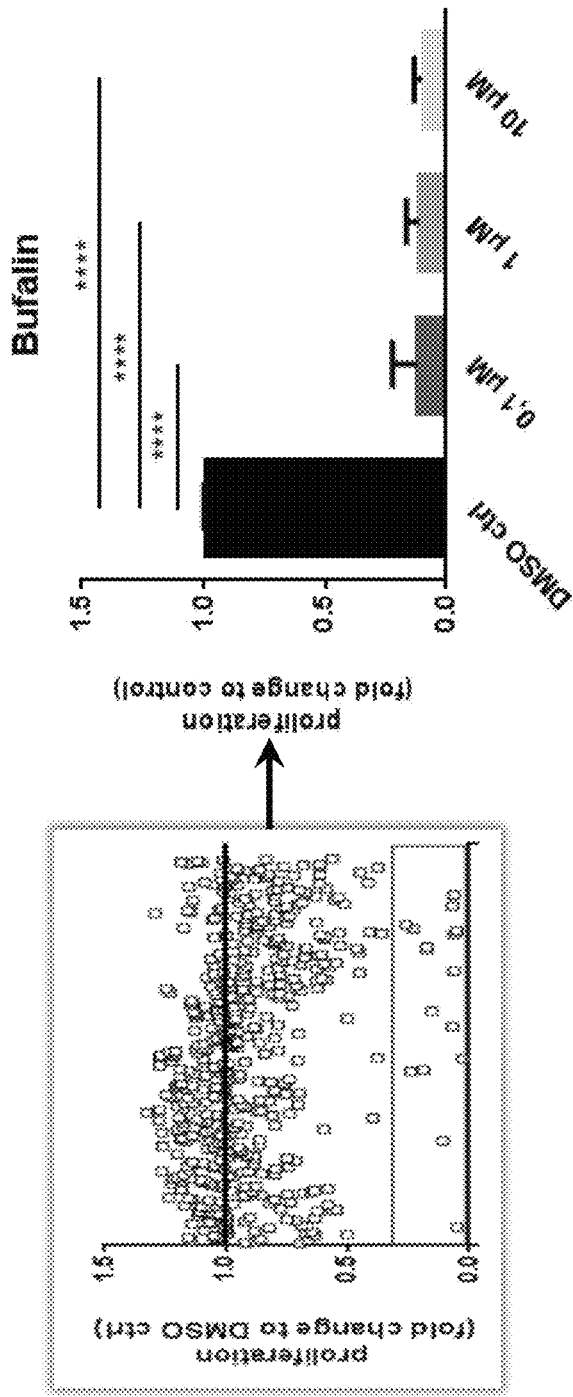
FIG. 1: Identification of anti-fibrotic natural compounds Bufalin, Gitoxigenin, Lycorine, Anisomycin and Geldanamycin in vitro.
Figure 1:
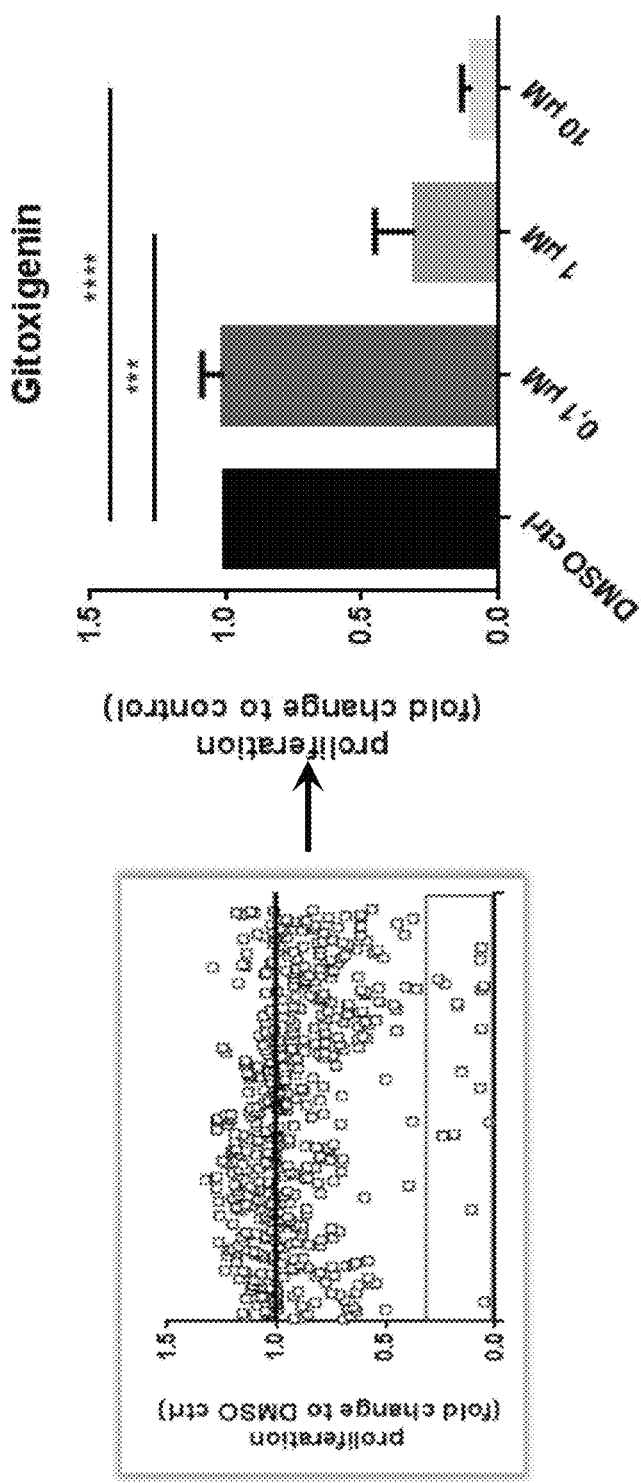
Figure 1:
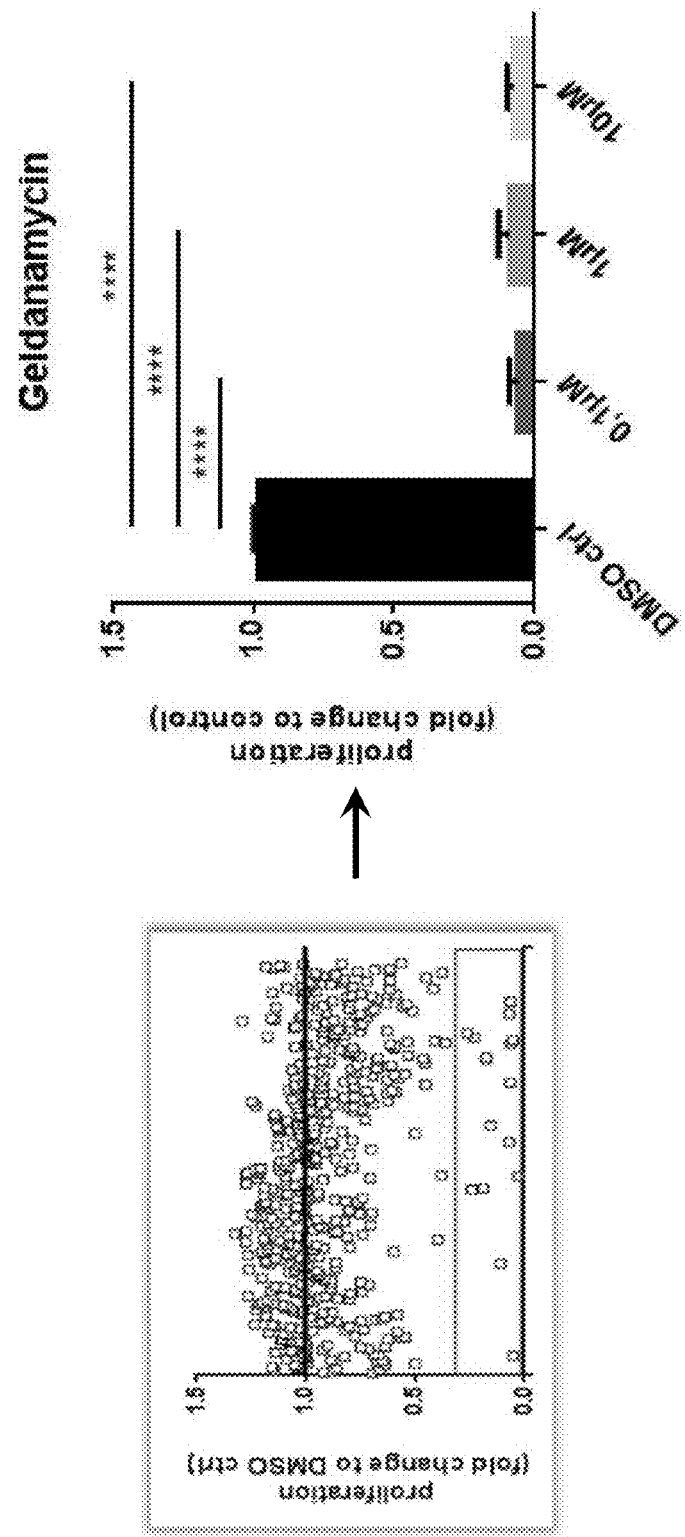
Figure 1:
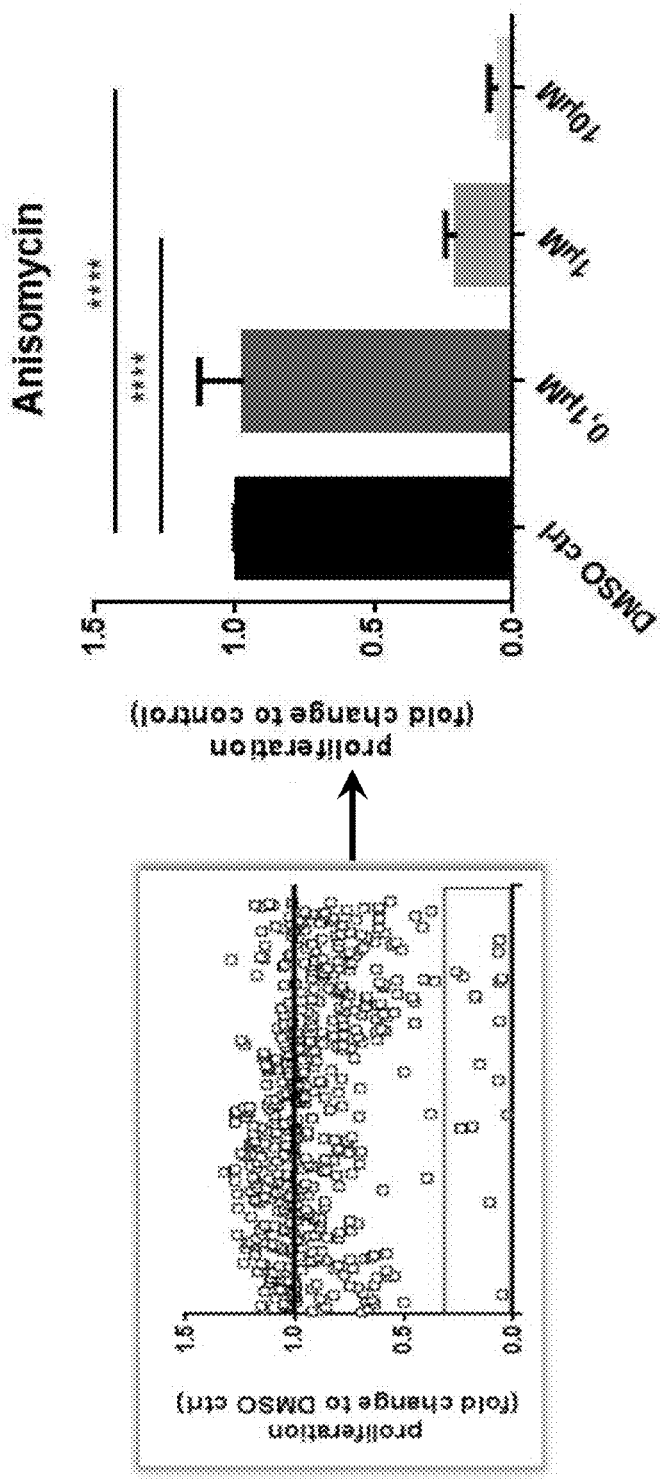
Figure 1:
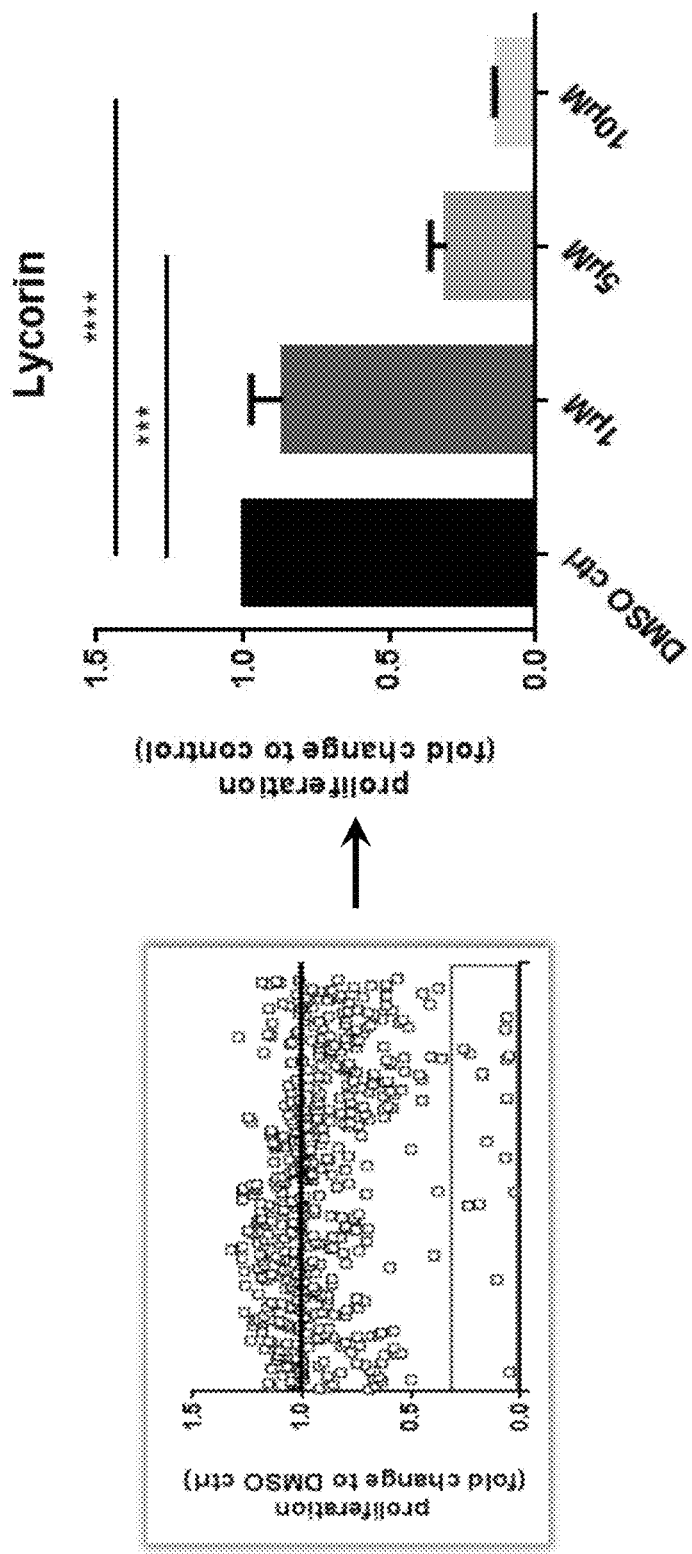

HCFs were incubated with 0.1 µM, 1 µM and 10 µM Bufalin, Gitoxigenin, Anisomycin and Geldanamycin as well as with 1 µM, 5 µM and 10 µM Lycorine for 24 h and proliferation of HCFs was measured by BrdU-ELISA (see FIG. 1). Due to major drawbacks as a drug candidate, Geldanamycin was not included in the follow-up studies, in particular in the in vivo experiments.

Example 2: Anti-Fibrotic Compounds Potently and Specifically Act on HCFs In Vitro Dose-dependent inhibitory effects of Bufalin, Gitoxigenin, Lycorine and Anisomycin on proliferation of primary HCFs are fibroblast-specific as evidenced by no impact of the same concentrations of said compounds on proliferation of HL-1.

HCFs and HL-1 cells were treated with Bufalin, Gitoxigenin, Lycorine and Anisomycin for 24 h with the same concentrations as indicated in Example 1 and proliferation of HCFs and cardiomyocyte cell line HL-1 cells was measured by BrdU-ELISA, DMSO refers as a control (see FIG. 2B, 3B, 4B, 5B). The cell proliferation ELISA is a colorimetric alternative to quantitate cell proliferation based on the measurement of BrdU incorporation during DNA synthesis in proliferating cells. After its incorporation into DNA, BrdU is detected by immunoassay by using antibodies being highly specific for BrdU. First, HCFs and/or HL-1 cells are cultured together with various dilutions of test substances (e.g. mitogens, growth factors, cytokines and test compounds such as Bufalin, Gitoxigenin, Lycorine and Anisomycin as mentioned above etc.) in a 96-well in a final volume of 100 µl/well in a humified atmosphere of 37° C. Afterwards, 10 µl/well BrdU labeling solution is added to the cells being cultured in 100 µl/well (final concentration: 10 µM BrdU). Then, cells were re-incubated for additional 2 to 24 h at 37° C. Next, labeling solution is removed and 200 µl/well FixDenat is added to the cells and incubated for 30 min at 15 to 25° C. Then, 100 µl/well anti-BrdU-POD working solution is added and incubated for approximately 90 min, after FixDenat is removed. Next, antibody conjugate is removed and wells are washed with 200 µl-300 µl/well Washing solution (PBS, 1×). After the washing solution is removed, 100 µl/well Substrate solution is added and it is incubated again until color development is sufficient for photometric detection. Further, HCFs were treated with said compounds (Lycorine: 5 µM, Bufalin: 1 µM, Gitoxigenin: 1 µM and Anisomycin: 1 µM) for 24 h as indicated again and subjected to FACS analysis after Annexin-7AAD-staining (see FIG. 2C, 3C, 4C, 5C). After the treatment with said compounds, annexin-7AAD-staining starts with inducing apoptosis in HCFs by a desired method, known to the person skilled in the art, a negative control (w/o induction and staining) and a positive control (f. ex. 500 µM $H_2O_2$ or 3 µM Staurosporin) is also needed. Then, the medium with HCFs is transferred into a falcon, washed with PBS and trypsinized. Everything is centrifuged for 5 min at 300×g and then the supernatant is aspirated. The pellet is re-suspended in 200 µl Annexin Red/7AAD Working Solution (1:20, 5 µl Annexin Red/7AAD+195 µl 1× Assay Buffer) and transferred into an Easy Cap Eppendorf tube. After incubation of 15 min at 37° C., it is centrifuged at room temperature (RT) for 5 min at 300×g. Then, the supernatant is aspirated, the pellet washed once with 200 µl 1× Assay Buffer and centrifuged again at RT for 5 min at 300×g. Again, the supernatant is aspirated and the pellet is re-suspended in 200 µl Annexin Red/7AAD working solution and incubated again at RT for 5 min in the dark. Samples are now ready for acquisition on a flow cytometer (blue and red laser).

Additionally, HCFs were treated with said compounds (Lycorine: 5 µM, Bufalin: 1 µM, Gitoxigenin: 1 µM and Anisomycin: 1 µM) for 24 h as indicated again, lysed and analyzed for extracellular matrix component Collagen1a1 protein levels in primary HCFs (normalized to GAPDH) by representative Western Blot, DMSO refers as a control (see FIG. 2D, 3D, 4D, 5D).

Example 3: Murine Model of Angiotensin II-Induced Cardiac Fibrotic Disease

Diastolic heart failure (HF) was induced in C57BL/6 mice via implantation of angiotensin II filled minipumps. Male C57BL/6 mice 8-10 weeks old were used in the present invention being based on a C57BL/6N-background (Charles River, Germany).

For implantation of angiotension II filled minipumps, Angiotensin-II is applied by osmotic minipumps for two weeks (Alzet® [Modell 1001]). The recommended dose amounts for 1.5 or 3.0 mg/kg/per day. The minipumps are filled under sterile conditions with Angiotensin-II or with isotonic saline solution functioning as a control substance. Implantation takes place under intraperitoneal injection anaesthesia. After injection of the anaesthetic, a certain time should be waited until the interdigital reflex does not exist anymore. Mice are then fixed on a pre-heated operating table and are provided with Bepanthen eye salve against drying out of the conjunctives. The operating field is located in the right caudal third of the back. It is shaved and desinfected with Braunol, afterwards it is coated with a 0.5% Lidocain-solution. After a period of one hour implantation can be started. The skin is cut through vertical to the back line, preferably the length is one centimeter. A pocket from the cutting line to cranial is subcutaneously formed. Herein, the minipumps are injected. Afterwards, the skin is then closed with a 5-0 Prolene string with interrupted sutures. Then, the closed wound is coated again with Braunol. For preventing hypothermia mice wake up in their cages, which are placed up to one-third on a terrarium-warming mat with regulated temperatures of 37°. Surgery amounts for 5 minutes/per animal.

Next, the natural compounds (Bufalin, Gitoxigenin, Lycorine, and Anisomycin) were injected intraperitoneally every other day during two consecutive weeks starting two days after the operation (see FIG. 6). DMSO was also injected into C57BL/6 mice with induced cardiac remodeling as a control. Cardiac function was assessed echocardiographically and fibrosis-development via collagen staining with picosirius-red in histological sections of the hearts (Example 4).

Example 4: Bufalin, Lycorine, Anisomycin and Gitoxigenin Significantly Ameliorate Cardiac Function and Cardiac Fibrosis in a Murine Model of Induced Cardiac Fibrotic Disease Natural compounds ameliorate heart function in a murine model of angiotensin II-induced cardiac fibrotic disease in vivo.

Diastolic HF was induced in C57BL/6 mice and the natural compounds were injected as indicated in Example 3. Fourteen days after the operation, cardiac function of the mice was assessed echocardiographically (n=9-15 per group) by treating the mice with said compounds (Bufalin: 0.5 mg/kg, Lycorine 4.5 mg/kg, Anisomycin: 10 mg/kg and Gitoxigenin: 0.01 mg/kg). A decrease of the Myocardial Performance Index (MPI) as well as a reduction of the isovolumetric relaxation time (IVRT) and an increase in E to A peak ratio (E/A) (the ratio of the early (E) to late (A) ventricular filling velocities as a marker of the function of the left ventricle of the heart) indicate improvement of both global (MPI) and diastolic (IVRT and E/A) function of the heart (see FIGS. 7 and 9).

Further, fourteen days after the operation, histological sections of the hearts were stained for collagen using picosirius-red (n=3-5 per group) after treatment with said compounds (Bufalin: 0.5 mg/kg, Lycorine 4.5 mg/kg, Anisomycin: 10 mg/kg and Gitoxigenin: 0.01 mg/kg). Prominent reduction of collagen deposition in representative images of histological sections of the hearts as well as the quantification of picrosirius-stained areas point to prevention of fibrosis-development by Bufalin, Lycorine, Anisomycin and Gitoxigenin (see FIGS. 8 and 10).

Example 5: Murine Model of Angiotensin II-Induced Cardiac Fibrotic Disease II Diastolic heart failure (HF) was induced in C57BL/6N mice via implantation of angiotensin II filled minipumps (see Example 3). In difference to Example 3, C57BL/6N mice were infused with 3 mg/kg/day angiotensin II by subcutaneously implanted minipumps for eight weeks.

Next, Bufalin or Lycorine (dissolved in DMSO) or the solvent DMSO alone (as control) were injected intraperitoneally (i.p) every other day until the endpoint, starting two weeks after start of angiotensin II-infusion (see FIG. 11).

Example 6: Bufalin and Lycorine Significantly Ameliorate Cardiac Function and Cardiac Fibrosis in a Murine Model of Induced Cardiac Fibrotic Disease Diastolic HF was induced in C57BL/6 mice and Bufalin or Lycorine were injected as indicated in Example 5. Eight weeks after the operation, cardiac function of the mice was assessed echocardiographically (n=5-12 per group) by treating the mice with said compounds (Bufalin: 0.5 mg/kg, Lycorine 4.5 mg/kg).

A decrease of the Myocardial Performance Index (MPI) (see FIG. 12B) as well as a reduction of the isovolumetric relaxation time (IVRT) (see FIG. 12C) and an increase in E to A peak ratio (E/A) (the ratio of the early (E) to late (A) ventricular filling velocities as a marker of the function of the left ventricle of the heart) (see FIG. 12D) indicate improvement of both global (MPI) and diastolic (IVRT and E/A) function of the heart, in particular for Bufalin.

Additionally, eight weeks after the operation, histological sections of the hearts were stained for collagen using picrosirius-red (n=7-12 per group) after treatment with Bufalin or Lycorine. Prominent reduction of collagen deposition in representative images of histological sections of the hearts as well as the quantification of picrosirius-stained areas point to prevention of fibrosis-development by Bufalin or Lycorine (see FIG. 12A).

Example 7: Bufalin and Lycorine Recover Left Ventricular Compliance of the Murine Heart Upon Angiotensin II-Infusion Diastolic HF was induced in C57BL/6 mice and Bufalin or Lycorine were injected as indicated in Example 5. Eight weeks after the operation, hemodynamic measurements of the mice were assessed (n=6-7 per group) by treating the mice with said compounds (Bufalin: 0.5 mg/kg, Lycorine 4.5 mg/kg).

Hemodynamic (dynamics of the blood flow, here in the heart) measurements were performed using invasive clinical blood pressure measurement (called MILLAR, in particular 1F, PVR-1000, Millar Instruments), showing a significant reduction of the end-diastolic pressure-volume relationship (EDPVR) by Bufalin and Lycorine treatment (see FIG. 13).

Example 8: Improvement of Cardiac Function by Bufalin Treatment

Diastolic HF was induced in C57BL/6 mice and Bufalin were injected as indicated in Example 5. Eight weeks after the operation, cardiac function of the mice was assessed echocardiographically (n=3-6 per group) by treating the mice with said compounds (Bufalin: 0.5 mg/kg)

Echocardiographic measurements were performed using Tissue Doppler Imaging (TDI), which refers to a medical ultrasound technology mainly used in Echocardiography that measures the velocity of the heart muscle or myocardium through the phases of one or more heartbeats by the Doppler effect (frequency shift) of the reflected ultrasound (see FIG. 14).

Additionally, myocardial deformation was assessed using strain imaging such as 2-dimensional speckle-tracking strain echocardiography. Global longitudinal strain (GLS), a measure for the deformation of the myocardium, which decreases when diastolic dysfunction is present, is depicted in FIG. 15. In accordance with the murine model for heart failure with preserved ejection fraction (HFpEF) (a mouse model for diastolic dysfunction of the heart), the parameter of the systolic function of the heart, namely the ejection fraction (EF), how much blood is ejected during the contraction phase, remained comparable in all tested groups (also see FIG. 15).

Example 9: High-Throughput miRNA Sequencing in Human Cardiac Fibroblasts Treated with Anti-Fibrotic Compounds Bufalin impacts on the miRnome of HCFs in vitro and changes the miRNA-signature of HCFs.

HCFs were treated with 1 μM Bufalin for 24 h as indicated, total RNA was isolated and subjected to high-throughput miRNA sequencing profiling via deep sequencing, DMSO refers as a control. To perform a high-throughput miRNA sequencing the Illumine® TruSeq® Small RNA technology is used to prepare various RNA species which is known to the person skilled in the art. In view of said technology, advantages of the natural structure common to most known microRNA molecules are taken. Most mature miRNAs have a 5'-phosphate and a 3'-hydroxyl group as a result of the cellular pathway used to create them. Because of this, the Illumina adapters which are used are directly and specifically ligated to miRNAs. Thus, libraries for subsequent cluster generation are prepared, using total RNA as input. Further, adapter ligation, reverse transcription, PCR amplification, and pooled gel purification to generate a library product is applied as it is known to the skilled person in the art. The top-30 significantly deregulated miRNAs indicate potentially pro-fibrotic miRNAs that are downregulated after Bufalin treatment. Data represent pooled triplicates from 3 independent experiments. Representative experiment shown; the same experiment was performed with all the anti-fibrotic natural substances identified (see FIG. 16).

Example 10: miR-671-5p Levels are Significantly Decreased by Identified Anti-Fibrotic Compounds in HCFs Expression levels of miR-671-5p are decreased in primary HCFs upon treatment with Bufalin, Gitoxigenin, Lycorine, Anisomycin and Geldanamycin as compared to the DMSO-control.

HCFs were incubated for 24 h with Bufalin (1 µM), Gitoxigenin (1 µM,) Lycorine (5 µM), Anisomycin (1 µM) and Geldanamycin (1 µM) and downregulation of miR-671-5p (normalized to RNU48) by the respective compound was validated via qRT-PCR, DMSO refers as a control Representative experiment show that the same experiment was performed with all the anti-fibrotic natural substances identified (see FIG. 17).

Example 11: miR-671-5p Regulates Fibrosis and Inflammation and Overexpression of miR-671-5p Enhances Migration of HCFs In Vitro Both Under Basal Conditions and Under Treatment Conditions with Bufalin Overexpression of miR-671-5p leads to activation of markers of fibrosis and inflammation in primary HCFs. Conversely, inhibition of miR-671-5p leads to a prominent decrease in above mentioned markers of fibrosis and inflammation (normalized to 18S rRNA) in primary HCFs.

For that, HCFs were transfected with miR-671-5p mimic (see FIG. 18A) and inhibitor (mirVana® miRNA inhibitor against hsa-miR-671-5p, Thermo Fisher Scientific) respectively (see FIG. 18B), and 48 h later analyzed for mRNA-expression of α-SMA, CTGF as fibrosis markers and IL-6 and IL-8 as inflammation markers via qRT-PCR.

Additionally, overexpression of miR-671-5p stimulates migration of primary HCFs both with and without treatment with anti-fibrotic Bufalin.

For that, HCFs were transfected with miR-671-5p mimic and incubated for 24 h with 1 µM Bufalin. 48 h after transfection, migratory behavior was studied in a Boyden Chamber assay (see FIG. 19). The Boyden chamber is a useful tool to study cell migration and cell invasion. It consists of a cylindrical cell culture insert nested inside the well of a cell culture plate. The insert contains a polycarbonate membrane at the bottom with a defined pore size. Cells are seeded in the top of the insert in serum-free media, while serum or similar chemoattractants are placed in the well below. Migratory cells move through the pores toward the chemoattractant below and can be stained or quantified in a plate reader. Invasive cells may be similarly measured by the placement of a coating of extracellular matrix proteins on top of the membrane.

First, 48 h after transfection with miR-671-5p mimic and Bufalin, HCFs need to be DAPI stained. For that, medium is discarded and fresh medium is added (1 ml/6 well; DAPI 1 µl/ml Medium (1:1000)) with fluorescent dye (switch off the light). After incubation for 30 min to 1 h at 37° C. in the $CO_2$-incubator, the HTS Fluoro Blok inserts (8 µm size, BD Falcon #351152) are prepared and coated. After microscopic control of the fluorescence, the cells are washed with 1 ml PBS. Then, the cells are trypsinized and centrifugated for 5 min at 200×g, 4° C. Then, supernatant is discarded and the pellet is diluted in 250 µl Medium+1% BSA or 1% FCS. After that, the cells should be counted and diluted to $5 \times 10^4$-$1 \times 10^5$ in 200 µl Medium+1% BSA or 1% FCS. Next, 700 µl Medium+VEGF+SDF or Medium+10% FCS are aliquoted into each well of the 24-well companion plate and the (pretreated) inserts are hung into the medium. 200 µl cell suspension is pipetted in the middle of the insert and incubated 4 to 24 h (maximum), at 37° C. in the $CO_2$-Inkubator (maybe control migration after 2 h). At a maximum of 24 h after seeding, microscopy can be done and pictures of the migrated cells can be taken.

Example 12: miR-671-5p is Activated in Murine and Human Fibrotic Hearts

Expression of miR-671-5p is increased in various murine heart failure (HF) models (hypertension, pressure overload and allogenic heart transplantation).

Again, HF was induced in mice via implantation of angiotensin II filled minipumps (Example 3), Transverse Aortic Constriction (TAC) or allogenic transplantation of the hearts. The hearts were harvested at the indicated time points (n=3-7 per group).

Moreover, miR-671-5p is activated in human hearts of aortic stenosis-patients. Cardiac biopsies were taken from left ventricles of patients undergoing aortic valve replacement due to aortic stenosis or healthy adult donor hearts not used for transplantation (n=6 per group). Increased levels of miR-671-5p (normalized to snoRNA-202 in murine and to RNU48 human heart tissue) were studied via qRT-PCR (see FIG. 20).

Example 13: The Circular RNA CDR1as is a Direct Target of miR-671-5p

Predicted consequential pairing of CDR1as and miR-671-5p in humans was done via www.targetscan.org/vert_71/. Divergent primers were used to specifically amplify the circular RNA, which is highly abundant in HCFs as represented by low CT-values (see FIG. 21A).

Circularity of CDR1as was evidenced by resistance to exonuclease treatment that was 10-times fold higher than the resistance of the linear transcript of GAPDH (see FIG. 21B).

Validation of miR-671-5p targeting CDR1as was done by qRT-PCR (normalized to 18S rRNA) after overexpression of miR-671-5p in primary HCFs. For that, HCFs were transfected with miR-671-5p mimic and 48 h later analyzed for CDR1as-expression (normalized to 18S rRNA) via qRT-PCR (see FIG. 21C).

Example 14: The Circular RNA CDR1as is Increased after Treatment with Identified Antifibrotic Compounds in HCFs and Acts Therefore as an Anti-Fibrotic Circular RNA Expression levels of CDR1as are increased in primary HCFs upon treatment with Bufalin, Gitoxigenin, Lycorine, Anisomycin and Geldanamycin. HCFs were incubated for 24 h with Bufalin (1 µM), Gitoxigenin (1 µM,) Lycorine (5 µM), Anisomycin (1 µM) and Geldanamycin (1 µM) and upregulation of CDR1as (normalized to 18S rRNA) by the respective compound was validated via qRT-PCR (see FIG. 22).

Further, strand-specific silencing of CDR1as via sisiRNA-chemistry leads to an increase in expression levels of the extracellular matrix component Collagen1a1 in primary HCFs as shown in a representative Western Blot. sisiRNAs are small internally segmented interfering RNAs that allow strand-specific silencing of CDR1as, which is located perfectly antisense to the CDR1 coding gene. 48 h after transfection HCFs were lysed and analyzed for Collagen1a1 protein levels (normalized to GAPDH) (see FIG. 24).

Example 15: The CDR1 mRNA Encoded on the Opposite Strand of CDR1as Changes Discordantly to miR-671-5p after Treatment with Identified Anti-Fibrotic Compounds in HCFs Expression levels of CDR1 mRNA change independently of miR-671-5p or CDR1as in primary HCFs upon treatment with Bufalin, Gitoxigenin, Lycorine, Anisomycin and Geldanamycin. HCFs were incubated for 24 h with Bufalin (1 µM), Gitoxigenin (1 µM,) Lycorine (5 µM), Anisomycin (1 µM) and Geldanamycin (1 µM) and impact on CDR1 mRNA level (normalized to GAPDH) by the respective compound was validated via qRT-PCR (see FIG. 23).

Example 16: Selenoprotein P is Another Direct Target of miR-671-5p

Predicted consequential pairing of Selenoprotein P target region and miR-671-5p in humans was done via www.targetscan.org/vert_71/(see FIG. 25A). Validation of miR-671-5p targeting Selenoprotein P was assayed by luciferase activity and qRT-PCR after overexpression of miR-671-5p. A HEK293 cell line and primary HCFs were transfected with miR-671-5p mimic and 24 h later analyzed for luciferase activity, or 48 h later for Selenoprotein P-expression (normalized to 18S rRNA) via qRT-PCR, respectively (see FIG. 25B).

Example 17: Administration of Bufalin, Gitoxigenin, Lycorine and Anisomycin does not Provoke any Changes in Plasma Marker of Kidney and Liver Damage and Additionally Bufalin and Lycorine does not Provoke any Changes in Kidney and Liver Morphology In Vivo Toxicological assessment of Bufalin, Gitoxigenin, Lycorine and Anisomycin in a murine model of Angiotensin II-induced HF shows no elevation of plasma markers of kidney (creatinine and urea) and liver (Glutamate oxaloacetate transaminase (GOT) and Glutamate pyruvate transaminase (GPT)).

HF was induced in mice (Example 3) and Bufalin (0.5 mg/kg), Gitoxigenin (0.01 mg/kg), Lycorine (4.5 mg/kg), and Anisomycin (10 mg/kg) were injected as indicated in Example 3. Fourteen days after the operation, EDTA-plasma samples were drawn (n=2-3 per group) (see FIGS. 26 and 27).

Additionally, toxicological assessment of Bufalin and Lycorine in a murine model of Angiotensin II-induced HF does not induce necrosis, inflammation or any morphological changes in kidney and liver, respectively.

Again, HF was induced in mice (Example 3) and Bufalin (0.5 mg/kg) as well as Lycorine (4.5 mg/kg) were injected as indicated in Example 3. Fourteen days after the operation, kidneys and livers were subjected to histological assessment via Hematoxylin and Eosin (HE) and Periodic acid-Schiff (PAS) stain (n=2-4 per group) (see FIGS. 28A and B).

Example 18: Bufalin and Lycorine does not Provoke any Changes in Kidney and Liver Morphology In Vivo (Therapeutic Approach)

HF was induced in mice (Example 5) and Bufalin (0.5 mg/kg) as well as Lycorine (4.5 mg/kg) were injected as indicated in Example 5. Eight weeks after the operation, kidneys and livers were subjected to histological assessment via Hematoxylin and Eosin (HE) and Periodic acid-Schiff (PAS) stain (n=4 per group).

The data show that administration of Bufalin and Lycorine does not provoke any changes in kidney and liver morphology in vivo in mice (see FIG. 29).

Example 19: Evaluation of Myocardial and Plasma Concentrations of Bufalin and Lycorine In Vivo Plasma and hearts of C57BL/6N mice were harvested 9 minutes after injection with natural substances Bufalin (0.5 mg/kg) or Lycorine (4.5 mg/kg) (dissolved in DMSO). After extraction of the substances, Bufalin and Lycorine were quantified by liquid chromatography (LC) and quadrupole time-of-flight mass spectrometry (QTOF-MS) (see FIG. 30).

The data show that the compounds, particularly Lycorine are effectively taken up by the heart evidenced by higher levels in the myocardium in comparison to the plasma after injection of the compounds.

Example 20: Screening of Chemical Derivatives of Bufalin and Lycorine In Vitro The cells were incubated for 24 h with 10 µM Bufalin and Lycorine and with 10 µM derivatives of Bufalin (derivatives 3, 5, 6, 7, 8, 9, 10, 11, 12, 13, 14, 16, 17, 18 and 25) and Lycorine (derivative 1, 2, 4, 15, 19, 20, 21, 22, 23, 24 and 26). Then, proliferation of HCFs was measured by BrdU-ELISA (see FIG. 31).

The data show that the derivatives of the present invention are capable of preventing the proliferation of HCF such as the proliferation is prevented by Bufalin and Lycorine themselves. Preferably, Homoharringtonine (No. 19 in FIG. 31), a lycorine derivative, prevents the proliferation of HCF best.

Example 21: In Vitro Assessment of Anti-Fibrotic Actions of Bufalin and Lycorine on Non-Cardiac Fibroblasts Cells of the rat renal fibroblast cell line NRK49F and primary human pulmonary fibroblasts (HPFs) were treated with Lycorine (1 µM, 5 µM and 10 µM) or Bufalin (0.1 µM, 1 μM, 10 μM) for 24 h and proliferation of respective fibroblasts was measured by BrdU-ELISA (see FIG. 39).

It was shown, that Lycorine significantly inhibits proliferation of renal fibroblasts, but also of pulmonary fibroblasts. Additionally, Bufalin significantly inhibits only proliferation of pulmonary fibroblasts. Here, the most effective amount for Lycorine and Bufalin is 10 μM.

Thus, these results demonstrate that Bufalin and Lycorine also treat or prevent lung and kidney fibrosis.

REFERENCES

Birbrair A, Zhang T, Files D C, Mannava S, Smith T, Wang Z, Messi M L, Mintz A, Delbono O (2014) *"Type-1 pericytes accumulate after tissue injury and produce collagen in an organ-dependent manner"*. Stem Cell Research & Therapy. 5 (6): 122.

Grollmann A (1967) *"Inhibitors of protein biosynthesis"*. The Journal of Biological Chemistry, Vol. 242, No. 13, Issue of July 10, pp. 3226-3233.

Guo Y, Wang Y, Cao L, Wang P, Qing J, Zheng Q, Shang L, Yin Z, Sun Y (2016) *"A conserved inhibitory mechanism of a Lycorine derivative against enterovirus and hepatitis C virus"*. Antimicrobial Agents and Chemotherapy, Vol. 60, No. 2, pp. 913-924.

Murakami Y, Toyoda H, Tanahashi T, Tanaka J, Kumada T, Yoshioka Y, Kosaka N, Ochiya T and Taguchi Y-h (2012) *"Comprehensive miRNA expression analysis in peripheral blood can diagnose liver disease"*. PLoS ONE 7(10): e48366.

Nathan M, Ying L C, Pierre C, David B, João L (2011) *"Assessment of Myocardial Fibrosis with Cardiac Magnetic Resonance"*. Journal of the American College of Cardiology. 2011; 57(8):891-903.

Neary, Watson and Baugh (2015) *"Epigenetics and the overhealing wound: the role of DNA methylation in fibrosis"*. Fibrogenesis & Tissue Repair. 8 (1).

O'Reilly S (2016) *"MicroRNAs in fibrosis: opportunities and challenges"*. Arthritis Research & Therapy (2016) 18:11.

Prassas I and Diamandis EP (2008) *"Novel therapeutic applications of cardiac glycosides"*. Nature Review, Vol. 7, pp. 926-935.

Rajasekaran S, Rajaguru P, Sudhakar Gandhi P S (2015) *"MicroRNAs as potential targets for progressive pulmonary fibrosis"*. Frontiers in Pharmacology. 2015; 6:254.

Schulte T W, Akinaga S, Soga S, Sullivan W, Stensgard B, Toft D, Neckers I M (1998) *"Antibiotic radicicol binds to the N-terminal domain of Hsp90 and shares important biologic activities with geldanamycin"*. Cell Stress & Chaperones (1998) 3 (2), 100-108.

Schulte C, Westermann D, Blankenberg S and Zeller T (2015) *"Diagnostic and prognostic value of circulating microRNAs in heart failure with preserved and reduced ejection fraction"*. World J Cardiol 2015 Dec. 26; 7(12): 843-860.

Thum T (2014) *"Noncoding RNAs and myocardial fibrosis"*. Nature Reviews Cardiology 11, 655-663.

Vegter E L, Meer van der P, Windt de LJ, Pinto Y M and Voors A A (2016) *"MicroRNAs in heart failure: from biomarker to target for therapy"*. European Journal of Heart Failure, 2016, European Society of Cardiology.

Wang J, Huang W, Xu R, Nie Y, Cao X, Meng J, Xu X, Hu S and Zheng Z (2012) *"MicroRNA-24 regulates cardiac fibrosis after myocardial infarction"*. J. Cell. Mol. Med. Vol 16, No 9, 2012, pp. 2150-2160.

Wang P, Yuan H H, Zhang X, Li Y P, Shang L Q and Yin Z (2014) *"Novel Lycorine derivatives as anticancer agents: Synthesis and in vitro biological evaluation"*. Molecules 2014, 19, 2469-2480.

Wilson M, Wynn T (2009) *"Pulmonary fibrosis: pathogenesis, etiology and regulation"*. Mucosal immunology, 2009; 2(2):103-121.

The invention claimed is:

1. A method of preventing or treating fibrosis comprising administering an effective amount of an inhibitor of miR-671-5p, wherein the inhibitor is Lycorine or a derivative thereof, wherein fibrosis is cardiac fibrosis, lung fibrosis, liver fibrosis, kidney fibrosis, gastrointestinal fibrosis, skeletal muscle fibrosis, systemic sclerosis, multifocal fibrosclerosis, sclerodermatous graft-versus-host disease (GVHD) in bone marrow transplantation recipients, nephrogenic systemic fibrosis or dermal fibrosis and wherein the derivative is selected from the group consisting of

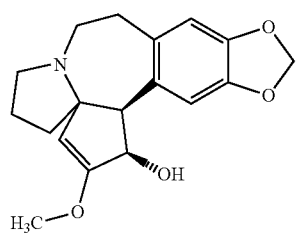

Cephalotaxine

-continued

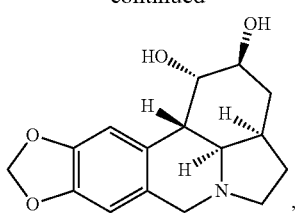
Dihydrolycorine

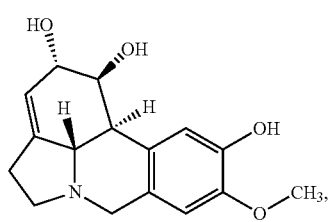
Pseudolycorine

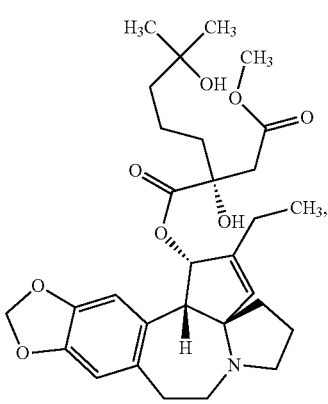
Homoharringtonine

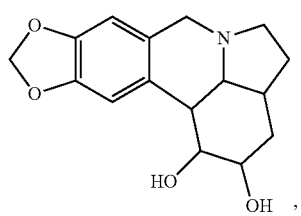
Lycobetaine

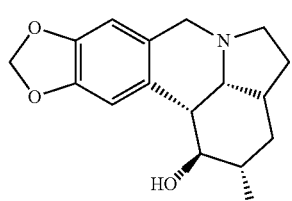
Amb24179473

-continued

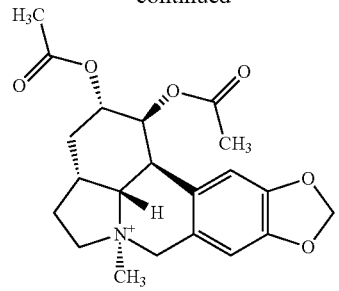
N-methyl-Nartazine

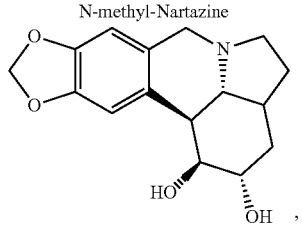
alpha-Dihydrolycorine

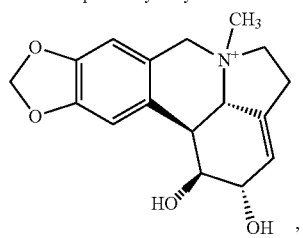
N-methyl-lycorine

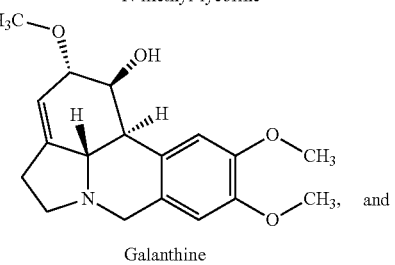
Galanthine, and

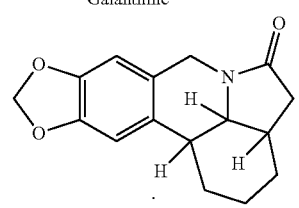
Amb24051775

2. The method of claim 1, wherein fibrosis is cardiac fibrosis, lung fibrosis or kidney fibrosis.

3. The method of claim 1, wherein the inhibitor is administered every other day for a time period of two weeks, three weeks, four weeks, five weeks or longer, optionally for two consecutive weeks.

4. The method of claim 3, wherein said administration of the inhibitor is performed by injections or by infusions.

5. The method of claim 3, wherein said administration of the inhibitor is performed intraperitoneally, intravenously, subcutaneously, intramuscularly or orally.

6. A kit comprising the inhibitor of miR-671-5p according to claim 1.

* * * * *

SEQUENCE LISTING

```
<160> NUMBER OF SEQ ID NOS: 47

<210> SEQ ID NO 1
<211> LENGTH: 23
<212> TYPE: RNA
<213> ORGANISM: artificial sequence
<220> FEATURE:
<223> OTHER INFORMATION: micro RNA hsa-miR-671-5p

<400> SEQUENCE: 1
aggaagcccu ggaggggcug gag                                             23

<210> SEQ ID NO 2
<211> LENGTH: 24
<212> TYPE: RNA
<213> ORGANISM: artificial sequence
<220> FEATURE:
<223> OTHER INFORMATION: micro RNA hsa-miR-7974

<400> SEQUENCE: 2
aggcugugau gcucuccuga gccc                                            24

<210> SEQ ID NO 3
<211> LENGTH: 23
<212> TYPE: RNA
<213> ORGANISM: artificial sequence
<220> FEATURE:
```

<223> OTHER INFORMATION: micro RNA hsa-miR-103a-3p

<400> SEQUENCE: 3
agcagcauug uacagggcua uga                                          23

<210> SEQ ID NO 4
<211> LENGTH: 22
<212> TYPE: RNA
<213> ORGANISM: artificial sequence
<220> FEATURE:
<223> OTHER INFORMATION: micro RNA hsa-miR-4521

<400> SEQUENCE: 4
gcuaaggaag uccugugcuc ag                                           22

<210> SEQ ID NO 5
<211> LENGTH: 17
<212> TYPE: RNA
<213> ORGANISM: artificial sequence
<220> FEATURE:
<223> OTHER INFORMATION: micro RNA hsa-miR-4443

<400> SEQUENCE: 5
uuggaggcgu ggguuuu                                                 17

<210> SEQ ID NO 6
<211> LENGTH: 22
<212> TYPE: RNA
<213> ORGANISM: artificial sequence
<220> FEATURE:
<223> OTHER INFORMATION: micro RNA hsa-miR-23b-5p

<400> SEQUENCE: 6
uggguuccug gcaugcugau uu                                           22

<210> SEQ ID NO 7
<211> LENGTH: 22
<212> TYPE: RNA
<213> ORGANISM: artificial sequence
<220> FEATURE:
<223> OTHER INFORMATION: micro RNA hsa-miR-100-3p

<400> SEQUENCE: 7
caagcuugua ucuauaggua ug                                           22

<210> SEQ ID NO 8
<211> LENGTH: 18
<212> TYPE: RNA
<213> ORGANISM: artificial sequence
<220> FEATURE:
<223> OTHER INFORMATION: micro RNA hsa-miR-7977

<400> SEQUENCE: 8
uucccagcca acgcacca                                                18

<210> SEQ ID NO 9
<211> LENGTH: 21
<212> TYPE: RNA
<213> ORGANISM: artificial sequence
<220> FEATURE:
<223> OTHER INFORMATION: micro RNA hsa-miR-3648

<400> SEQUENCE: 9
agccgcgggg aucgccgagg g                                            21

```
<210> SEQ ID NO 10
<211> LENGTH: 23
<212> TYPE: RNA
<213> ORGANISM: artificial sequence
<220> FEATURE:
<223> OTHER INFORMATION: micro RNA hsa-miR-128-1-5p

<400> SEQUENCE: 10
cggggccgua gcacugucug aga                                                 23

<210> SEQ ID NO 11
<211> LENGTH: 24
<212> TYPE: RNA
<213> ORGANISM: artificial sequence
<220> FEATURE:
<223> OTHER INFORMATION: micro RNA hsa-miR-29b-1-5p

<400> SEQUENCE: 11
gcugguuuca uauggugguu uaga                                                24

<210> SEQ ID NO 12
<211> LENGTH: 21
<212> TYPE: RNA
<213> ORGANISM: artificial sequence
<220> FEATURE:
<223> OTHER INFORMATION: micro RNA hsa-miR-192-5p

<400> SEQUENCE: 12
cugaccuaug aauugacagc c                                                   21

<210> SEQ ID NO 13
<211> LENGTH: 22
<212> TYPE: RNA
<213> ORGANISM: artificial sequence
<220> FEATURE:
<223> OTHER INFORMATION: micro RNA hsa-miR-605-3p

<400> SEQUENCE: 13
agaaggcacu augagauuua ga                                                  22

<210> SEQ ID NO 14
<211> LENGTH: 22
<212> TYPE: RNA
<213> ORGANISM: artificial sequence
<220> FEATURE:
<223> OTHER INFORMATION: micro RNA hsa-miR-370-5p

<400> SEQUENCE: 14
caggucacgu cucugcaguu ac                                                  22

<210> SEQ ID NO 15
<211> LENGTH: 23
<212> TYPE: RNA
<213> ORGANISM: artificial sequence
<220> FEATURE:
<223> OTHER INFORMATION: micro RNA hsa-miR-152-5p

<400> SEQUENCE: 15
agguucugug auacacuccg acu                                                 23

<210> SEQ ID NO 16
<211> LENGTH: 21
<212> TYPE: RNA
<213> ORGANISM: artificial sequence
<220> FEATURE:
<223> OTHER INFORMATION: micro RNA hsa-miR-25-5p
```

<400> SEQUENCE: 16
aggcggagac uugggcaauu g         21

<210> SEQ ID NO 17
<211> LENGTH: 21
<212> TYPE: RNA
<213> ORGANISM: artificial sequence
<220> FEATURE:
<223> OTHER INFORMATION: micro RNA hsa-miR-671-3p

<400> SEQUENCE: 17
uccgguucuc agggcuccac c         21

<210> SEQ ID NO 18
<211> LENGTH: 22
<212> TYPE: RNA
<213> ORGANISM: artificial sequence
<220> FEATURE:
<223> OTHER INFORMATION: micro RNA hsa-miR-1226-3p

<400> SEQUENCE: 18
ucaccagccc uguguucccu ag        22

<210> SEQ ID NO 19
<211> LENGTH: 22
<212> TYPE: RNA
<213> ORGANISM: artificial sequence
<220> FEATURE:
<223> OTHER INFORMATION: micro RNA hsa-miR-296-3p

<400> SEQUENCE: 19
gaggguuggg uggaggcucu cc        22

<210> SEQ ID NO 20
<211> LENGTH: 23
<212> TYPE: RNA
<213> ORGANISM: artificial sequence
<220> FEATURE:
<223> OTHER INFORMATION: micro RNA hsa-miR-409-5p

<400> SEQUENCE: 20
agguuacccg agcaacuuug cau       23

<210> SEQ ID NO 21
<211> LENGTH: 22
<212> TYPE: RNA
<213> ORGANISM: artificial sequence
<220> FEATURE:
<223> OTHER INFORMATION: micro RNA hsa-miR-221-5p

<400> SEQUENCE: 21
accuggcaua caauguagau uu        22

<210> SEQ ID NO 22
<211> LENGTH: 20
<212> TYPE: RNA
<213> ORGANISM: artificial sequence
<220> FEATURE:
<223> OTHER INFORMATION: micro RNA hsa-miR-33b-5p

<400> SEQUENCE: 22
gugcauugcu guugcauugc           20

<210> SEQ ID NO 23
<211> LENGTH: 22

```
<212> TYPE: RNA
<213> ORGANISM: artificial sequence
<220> FEATURE:
<223> OTHER INFORMATION: micro RNA hsa-miR-502-3p

<400> SEQUENCE: 23
aaugcaccug ggcaaggauu ca                                              22

<210> SEQ ID NO 24
<211> LENGTH: 22
<212> TYPE: RNA
<213> ORGANISM: artificial sequence
<220> FEATURE:
<223> OTHER INFORMATION: micro RNA hsa-miR-132-3p

<400> SEQUENCE: 24
uaacagucua cagccauggu cg                                              22

<210> SEQ ID NO 25
<211> LENGTH: 24
<212> TYPE: RNA
<213> ORGANISM: artificial sequence
<220> FEATURE:
<223> OTHER INFORMATION: micro RNA hsa-miR-1301-3p

<400> SEQUENCE: 25
uugcagcugc cugggaguga cuuc                                            24

<210> SEQ ID NO 26
<211> LENGTH: 22
<212> TYPE: RNA
<213> ORGANISM: artificial sequence
<220> FEATURE:
<223> OTHER INFORMATION: micro RNA hsa-miR-125b-5p

<400> SEQUENCE: 26
ucccugagac ccuaacuugu ga                                              22

<210> SEQ ID NO 27
<211> LENGTH: 21
<212> TYPE: RNA
<213> ORGANISM: artificial sequence
<220> FEATURE:
<223> OTHER INFORMATION: micro RNA hsa-miR-27a-5p

<400> SEQUENCE: 27
augaccuaug aauugacaga c                                               21

<210> SEQ ID NO 28
<211> LENGTH: 21
<212> TYPE: RNA
<213> ORGANISM: artificial sequence
<220> FEATURE:
<223> OTHER INFORMATION: micro RNA hsa-miR-215-5p

<400> SEQUENCE: 28
augaccuaug aauugacaga c                                               21

<210> SEQ ID NO 29
<211> LENGTH: 22
<212> TYPE: RNA
<213> ORGANISM: artificial sequence
<220> FEATURE:
<223> OTHER INFORMATION: micro RNA hsa-miR-1271-5p

<400> SEQUENCE: 29
```

```
cuuggcaccu agcaagcacu ca                                              22

<210> SEQ ID NO 30
<211> LENGTH: 22
<212> TYPE: RNA
<213> ORGANISM: artificial sequence
<220> FEATURE:
<223> OTHER INFORMATION: micro RNA hsa-miR-100-5p

<400> SEQUENCE: 30
aacccguaga uccgaacuug ug                                              22

<210> SEQ ID NO 31
<211> LENGTH: 22
<212> TYPE: RNA
<213> ORGANISM: artificial sequence
<220> FEATURE:
<223> OTHER INFORMATION: micro RNA hsa-miR-218-1-3p

<400> SEQUENCE: 31
augguuccgu caagcaccau gg                                              22

<210> SEQ ID NO 32
<211> LENGTH: 21
<212> TYPE: RNA
<213> ORGANISM: artificial sequence
<220> FEATURE:
<223> OTHER INFORMATION: micro RNA hsa-miR-181b-3p

<400> SEQUENCE: 32
cucacugaac aaugaaugca a                                               21

<210> SEQ ID NO 33
<211> LENGTH: 22
<212> TYPE: RNA
<213> ORGANISM: artificial sequence
<220> FEATURE:
<223> OTHER INFORMATION: micro RNA hsa-miR-27b-5p

<400> SEQUENCE: 33
agagcuuagc ugauugguga ac                                              22

<210> SEQ ID NO 34
<211> LENGTH: 22
<212> TYPE: RNA
<213> ORGANISM: artificial sequence
<220> FEATURE:
<223> OTHER INFORMATION: micro RNA hsa-miR-132-5p

<400> SEQUENCE: 34
accguggcuu ucgauuguua cu                                              22

<210> SEQ ID NO 35
<211> LENGTH: 23
<212> TYPE: RNA
<213> ORGANISM: artificial sequence
<220> FEATURE:
<223> OTHER INFORMATION: micro RNA hsa-miR-330-3p

<400> SEQUENCE: 35
gcaaagcaca cggccugcag aga                                             23

<210> SEQ ID NO 36
<211> LENGTH: 23
<212> TYPE: RNA
<213> ORGANISM: artificial sequence
```

```
<220> FEATURE:
<223> OTHER INFORMATION: micro RNA hsa-miR-675-5p

<400> SEQUENCE: 36
uggugcggag agggcccaca gug                                              23

<210> SEQ ID NO 37
<211> LENGTH: 22
<212> TYPE: RNA
<213> ORGANISM: artificial sequence
<220> FEATURE:
<223> OTHER INFORMATION: micro RNA hsa-miR-451a

<400> SEQUENCE: 37
aaaccguuac cauuacugag uu                                               22

<210> SEQ ID NO 38
<211> LENGTH: 23
<212> TYPE: RNA
<213> ORGANISM: artificial sequence
<220> FEATURE:
<223> OTHER INFORMATION: micro RNA hsa-miR-92a-1-5p

<400> SEQUENCE: 38
agguugggau cgguugcaau gcu                                              23

<210> SEQ ID NO 39
<211> LENGTH: 22
<212> TYPE: RNA
<213> ORGANISM: artificial sequence
<220> FEATURE:
<223> OTHER INFORMATION: micro RNA hsa-miR-543

<400> SEQUENCE: 39
aaacauucgc ggugcacuuc uu                                               22

<210> SEQ ID NO 40
<211> LENGTH: 23
<212> TYPE: RNA
<213> ORGANISM: artificial sequence
<220> FEATURE:
<223> OTHER INFORMATION: micro RNA hsa-miR-770-5p

<400> SEQUENCE: 40
uccaguacca cgugucaggg cca                                              23

<210> SEQ ID NO 41
<211> LENGTH: 21
<212> TYPE: RNA
<213> ORGANISM: artificial sequence
<220> FEATURE:
<223> OTHER INFORMATION: micro RNA hsa-miR-142-5p

<400> SEQUENCE: 41
cauaaaguag aaagcacuac u                                                21

<210> SEQ ID NO 42
<211> LENGTH: 21
<212> TYPE: RNA
<213> ORGANISM: artificial sequence
<220> FEATURE:
<223> OTHER INFORMATION: micro RNA hsa-miR-188-5p

<400> SEQUENCE: 42
caucccuugc augguggagg g                                                21
```

```
<210> SEQ ID NO 43
<211> LENGTH: 21
<212> TYPE: RNA
<213> ORGANISM: artificial sequence
<220> FEATURE:
<223> OTHER INFORMATION: micro RNA hsa-miR-128-3p

<400> SEQUENCE: 43
ucacagugaa ccggucucuu u                                           21

<210> SEQ ID NO 44
<211> LENGTH: 22
<212> TYPE: RNA
<213> ORGANISM: artificial sequence
<220> FEATURE:
<223> OTHER INFORMATION: micro RNA hsa-miR-1185-1-3p

<400> SEQUENCE: 44
auauacaggg ggagacucuu au                                          22

<210> SEQ ID NO 45
<211> LENGTH: 23
<212> TYPE: RNA
<213> ORGANISM: artificial sequence
<220> FEATURE:
<223> OTHER INFORMATION: micro RNA hsa-miR-668-3p

<400> SEQUENCE: 45
ugucacucgg cucggcccac uac                                         23

<210> SEQ ID NO 46
<211> LENGTH: 22
<212> TYPE: RNA
<213> ORGANISM: artificial sequence
<220> FEATURE:
<223> OTHER INFORMATION: micro RNA hsa-miR-1343-3p

<400> SEQUENCE: 46
cuccuggggc ccgcacucuc gc                                          22

<210> SEQ ID NO 47
<211> LENGTH: 22
<212> TYPE: RNA
<213> ORGANISM: artificial sequence
<220> FEATURE:
<223> OTHER INFORMATION: micro RNA hsa-miR-26b-3p

<400> SEQUENCE: 47
ccuguucucc auuacuuggc uc                                          22
```